(12) United States Patent
Sasaki

(10) Patent No.: US 10,900,152 B2
(45) Date of Patent: Jan. 26, 2021

(54) CYLINDRICAL BANDAGE

(71) Applicant: TRESTECH CO., LTD., Aichi (JP)

(72) Inventor: Toshiya Sasaki, Ama-gun (JP)

(73) Assignee: TRESTECH CO., LTD., Aichi (JP)

( * ) Notice: Subject to any disclaimer, the term of this patent is extended or adjusted under 35 U.S.C. 154(b) by 476 days.

(21) Appl. No.: 15/740,428

(22) PCT Filed: Feb. 27, 2017

(86) PCT No.: PCT/JP2017/007279
§ 371 (c)(1),
(2) Date: Dec. 28, 2017

(87) PCT Pub. No.: WO2017/199520
PCT Pub. Date: Nov. 23, 2017

(65) Prior Publication Data
US 2018/0353345 A1 Dec. 13, 2018

(30) Foreign Application Priority Data

May 19, 2016 (JP) .................................. 2016-100360

(51) Int. Cl.
*D04B 1/26* (2006.01)
*D04B 1/22* (2006.01)
(Continued)

(52) U.S. Cl.
CPC .............. *D04B 1/265* (2013.01); *A61F 13/08* (2013.01); *D04B 1/108* (2013.01); *D04B 1/18* (2013.01);
(Continued)

(58) Field of Classification Search
CPC . D04B 1/108; D04B 1/18; D04B 1/22; D04B 1/265; A61F 13/08; A61F 2013/00238
See application file for complete search history.

(56) References Cited

U.S. PATENT DOCUMENTS 1,883,581 A * 10/1932 Cole ........................ D04B 9/38
66/51
3,290,904 A * 12/1966 Snyder .................... D04B 1/265
66/200
(Continued)

FOREIGN PATENT DOCUMENTS

DE          808 744 C       7/1951
EP          2199445 A1      6/2010
(Continued)

OTHER PUBLICATIONS

International Search Report for PCT/JP2017/007279, dated May 23, 2017.
(Continued)

*Primary Examiner* — Danny Worrell
(74) *Attorney, Agent, or Firm* — Sughrue Mion, PLLC; Richard C. Turner

(57) ABSTRACT

To achieve high fit corresponding to variation in dimensions and shapes in a section of a human body and high return-promoting-effect.
The cylindrical bandage (1) has increase and decrease in the number of stitches of row on one circle of a wale side to reflect a variation in circumference of a section of a human body in human body circumference dates $m_1, m_2, m_3, \ldots$. This bandage includes depression part (exterior convex part (42) where stitch shows convexity on the outside and concavity on the inside) and projection part (interior convex part (41) where stitch show concavity on the outside and convexity on the inside) on the inside being in contact with a wear part. The depression part and projection part are alternatively and continuously arranged in parallel in a circumferential direction. This bandage has continuous unevenness in the cross-section by knitting.

16 Claims, 19 Drawing Sheets

(51) Int. Cl.
  *D04B 1/10* (2006.01)
  *D04B 1/18* (2006.01)
  *A61F 13/08* (2006.01)

(52) U.S. Cl.
  CPC ............... *D04B 1/22* (2013.01); *D04B 1/26* (2013.01); *D10B 2403/0333* (2013.01)

(56) References Cited

U.S. PATENT DOCUMENTS

| | | | | |
|---|---|---|---|---|
| 3,889,494 | A * | 6/1975 | Patience | D04B 1/18 66/178 R |
| 4,027,667 | A * | 6/1977 | Swallow | A61F 13/08 602/63 |
| 4,172,456 | A * | 10/1979 | Zens | A61F 13/08 2/240 |
| 4,180,065 | A * | 12/1979 | Bowen | A61F 13/08 2/239 |
| 4,397,161 | A * | 8/1983 | Chesebro, Jr. | A41B 11/00 66/178 A |
| 4,502,301 | A * | 3/1985 | Swallow | A61F 13/08 602/62 |
| 6,012,177 | A * | 1/2000 | Cortinovis | A61F 13/08 2/239 |
| 6,430,970 | B1 * | 8/2002 | Gardon-Mollard | D04B 1/243 66/178 A |
| 7,043,329 | B2 * | 5/2006 | Dias | D04B 7/32 700/141 |
| 7,895,863 | B2 * | 3/2011 | Smith | D04B 1/18 66/172 E |
| 8,317,736 | B2 * | 11/2012 | Virkus | A61F 13/08 2/240 |
| 9,777,413 | B2 * | 10/2017 | Messier | D04B 9/52 |
| 2011/0196416 | A1 * | 8/2011 | Lambertz | A61F 13/08 606/201 |
| 2015/0245951 | A1 * | 9/2015 | Convert | D04B 1/18 66/178 A |
| 2018/0353345 | A1 * | 12/2018 | Sasaki | D04B 1/26 |

FOREIGN PATENT DOCUMENTS

| | | |
|---|---|---|
| JP | 9-296343 A | 11/1997 |
| JP | 2006-200112 A | 8/2006 |
| JP | 2006-219805 A | 8/2006 |
| JP | 2011-87938 A | 5/2011 |
| JP | 2011-115571 A | 6/2011 |
| JP | 2016-77331 A | 5/2016 |
| JP | 2016-077852 A | 5/2016 |
| WO | 2008/078623 A1 | 7/2008 |

OTHER PUBLICATIONS

Communication dated Sep. 17, 2020 from European Patent Office in EP Application No. 17798958.9, 11 pages.

* cited by examiner under no external force　　　under external force under no external force under external force under no external force under external force

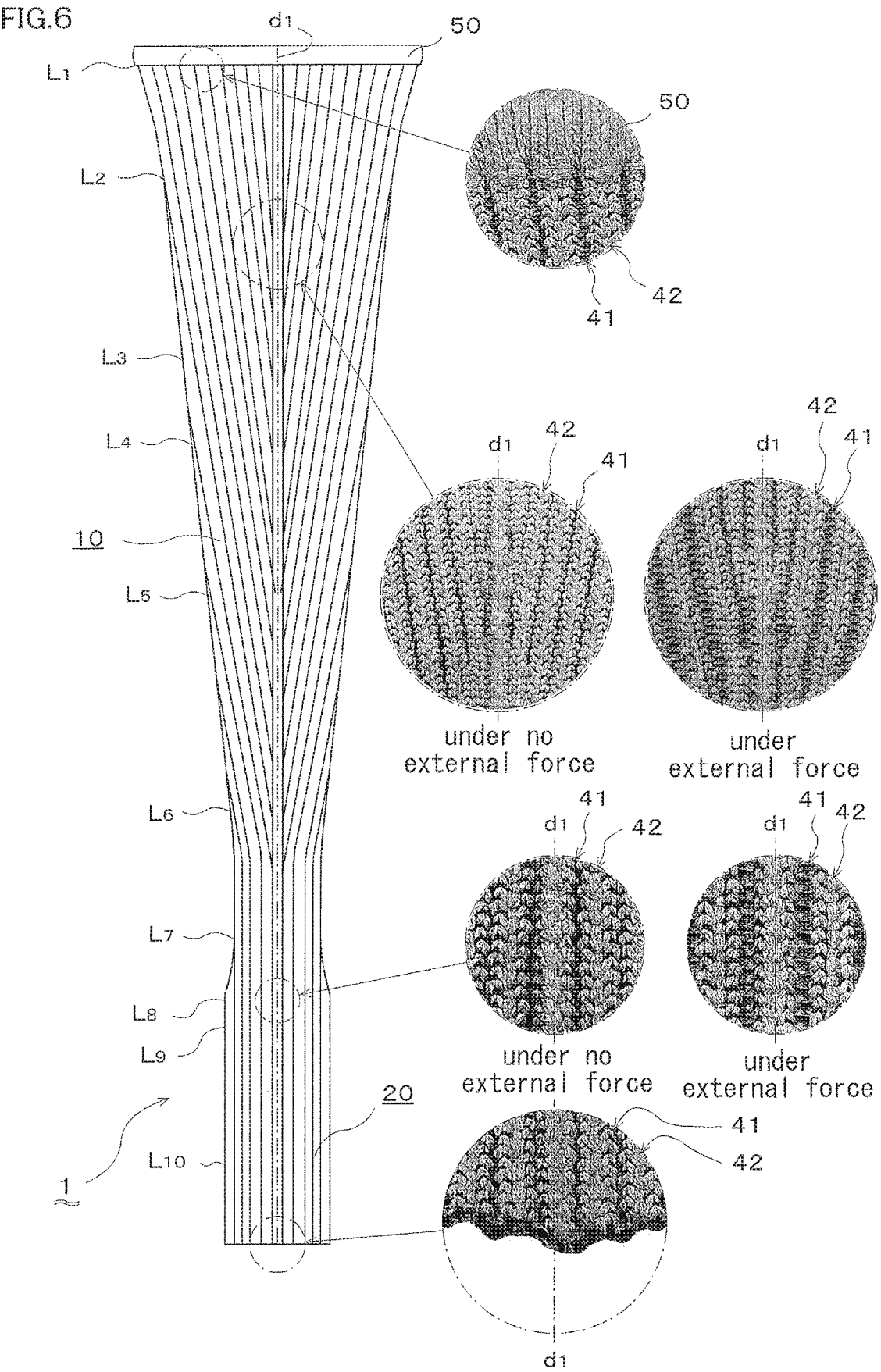

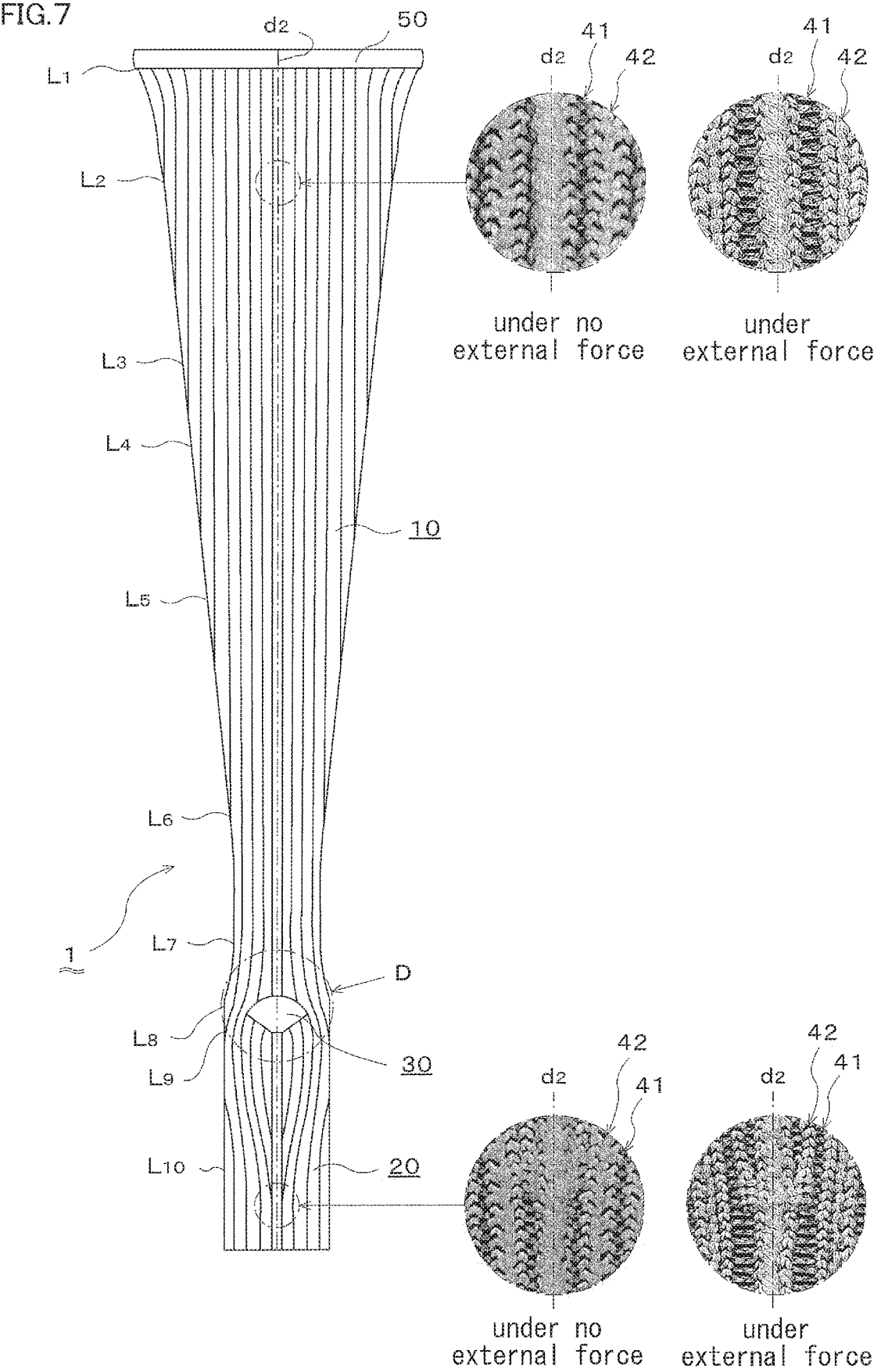

Measuring point h

CYLINDRICAL BANDAGE

CROSS REFERENCE TO RELATED APPLICATIONS

This application is a National Stage of International Application No. PCT/JP2017/007279 filed Feb. 27, 2017, claiming priority based on Japanese Patent Application No. 2016-100360, filed May 19, 2016, the contents of all of which are incorporated herein by reference in their entirety.

TECHNICAL FIELD

The present invention relates to wear that can puts pressure on a part of a human body. More specifically, the present invention relates to a cylindrical bandage, for example, that is used for bandage that compresses externally and is formed into a cylindrical shape such as a supporter for a lower extremity, a sleeve, a stocking, tights, an elbow supporter, or a supporter for a hand or a wrist, and more particularly, to a cylindrical bandage suitable for prevention and treatment of diseases, such as venous return failure and lymphedema.

BACKGROUND ART

In medical field, compression therapy such as bandage-formed compresses that are worn on and put pressure on affected parts and elastic stockings that are designed so as to decrease pressure in phases in the longitudinal direction, is effective for prevention and treatment of diseases, for example, venous return failure such as varicose vein and venous thrombosis in a lower extremity and lymphedema. In particular, no drugs and surgical operations have an effect on the treatment of lymphedema disease. Thus, the medical treatment of lymphedema currently depends on physical therapy, mainly the compression therapy. The lymphedema means the state where lymph nodes or lymph ducts were under pressure, tapered, and blockaded for some reason and thus the lymph fails to flow and the interstitial space or the intercellular space is excessively covered with moisture including proteins, lymphocytes, and others.

A Rolling-bandage-formed compression wraps a wear part of a wearer, which enables any wearers to be under pressure corresponding to the shape of the wear part. Unfortunately, this rolling-bandage-formed compression cannot put suitable pressure, which corresponds to the disease condition, on the affected part without special technique. Under un suitable pressure, the disease may get all the worse. Thus, it is difficult to wear the rolling-bandage-formed compression without the help of an expert, a doctor, or a nurse.

On the other hand, compressions formed into tubular shape, for example, an elastic stocking for lower extremity that is designed so as to gradually weaken compression from an ankle to a thigh, a sleeve, and a tubular bandage can be worn without experts and these compressions are prevented from falling down with wearing and have no need to adjust the compression.

Some medical elastic stockings known in the medical field, specifically, for lower extremity, have a bulge (round shape) in a part of tuber knit to correspond to shapes of the heel. Unfortunately, such medical elastic stockings have some slacks near the ankle, specifically, over range of a malleolus to an instep of the foot, and some wrinkles at the instep side while being worn. In some cases, the lines of these wrinkles, specifically horizontal lines, cut into the skin. This causes the compression to be concentrated and causes venous return to be prevented. At the same time, the cloth rises to the skin around the malleolus, specifically its back side, where the lymph fails to flow and it collects easily, thus providing small compression and failing to put appropriate pressure and providing unstable compression. Thus, cushion formed of foamed resin, sponge, or other materials cover the affected part around the malleolus to put equal pressure on the affected part around the malleolus that is under weak pressure. Additionally, the elastic stocking or the like covers on this cushion. This increases the compression around the malleolus currently.

In conventional knitting that use circular knitting machines, variation in tension of a yarn, stitch density, or a loop diameter allows various forms. Unfortunately, this knitting has no variation in the number of stitches and has fixed knitting-width with predetermined the number of the stitches basically. Such characteristic limits expression of dimensions and shapes. Thus, it is difficult to the knit to fit dimensions and shapes of a circumference of the ankle.

For circular knitting using a tubular-knitting machine, which has a cylindrical needle hook, for knitting lower extremity including the heel part, a leg part is first knitted by rotating the needle hook in a fixed direction and using all needles and thus the leg part is formed into the cylindrical shape. A heel part is secondly knitted by rotating and shuttling the needle hook within a fixed angle and using a part of the needles. Subsequently, a foot part is knitted by rotating the needle hook in a fixed direction and using all needles and thus the leg part is formed into the cylindrical shape again.

This circular knitting uses fixed needles and knitting-width for knitting. Thus, the circumference is limited in a predetermined range. This yields the fixed diameter in tube and causes the bottom end of the leg and the top end of the foot, where the leg and the foot are connected, to have the same knitting-width and fixed circumference by necessity. Additionally, the dimensions of the heel part are limited in a predetermined range. Thus, it is difficult to design the best diameters that fit the dimensions and shapes of the ankle. Small diameter with destiny stitches at ankle side causes bad air permeability and sweaty. Additionally, it is difficult for user to put on.

When the setup of the knitting is started for example, from the leg part, a rotation angle of the needle hook gradually decreases and subsequently the rotation angle of the needle hook gradually increases to knit the heel part. The foot part is knitted after it. When the heel part is knitted, the knitting-width gradually decreases and next gradually increases with using partial reverse-knitting. This forms gore lines at a connecting border between the increase region of the knitting-width (the number of the stitches) and decrease region of the knitting-width (the number of the stitches) in the heel part, which increase region has increase in the stitches and decrease region has decrease in the stitches. Thus, the gore lines easily create wrinkles and prevent stretch of the knit.

This circular knitting knit tends to have slack at the instep side of the foot, which is in the front of the ankle, and tightness and tension at the heel side, which is in the rear of the ankle. Thus, it is difficult for the knit to provide uniform compression that corresponds to the curvature in the malleolus of the foot. Such conventional elastic stocking knitted by the circular knitting provides concentration of the compression with wrinkles at the front of the ankle. Additionally, the conventional elastic stocking knitted by the circular knitting has high density stitches at the ankle part. Consequently, such conventional elastic stocking has bad air permeability and sweaty. The conventional elastic stocking formed of a nylon knit may cause an allergic reaction and eczema.

With respect to the compression, the patent publication No. 1 discloses cover wear for the lower extremity. In the patent publication No. 1, the cover wear for the lower extremity has projection parts with pile formed of the pile stitch on the inside, which is in contact with a skin of a wearer. Individual projection part is arrayed separately in the lengthwise direction at the front side of a crus part and is arrayed contiguously in the lengthwise direction at the rear side of the crus part. This forms partial compression parts. Pressure of compression parts yields stimulation and massage effect which improves swelling and tiredness in the leg.

It is known that a flatbed knitting machine that has the front-and-rear needle beds can knit socks having the heel part and the like in the patent publication No. 2 and No. 3.

PRIOR ART DOCUMENT(S)

Patent Document(S)

Patent Application No. 1: JP-A-2006-219805
Patent Application No. 2: JP-A-9-296343
Patent Application No. 3: WO2008/078623

DISCLOSURE OF THE INVENTION

Problems that the Invention is to Solve

Unfortunately, the pressure is limited to only the leg part the patent publication No. 1. This patent publication No. 1 fails to include the foot part including the malleolus regarding the pressure. In this patent publication No. 1, the front side and the rear side of the leg part are different in the arrangement of the partial compression parts. This causes ununiform and unbalance pressure. Thus, the pressure has effect on only partial part and the wearer may feel strange.

The sock that is disclosed in the patent publication No. 2 and No. 3 may used for daily life and general-purpose sock. Such general-purpose sock for daily life is designed so as to have slack to reflect the repeat bending at front side of the ankle part of the foot and to be easy to put on and taken off. The patent publication No. 2 and No. 3 have no idea for matching and providing uniform compression to the curvature shape around the malleolus part of the foot.

Thus, it is an object of the present invention to provide a cylindrical bandage, such as a lower extremity, that achieves high fit corresponding to variation in the dimensions and shapes in the section of the foot and yields high return-promoting-effect.

Means for Solving the Problem

A cylindrical bandage of the present invention claimed in claim 1 includes a variation in a circumference with a variation in the number of stitches of a stitch row on one circle (loop) of a wale side to correspond a variation in a section of a human body being the object of a wear. This cylindrical bandage is formed into an uneven shape in a section on an inside, which is brought into contact with a wear part of the human body. The uneven shape includes depression parts and projection parts formed by knitting. Each depression part and each projection part are arranged in parallel alternately and continue in the circumferential direction being perpendicular to a longitudinal direction by knitting.

Above-mentioned wale side is a row of loops where a yarn forming stitches continues in the widthwise direction (x-direction) of a knit. This wale side is distinguished from a course side where the yarn is loop-interknitted in a lengthwise direction (y-direction) of the knit.

Above-mentioned yarn used for the knit includes, for example, a spun yarn, a filament yarn, a monofilament yarn, a bulky yarn, a hollow yarn, a covering yarn, a core yarn, a composite yarn, a flat yarn, a modified cross-section yarn, a split yarn, or lacquer yarn. Material of the yarn is, for example, chemical material, metal, plant material, or a twist yarn which is a combination of such materials.

Above-mentioned variation in the circumference with the variation in the number of the stitches forming the stitch row on the one circle of the wale side, where the yarn forming the stitches continue, to correspond to the variation in the section of the human body means correspondence with the variation in the circumference of the section being perpendicular to the lengthwise of the human body by adjusting the number of stitches forming the stitch row on the one circle (loop) with the variation in the circumference on the wale side of the tube.

Above-mentioned uneven shape in the section, where each depression part and each projection part continue in the circumferential direction by knitting, means the depression part consisting of one or more stitches that shows a depression on the inside of the cylindrical bandage and the projection part consisting of one or more stitches that show a projection on the inside of the cylindrical bandage continue in the circumferential direction of the circle (the tube), which consisting of the stitch row on the one circle (loop) of the wale side. Thus, the cylindrical bandage is formed into the uneven shape (corrugated shape) in the cross-section on the inside. Such the depression part and projection part are formed, for example, by rib stitch, tuck stitch, or other means of the knitting.

A cylindrical bandage of the present invention claimed in claim 2 has each depression part extends continuously in the longitudinal direction (the course direction) and each projection part that extends continuously in the longitudinal direction (the course direction). This claim 2 is dependent on claim 1.

A cylindrical bandage of the present invention claimed in claim 3 has an outside that has higher tension of the circle on a circumferential direction than the inside one. The inside is brought into contact with the wear part of the human body and the outside is a reverse of the inside. This claim 3 is dependent on claim 1 or claim 2.

A cylindrical bandage of the present invention claimed in claim 4 has a difference in tension of the circle on a circumferential direction between the depression part and the projection part on the inside, which is brought into contact with the wear part of the human body. This claim 4 is dependent on one of claims 1-3.

A cylindrical bandage of the present invention claimed in claim 5 includes a variation in a circumference with a variation in the number of stitches of a stitch row on one circle (loop) of a wale side to correspond a variation in a section of a human body being the object of a wear. This cylindrical bandage is formed into an uneven shape in a section on an inside and an outside of a knit. The uneven shape includes depression parts and projection parts. Each depression part and each projection part are arranged in parallel alternately and continue in the circumferential direction being perpendicular to a longitudinal direction. This cylindrical bandage includes an exterior convex part and an interior convex part. The exterior convex part comprises a stitch showing concavity on the inside brought into contact with a wear part of the human body and convexity on the outside being a reverse of the inside. The interior convex part comprises a stitch showing convexity on the inside brought into contact with the wear part of the human body and concavity on the outside being the reverse of the inside. This interior convex part has an outline of the cross-section being closer curved line than an outline of the exterior convex part one.

Above-mentioned wale side is a row of loops where a yarn forming stitches continues in the widthwise direction (x-direction) of a knit. This wale side is distinguished from a course side where the yarn is loop-interknitted in a lengthwise direction (y-direction) of the knit.

Above-mentioned yarn used for the knit includes, for example, a spun yarn, a filament yarn, a monofilament yarn, a bulky yarn, a hollow yarn, a covering yarn, a core yarn, a composite yarn, a flat yarn, a modified cross-section yarn, a split yarn, or lacquer yarn. Material of the yarn is, for example, chemical material, metal, plant material, or a twist yarn which is a combination of such materials.

Above-mentioned variation in the circumference with the variation in the number of the stitches forming the stitch row on the one circle of the wale side, where the yarn forming the stitches continue, to correspond to the variation in the section of the human body means correspondence with the variation in the circumference of the section being perpendicular to the lengthwise of the human body by adjusting the number of stitches forming the stitch row on the one circle (loop) with the variation in the circumference on the wale side of the tube.

Above-mentioned uneven shape in the section, where each depression part and each projection part continue in the circumferential direction by knitting, means the depression part and the projection part continue in the circumferential direction of the circle (the tube), which consisting of the stitch row on the one circle (loop) of the wale side. Thus, the cylindrical bandage is formed into the uneven shape (corrugated shape) in the cross-section on the inside. Such the depression part and projection part are formed, for example, by rib stitch, tuck stitch, or other means of the knitting.

Above-mentioned the interior convex part having the outline of the section being closer curved line than the outline of the exterior convex part one means that the interior convex part, which comprises a stitch showing convexity on the inside brought into contact with the wear part of the human body, has a round shape compared with the exterior convex part, which comprises a stitch showing convexity on the outside, in the cross-section of the cylindrical bandage.

A cylindrical bandage of the present invention claimed in claim 6 has the exterior projection part and the interior projection part that each extends continuously in the longitudinal direction (the course side). This claim 6 is dependent on claim 5.

A cylindrical bandage of the present invention claimed in claim 7 has a thickness of the knit that is within a range of 2 to 15 mm, preferably, 5 to 15 mm, under no external force. This claim 7 is dependent on one of claims 1-6.

A cylindrical bandage of the present invention claimed in claim 8 has compression that is within a range from 3 to 70 mmHg, preferably, 15 to 50 mmHg, more preferably, 20 to 45 mmHg, at a base part around a lateral malleolus part near a heel side of a foot while being worn on a circumference of an ankle joint of the human body. This claim 8 is dependent on one of claims 1-7.

Above-mentioned compression is measured by using air-pack-type-close contact-surface-pressure-measuring-system (which is made by AMI TECHNO, Inc. AMI3037-SB-SET) under conditions where the cylindrical bandage is worn on the foot-mold (left leg) that is used for a display for men's five-toed socks (TENKENSOUI, Co., Ltd. 51-196-10-2).

Above-mentioned compression of the base part around the lateral malleolus part near the heel side of the foot is measured at a rear side of the lateral malleolus part of the foot, which is near the heel side, and a substantially flatness part corresponding to the foot part of the lateral malleolus, which rises.

Above-mentioned range of the number has no requirements for a precise mathematical sense and allows a few percent error ranges for characteristics including measurement accuracy.

A cylindrical bandage of the present invention claimed in claim 9 has a difference in compression that is 40% or less, preferably, 30% or less, more preferably, 10% or less, between a base part around a lateral malleolus part near a heel side of the foot and an instep part of the foot while being worn on a circumference of an ankle joint of the human body. This claim 9 is dependent on one of claims 1-8.

Above-mentioned compression is measured by using air-pack-type-close contact-surface-pressure-measuring-system (which is made by AMI TECHNO, Inc. AMI3037-SB-SET) under conditions where the cylindrical bandage is worn on the foot-mold (left leg) that is used for a display for men's five-toed socks (TENKENSOUI, Co., Ltd. 51-196-10-2).

Above-mentioned compression of the base part around the lateral malleolus part near the heel side of the foot is measured at a rear side of the lateral malleolus part of the foot, which is near the heel side, and a substantially flatness part corresponding to the foot part of the lateral malleolus, which rises.

The compression of the instep of the foot is measured on the front and middle part of the ankle side and the part just above the top of a plantar arch.

Above-mentioned range of the number has no requirements for a precise mathematical sense and allows a few percent error ranges for characteristics including measurement accuracy.

A cylindrical bandage of the present invention claimed in claim 10 has a larger diameter of a circle at an endmost part of a second tubular knit than a diameter of a circle at an endmost part of a first tubular knit in a connection between the first tubular knit and the second tubular knit following the first tubular knit. The circle of the endmost part of the second tubular knit is on a wale side and follows the first tubular knit. The circle of the endmost part of the first tubular knit is on a wale side and follows the second tubular knit. The cylindrical bandage has a connecting knit that is formed by increasing the number of the stitches on the course side, where a yarn is loop-interknitted, between the first tubular knit and the second tubular knit. This connecting knit connects difference in the diameter between the first tubular knit and the second tubular knit following it. In the cylindrical bandage, a length (a) of a virtual perpendicular line, which runs from a border between the first tubular knit, the second tubular knit, and the connecting knit to a symmetrical line where the first tubular knit is followed by the second tubular knit, and a length (b) of a virtual perpendicular line, which runs from the border to the symmetrical line in the connecting knit side, are in the ratio 6:4≤(a):(b) ≤9:1 under a condition where the cylindrical bandage is folded along a symmetrical line of the first tubular knit and the second tubular knit to divide a circumference of the circle (tube) on the wale side into half and one of insides of the circle is in contact with the other opposite inside of the circle.

Above-mentioned wale side is a row of loops in the widthwise direction (x-direction) of a knit. In this wale side, a yarn forming stitches continues. Above-mentioned course side is a column of loops in a lengthwise direction (y-direction) of the knit. In this course side, the yarn is interknitted into loop shapes.

Above-mentioned yarn used for the knit includes, for example, a spun yarn, a filament yarn, a monofilament yarn, a bulky yarn, a hollow yarn, a covering yarn, a core yarn, a composite yarn, a flat yarn, a modified cross-section yarn, a split yarn, or lacquer yarn. Material of the yarn is, for example, chemical material, metal, plant material, or a twist yarn which is a combination of such materials. The kinds of the knitting include plain stitch including rib stitch, net stitch, and pattern stitch, stretch jersey, bare jersey stitch, and purl stitch. In some embodiment, a base formation of the first tubular knit and the second tubular knit may be formed of the rib stitch, enabling return-promoting-effect to increase.

Above-mentioned symmetrical line is a virtual line which divides the knit into half symmetrically in a way that the circumference of the circle (tube) on the one circle (loop) of the wale side in the first tubular knit and the second tubular knit are divided into half. In above-mentioned connection between the first tubular knit and the second tubular knit and the connecting knit in a state in which the cylindrical bandage is folded, the length (a) of the virtual perpendicular line, which runs from a border between the first tubular knit, the second tubular knit, and the connecting knit to the symmetrical line, where the first tubular knit is followed by the second tubular knit, and the length (b) of the virtual perpendicular line, which runs from the border to the symmetrical line in the connecting knit side, are in the ratio $6:4 \leq (a):(b) \leq 9:1$ under conditions where the external force is applied.

In the cylindrical bandage, the diameter of the circle that is formed of the stitch row on the one circle (loop) of the second tubular knit and follows the first tubular knit and the connecting knit is larger than the diameter of the circle that is formed of the stitch row on the one circle (loop) of the first tubular knit and follows the second tubular knit and the connecting knit. This means that the circumference of the circle and a knitting-width of the endmost part that is on the wale side in the second tubular knit and follows the first tubular knit and the connecting knit is larger than the circumference of the circle and a knitting-width of the endmost part that is on the wale side in the first tubular knit and follows the second tubular knit and the connecting knit.

Above-mentioned range of the number has no requirements for a precise mathematical sense and allows a few percent error ranges for characteristics including the kind of yarn and the means of knitting.

A cylindrical bandage of the present invention claimed in claim 11 has the connecting knit that follows a range of 10 to 40%, preferably, 20 to 40%, of the circumference of the circle and knitting-width of the endmost part of the first tubular knit. Such circle is formed of the stitch row on the one circle of the wale side and the endmost part of the first tubular follows the second tubular knit and the connecting knit. Additionally, the connecting knit follows a range of 10 to 40%, preferably, 20 to 40%, of the circumference of the circle and knitting-width of the endmost part of the second tubular knit. Such circle is formed of the stitch row on the one circle of the wale side and the endmost part of the second tubular follows the first tubular knit and the connecting knit. Thus, the connecting knit lies between the first tubular knit and the second tubular knit. A following distance or length in which the connecting knit follows the second tubular knit is longer than a following distance or length in which the connecting knit follows the first tubular knit. This claim 11 is dependent on claim 10.

Above-mentioned range of the number has no requirements for a precise mathematical sense and allows a few percent error ranges for characteristics including the kind of yarn and the means of knitting.

A cylindrical bandage of the present invention claimed in claim 12 has the first tubular knit that has a thickness being within a range of 2 to 15 mm in the cross-section and the second tubular knit that has a thickness being within a range of 2 to 15 mm in the cross-section, under no external force. This claim 12 is dependent on claim 10 or claim 11.

A cylindrical bandage of the present invention claimed in claim 13 has compression that is within a range from 3 to 70 mmHg, preferably, 15 to 50 mmHg, more preferably, 20 to 45 mmHg, at a base part around a lateral malleolus part near a heel side of a foot while being worn on a circumference of an ankle joint of the human body. This claim 13 is dependent on one of claims 10-12.

Above-mentioned compression is measured by using air-pack-type-close contact-surface-pressure-measuring-system (which is made by AMI TECHNO, Inc. AMI3037-SB-SET) under conditions where the cylindrical bandage is worn on the foot-mold (left leg) that is used for a display for men's five-toed socks (TENKENSOUI, Co., Ltd. 51-196-10-2).

Above-mentioned compression of the base part around the lateral malleolus part near the heel side of the foot is measured at a rear side of the lateral malleolus part of the foot, which is near the heel side, and a substantially flatness part corresponding to the foot part of the lateral malleolus, which rises.

Above-mentioned range of the number has no requirements for a precise mathematical sense and allows a few percent error ranges for characteristics including measurement accuracy.

A cylindrical bandage of the present invention claimed in claim 14 has a difference in compression that is 40% or less, preferably, 30% or less, more preferably, 10% or less, between a base part around a lateral malleolus part near a heel side of the foot and an instep part of the foot while being worn on a circumference of an ankle joint of the human body. This claim 14 is dependent on one of claims 10-13.

Above-mentioned compression is measured by using air-pack-type-close contact-surface-pressure-measuring-system (which is made by AMI TECHNO, Inc. AMI3037-SB-SET) under conditions where the cylindrical bandage is worn on the foot-mold (left leg) that is used for a display for men's five-toed socks (TENKENSOUI, Co., Ltd. 51-196-10-2).

Above-mentioned compression of the base part around the lateral malleolus part near the heel side of the foot is measured at a rear side of the lateral malleolus part of the foot, which is near the heel side, and a substantially flatness part corresponding to the foot part of the lateral malleolus, which rises.

The compression of the instep of the foot is measured on the front and middle part of the ankle side and the part just above the top of a plantar arch.

Above-mentioned range of the number has no requirements for a precise mathematical sense and allows a few percent error ranges for characteristics including measurement accuracy.

Effects of the Invention

A cylindrical bandage of the present invention claimed in claim 1 includes a variation in the number of stitches of a stitch row on a circle of a wale side along a longitudinal direction to correspond to a variation in a section of a human body. Thus, this cylindrical bandage can correspond to a difference in dimensions and shapes of the section along a lengthwise of the human body. The variation in the number of stitches on the basis of the variation in the section of the human body enables a lot of expression in the dimensions and shapes and enables a circumference to be freely-selected. Additionally, it is easy to determine the best diameter corresponding to the dimensions and shapes of the section of the human body. Consequently, the cylindrical bandage achieves a good fit. For example, this cylindrical bandage can fit a circumference of an ankle joint, which has a lot of variation in dimensions and shapes of the section, very well. This cylindrical bandage is prevented from having slack and wrinkles and tightness, which are caused by excess or short of the knit. This cylindrical bandage allows the knit to be in close contact with even a depression in the circumference of the ankle joint. Additionally, the variation in the number of the stitches allows adjustment of the circumference of the circle, determining any diameter of the loop. This allows sufficient elasticity. This cylindrical bandage is prevented from cutting into the skin and thus prevented from providing a concentration of compression and having a decline of air permeability. Additionally, this cylindrical bandage is easily put on and taken off.

The cylindrical bandage includes the depression part and the projection part that are alternately arranged in parallel and continue in the circumferential direction on the circle (the tube) by knitting. Thus, this cylindrical bandage is formed into an uneven shape in a section on an inside brought into contact with a wear part. These depression and projection yield a difference of the compression in a circumferential direction being perpendicular to a longitudinal direction of the human body while the cylindrical bandage is worn. This improves a flow of lymph and return-promoting-effect. Additionally, a wearer is under well-balanced pressure and thus feels no strange.

Thus, the cylindrical bandage achieves a good fit corresponding to the variation in the dimensions and shapes of the section of the human body. Additionally, the knit of this cylindrical bandage that is brought into contact with the wear part is formed into the uneven shape in the section, where the depression and the projection continue in the circumferential direction. This improves the return-promoting-effect, that is, this yields high return-promoting-effect.

A cylindrical bandage of the present invention claimed in claim 2 has the depression part and the projection part that each extends continuously in the longitudinal direction. This causes strength and weakness in the compression to run in conformance with the flow direction of the lymph. This enables more improvement of the flow of the lymph and more improvement of the return-promoting-effect in addition to the advantages recited in claim 1.

In cylindrical bandage of the present invention claimed in claim 3, the tension of the circle is higher on an outside, which is a reverse of the inside, than on the inside, which is brought into contact with the wear part. This allows the depression part on the inside, which is brought into contact with the wear part, to have much larger volume in the thickness direction and have a curvature. This enables the depression part to be in contact with the wear part more widely or more closely, thus enabling enhancement of the compression in addition to the advantages recited in claim 1 or claim 2.

A cylindrical bandage of the present invention claimed in claim has a difference in tension of the circle between the depression part and the projection part on the inside, which is brought into contact with the wear part. This difference in the tension allows depression part on the inside, which is brought into contact with the wear part, to have much larger volume in the thickness direction and have a curvature. This enables the depression part to be in contact with the wear part much more widely or more closely, thus enabling enhancement of the compression more effectively in addition to the advantages recited in one of claims 1-3.

A cylindrical bandage of the present invention claimed in claim 5 includes a variation in the number of stitches of a stitch row on a circle of a wale side along a longitudinal direction to correspond to a variation in a section of a human body. Thus, this cylindrical bandage can correspond to a difference in dimensions and shapes of the section along a lengthwise of the human body. The variation in the number of stitches on the basis of the variation in the section of the human body enables a lot of expression in the dimensions and shapes and enables a circumference to be freely-selected. Additionally, it is easy to determine the best diameter corresponding to the dimensions and shapes of the section of the human body. Consequently, the cylindrical bandage achieves a good fit. For example, this cylindrical bandage can fit a circumference of an ankle joint, which has a lot of variation in dimensions and shapes of the section, very well. This cylindrical bandage is prevented from having slack and wrinkles and tightness, which are caused by excess or short of the knit. This cylindrical bandage allows the knit to be in close contact with even a depression in the circumference of the ankle joint. Additionally, the variation in the number of the stitches allows adjustment of the circumference of the circle, determining any diameter of the loop. This allows sufficient elasticity. This cylindrical bandage is prevented from cutting into the skin and thus prevented from providing a concentration of compression and having a decline of air permeability. Additionally, this cylindrical bandage is easily put on and taken off.

The cylindrical bandage includes the depression part and the projection part that are alternately arranged in parallel and continue in the circumferential direction on the circle (the tube). Thus, this cylindrical bandage is formed into an uneven shape in a section on a front and a rear of the knit. These depression and projection yield a difference of the compression in a circumferential direction being perpendicular to a longitudinal direction of the human body while the cylindrical bandage is worn. This improves a flow of lymph and return-promoting-effect. Additionally, a wearer is under well-balanced pressure and thus feels no strange.

The cylindrical bandage includes an exterior convex part and an interior convex part. The exterior convex part comprises a stitch showing concavity on the inside brought into contact with a wear part of the human body and convexity on the outside being a reverse of the inside. The interior convex part comprises a stitch showing convexity on the inside brought into contact with the wear part of the human body and concavity on the outside being the reverse of the inside. This interior convex part has an outline of the cross-section being closer curved line than an outline of the exterior convex part one. Consequently, this interior convex part is in contact with the wear part more widely or more closely, thus enabling enhancement of the compression.

Thus, the cylindrical bandage achieves a good fit corresponding to the variation in the dimensions and shapes of the section of the human body. Additionally, the knit of this cylindrical bandage that is brought into contact with the wear part is formed into the uneven shape in the section, where the depression and the projection continue in the circumferential direction. This improves the return-promoting-effect, that is, this yields high return-promoting-effect.

A cylindrical bandage of the present invention claimed in claim 6 has the exterior projection part and the interior projection part that each extends continuously in the longitudinal direction. This causes strength and weakness in the compression to run in conformance with the flow direction of the lymph. This enables more improvement of the flow of the lymph and more improvement of the return-promoting-effect in addition to the advantages recited in claim 5.

In a cylindrical bandage of the present invention claimed in claim 7, a thickness of its knit is within a range of 2 to 15 mm in a cross-section. Thus, it is difficult for the knit to have wrinkles. In particular, it is difficult for even the knit at the part having movement such as bending, for example, the knit at an instep side of the foot, to create wrinkles while the cylindrical bandage is worn. This cylindrical bandage is prevented from providing a concentration of the compression and tourniquet action with wrinkles cutting into the skin in addition to the advantages recited in one of claims 1 to 6.

A cylindrical bandage of the present invention claimed in claim 8 provides compression that is within a range from 3 to 70 mmHg at a base part around a lateral malleolus part near a heel side of the foot while being worn on a circumference of an ankle joint of the human body.

If this compression is less than 3 mmHg, the cylindrical bandage fails to provide return-promoting-effect. If this compression is greater than 70 mmHg, the cylindrical bandage prevents the return-promoting conversely.

The cylindrical bandage of the present invention claimed in claim 8 is prevented from having wrinkles and tightness (tension) in the knit at the circumference of the ankle joint of the human body and thus its knit can fit and be in close contact with the circumference of the ankle joint of the human body. This enables the cylindrical bandage to provide 15 mmHg and more compression at the circumference of the malleolus, specifically, a base part around the malleolus part near heel side of the foot, where it is difficult to put pressure on the base part conventionally. Thus, this cylindrical bandage provides good fit and high compression and high return-promoting-effect. In a term of the return-promoting-effect, such good fit and high compression with 15 mmHg and more at the base part around the malleolus part near the heel side of the foot yields high return-promoting-effect. However, such high compression may cause, for example, skin damage, skin laceration, or skin tear depending on conditions of a wear part (diseased part) of a wearer. Thus, the compression that is within a range from 3 to 70 mmHg at the base part around the lateral malleolus part near the heel side of the foot causes less or no skin damage, skin laceration, and skin tear and yields the return-promoting-effect in a lower extremity in addition to the advantages recited in one of claims 1-7. This compression is, preferably, within a range from 15 to 50 mmHg, more preferably, 20 to 45 mmHg. This yields good comfort and higher return-promoting-effect and high mitigation effect for edemas at the circumference of the ankle joint, specifically, the malleolus part and the rear side of the ankle, where the lymph is easily collected.

A cylindrical bandage of the present invention claimed in claim 9 provides a difference in compression that is 40% or less between a base part around a lateral malleolus part near a heel side of the foot and an instep part of the foot while the cylindrical bandage is worn on a circumference of an ankle joint of the human body.

The cylindrical bandage of the present invention claimed in claim 8 is prevented from having wrinkles and tightness (tension) in the knit at the circumference of the ankle joint of the human body and thus its knit can fit and be in close contact with the circumference of the ankle joint of the human body. This enables the cylindrical bandage to provide 15 mmHg and more compression at the circumference of the malleolus, specifically, a base part that is around the malleolus part and near heel side of the foot, where it is difficult to put pressure on the base part conventionally. Thus, this cylindrical bandage provides good fit and high compression. This allows the cylindrical bandage to provide the difference in the compression that is 40% or less between the instep part of the foot and the base part that is around the malleolus part and is near the heel side of the foot. Thus, this cylindrical bandage provides the difference in the compression that is 40% or less between the base part being malleolus part near heel side of the foot and the instep part of the foot. This yields high compression at the circumference of the malleolus part, where lymph is easily collected, and yields steady compression-distribution and prevention of concentration of the compression and thus uniform compression at the circumference of the ankle joint. This causes high return-promoting-effect in a lower extremity and high mitigation effect for edemas at the circumference of the ankle joint, specifically, the malleolus part and the rear side of the ankle, where lymph is easily collected, in addition to the advantages recited in one of claims 1-8. The difference in the compression between a base part of the lateral malleolus part near the heel side of the foot and an instep part of the foot is, preferably, 30% or less, more preferably, 10% or less. This yields steadier compression and much higher return-promoting-effect.

A cylindrical bandage of the present invention claimed in claim 10 has a larger diameter of a circle, or a circumference, on a wale side at an endmost part of a second tubular knit than a diameter of a circle at an endmost part of a first tubular knit. The endmost part of the second tubular knit follows the first tubular knit. The endmost part of the first tubular knit follows the second tubular knit. Additionally, the cylindrical bandage has the connecting knit that connects the first tubular knit and the second tubular knit by increase in the number of the stitches on a course side between the first tubular knit and the second tubular knit. Thus, the connecting knit includes curvature. Consequently, the cylindrical bandage fits the shape of a heel having a bulge and is prevented from having tightness at the heel side while the cylindrical bandage is worn and covers, for example, on a circumference of an ankle joint. In a connection part between the first tubular knit and the second tubular knit, the second tubular knit has larger diameter than the first tubular knit. Thus, the connection part has variation in the diameter between the first tubular knit and the second tubular knit. This allows the connecting knit connecting the first tubular knit and the second tubular knit to have sufficient big curvature to correspond to the bulge of the heel, enabling the cylindrical bandage to have little or no tightness while the cylindrical bandage is worn. Since the second tubular knit has larger diameter than the first tubular knit in connection between the first tubular knit and the second tubular knit, there is wide selection for the diameter. This allows design and select of the best diameter corresponding to dimensions and shapes that have a lot of variation in section, such as the circumference of the ankle joint. Thus, the cylindrical bandage is prevented from having slack and wrinkles at an instep side of the foot and prevented from having excessive tension at the heel side while the cylindrical bandage is worn.

In a state where the cylindrical bandage is folded along a symmetrical line of the first tubular knit and the second tubular knit, the length (a) of a virtual perpendicular line, which runs from a border between the first tubular knit, the second tubular knit, and the connecting knit to the symmetrical line where the first tubular knit is followed by the second tubular knit, and a length (b) of a virtual perpendicular line, which runs from the border to the symmetrical line of the connecting knit side, are in the ratio 6:4≤(a):(b)≤9:1. Thus, the first tubular knit and the second tubular knit, which have no curvature and no bulge, cover on an irregular shape around a malleolus. The connecting knit, which is between the first tubular knit and the second tubular knit and has the curvature, fails to cover the irregular shape around the malleolus.

Thus, the cylindrical bandage is prevented from having slack and wrinkles at the instep of the foot and tightness at the heel side while being worn. The first tubular knit and the second tubular knit fail to rise at even the irregular shape around the malleolus and are in close contact with the circumference of the malleolus. Thus, the cylindrical bandage can put uniform pressure on the circumference of the ankle joint.

That is, the cylindrical bandage is a good fit for a wear part including a lot of variation in dimensions and shapes in the section, such as the circumference of the ankle joint, and provides steady compression. This yields high return-promoting-effect.

A cylindrical bandage of the present invention claimed in claim 11 has the connecting knit that follows a range of 10 to 40% of the circumference of the circle on the wale side at the endmost part of the first tubular knit. The endmost part of the first tubular knit follows the second tubular knit and the connecting knit. At the same time, the connecting knit follows a range of 10 to 40% of circumference of the circle on the wale side at the endmost part of the second tubular knit. The endmost part of the second tubular knit follows the first tubular knit and the connecting knit. Thus, the first tubular knit and the second tubular knit 20 are prevented from being pulled to the heel side while the cylindrical bandage is worn and covers, for example, on an ankle joint of a foot, in addition to the advantages recited in claim 10. Consequently, the first tubular knit and the second tubular knit, which cover dimensions and shapes including a lot of variation in section, such as an irregular part around the malleolus, are prevented from rising with tightness. Thus, the first tubular knit and the second tubular knit are in closer contact with the dimensions and shapes including a lot of variation in section, such as around the malleolus.

In a cylindrical bandage of the present invention claimed in claim 12, both a thickness of the first tubular knit and a thickness of a second tubular knit are within a range of 2 to 15 mm. Thus, it is difficult for the knit to have wrinkles. In particular, it is difficult for even the knit at the part having movement such as bending, for example, the knit at an instep side of the foot, to create wrinkles while the cylindrical bandage is worn. This cylindrical bandage is prevented from providing a concentration of the compression and tourniquet action with wrinkles cutting into the skin in addition to the advantages recited in one of claim 10 or claim 11.

A cylindrical bandage of the present invention claimed in claim 13 provides compression that is within a range from 3 to 70 mmHg at a base part around a lateral malleolus part near a heel side of the foot while being worn on a circumference of an ankle joint of the human body.

If this compression is less than 3 mmHg, the cylindrical bandage fails to provide return-promoting-effect. If this compression is greater than 70 mmHg, the cylindrical bandage prevents the return-promoting conversely.

The cylindrical bandage of the present invention claimed in claim 8 is prevented from having wrinkles and tightness (tension) in the knit at the circumference of the ankle joint of the human body and thus its knit can fit and be in close contact with the circumference of the ankle joint of the human body. This enables the cylindrical bandage to provide 15 mmHg and more compression at the circumference of the malleolus, specifically, a base part that is around the malleolus part and near heel side of the foot, where it is difficult to be put pressure on the base part conventionally. Thus, this cylindrical bandage provides good fit and high compression and high return-promoting-effect. In a term of the return-promoting-effect, such good fit and high compression with 15 mmHg and more at the base part around the malleolus part near the heel side of the foot yields high return-promoting-effect. However, such high compression may cause, for example, skin damage, skin laceration, or skin tear depending on conditions of a wear part (diseased part) of a wearer. Thus, the compression that is within a range from 3 to 70 mmHg at the base part around the lateral malleolus part near the heel side of the foot causes less or no skin damage, skin laceration, and skin tear and yields the return-promoting-effect in a lower extremity in addition to the advantages recited in one of claims 10-12. This compression is, preferably, within a range from 15 to 50 mmHg, more preferably, 20 to 45 mmHg. This yields good comfort and higher return-promoting-effect and high mitigation effect for edemas at the circumference of the ankle joint, specifically, the malleolus part and the rear side of the ankle, where the lymph is easily collected.

A cylindrical bandage of the present invention claimed in claim 14 provides a difference in compression that is 40% or less between a base part around a lateral malleolus part near a heel side of the foot and an instep part of the foot while the cylindrical bandage is worn on a circumference of an ankle joint of the human body.

The cylindrical bandage of the present invention claimed in claim 8 is prevented from having wrinkles and tightness (tension) in the knit at the circumference of the ankle joint of the human body and thus its knit can fit and be in close contact with the circumference of the ankle joint of the human body. This enables the cylindrical bandage to provide 15 mmHg and more compression at the circumference of the malleolus, specifically, a base part that is around the malleolus part and near heel side of the foot, where it is difficult to be put pressure on the base part conventionally. Thus, this cylindrical bandage provides good fit and high compression. This allows the cylindrical bandage to provide the difference in the compression that is 40% or less between the instep part of the foot and the base part that is around the malleolus part and is near heel side of the foot. Thus, this cylindrical bandage provides the difference in the compression that is 40% or less between the base part being malleolus part near heel side of the foot and the instep part of the foot. This yields high compression at the circumference of the malleolus part, where lymph is easily collected, and yields steady compression-distribution and prevention of concentration of the compression and thus uniform compression at the circumference of the ankle joint. This causes high return-promoting-effect in a lower extremity and high mitigation effect for edemas at the circumference of the ankle joint, specifically, the malleolus part and the rear side of the ankle, where lymph is easily collected, in addition to the advantages recited in one of claims 10-13. The difference in the compression between a base part of the lateral malleolus part near the heel side of the foot and an instep part of the foot is, preferably, 30% or less, more preferably, 10% or less. This yields steadier compression and much higher return-promoting-effect.

BRIEF DESCRIPTION OF THE DRAWINGS

FIG. 6 is a plain view (elevation view) of the cylindrical bandage in accordance with the embodiment of the present invention. This is view from the front in a state in which the cylindrical bandage is fold so that its front and rear face each other, when a knee side of a leg and an instep side of a foot are defined as the front, and a calf side of the leg and a heel of the foot is defined as the rear while the cylindrical bandage is worn.

FIG. 7 is a plain view (rear view) of the cylindrical bandage in accordance with the embodiment of the present invention. This is view from the rear in a state in which the cylindrical bandage is fold so that its front side and rear side face each other. The front is the knee side of the leg and the instep of the foot and the rear is the calf side of the leg and the heel of the foot is defined as while the cylindrical bandage is worn.

FIG. 10A is a main enlarged view illustrating the knitting of the knit. FIG. 10A is a schematic view illustrating knitting course.

Specifically, this FIG. 14A is a photo of the cylindrical bandage of the embodiment when viewed from instep side of the foot and side of the foot. FIG. 14B is a photo of the cylindrical bandage of the embodiment when viewed from ankle side of the foot.

DESCRIPTION OF THE EMBODIMENTS

Figure 1A:
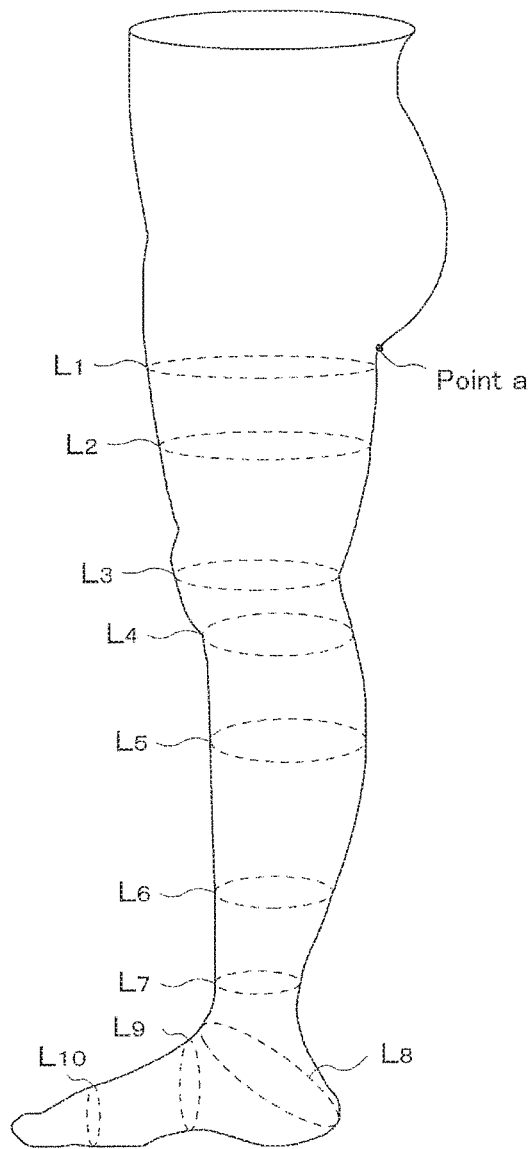
FIG. 1A is a measurement list of the human body that is used for determination of shapes of a cylindrical bandage in accordance with an embodiment of the present invention.

A preferred embodiment of the present invention is described hereafter by referring to drawings. In the embodiment, a same mark and a same code show in the drawings mean the same or equivalent function parts and thus overlapped explanation thereof is omitted below.

Embodiment

A structure of a cylindrical bandage of the embodiment of the present invention is first described by referring to mainly FIG. 1 to FIG. 9 and FIG. 14. In the embodiment, the cylindrical bandage is worn a lower extremity (a leg part and a foot part) of a human body, which is described as an example of an object of an wear.

A cylindrical bandage 1 of the embodiment is a tubular knit opening through the both ends of the longitudinal direction. The cylindrical bandage 1 is used as supporter for the lower extremity (a long supporter), which is worn on the lower extremity of a human body along its lengthwise direction, and covers a range from the foot part excluding toes to a thigh of the leg part while being worn. This supporter for the lower extremity as the cylindrical bandage 1 may be used with a couple of legs, a right leg and a left leg. Alternatively, the supporter for the lower extremity may be used alone. The supporter for the lower extremity is used for both legs without distinction of the right leg or the left leg.

The cylindrical bandage 1 of the embodiment includes a first tubular knit 10 that covers a leg side of the human body, a second tubular knit 20 that follows the first cylindrical bandage 10 and covers a foot side of the human body, and a connecting tubular knit 30 that connects the tubular knit 10 and the second tubular knit 20 to correspond to a heel shape of the human body and covers the heel side of the foot.

In the cylindrical bandage 1 of the embodiment, the first tubular knit 10 and the second tubular knit 20 following it are formed by using human body position dates $L_1, L_2, L_3, \ldots$ that corresponds to the lengthwise direction of the human body and human body circumference dates $m_1, m_2, m_3, \ldots$, which are circumference of a section being perpendicular with respect to the human body position dates $L_1, L_2, L_3, \ldots$.

Figure 1B:
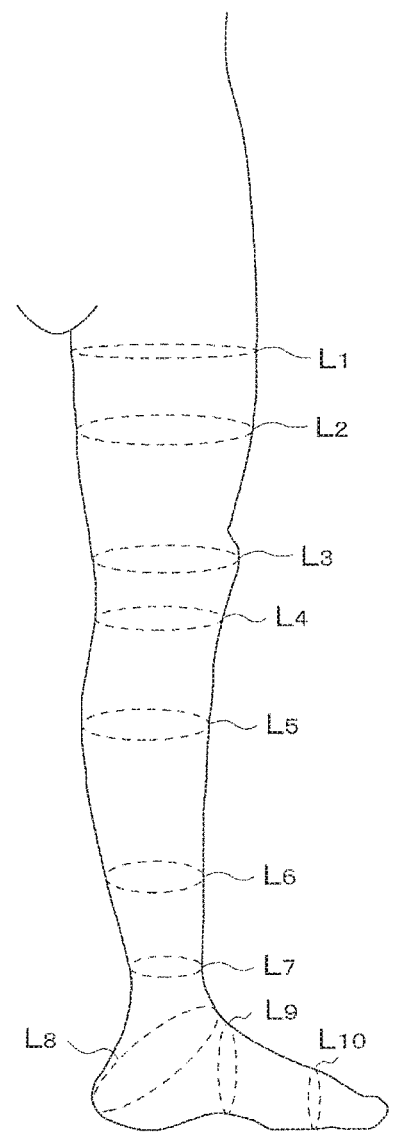
FIG. 1B is a measurement list of the human body that is used for determination of the shapes of the cylindrical bandage in accordance with the embodiment of the present invention.
Figure 1C:
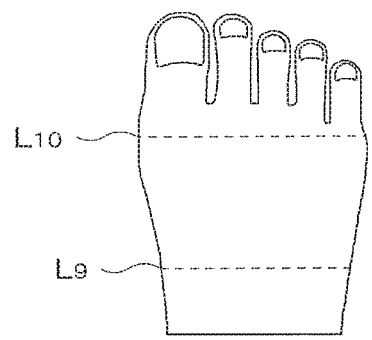
FIG. 1C is a measurement list of the human body that is used for determination of the shapes of the cylindrical bandage in accordance with the embodiment of the present invention.

In some embodiments, the human body position dates $L_1, L_2, L_3, \ldots$ are the predetermined positions where measurement is taken, for example, as shown in following TABLE 1 and FIG. 1. Thus, a purpose of the cylindrical bandage 1 (for example, the cylindrical bandage 1 is used for the prevention or the treatment for the lymphedema or the varicose vein in the lower extremity), a kind of the cylindrical bandage (for example, the cylindrical bandage 1 is used as a supporter, a sleeve, a stocking, a glove, an underwear), or a wear part, such as an arm, a leg, a head, a foot, a hand, and a wrist, which the cylindrical bandage 1 is worn on and which is under pressure from the outside, are used to determine measurement positions. The measurement is taken around this position.

Thus, the position as the human body position dates $L_1, L_2, L_3, \ldots$ is determined and the circumference of such determined position as the human body position dates $L_1, L_2, L_3, \ldots$ is measured. This circumference is the circumference of the section being perpendicular with respect to the human body position dates $L_1, L_2, L_3, \ldots$. Variation in the human body circumference dates $m_1, m_2, m_3, \ldots$, for example, which is the circumference of a thickness of the leg or the arm, corresponds to variation in the position in the lengthwise direction of the human body, or the variation in the human body position dates $L_1, L_2, L_3, \ldots$.

The measurement point as the human body position dates $L_1, L_2, L_3, \ldots$ is commonly set at the part including variation in shapes of the human body or near this part.

The cylindrical bandage 1 (the supporter for the lower extremity), which is worn over a range from the foot excluding the toe to the thigh of the leg, of the embodiment uses the measurement of a range from the position $L_1$, which is the position of the groin, to the position $L_{10}$, which is the base of the little toe, as shown in FIG. 1.

This FIG. 1 shows the relationship between the human body position dates $L_1, L_2, L_3, \ldots, L_9, L_{10}$, which is measurement points of the part of the foot and the leg of the human body that is the object of wear of the cylindrical bandage 1 of the embodiment.

TABLE 1 shows the date of the embodiment for knitting the first tubular knit 10 and the second tubular knit 20. This TABLE 1 shows the measured values that shows the relationship of the human body circumference dates $m_1, m_2, m_3, \ldots m_9, m_{10}$, corresponding one-to-one to the human body position dates $L_1, L_2, L_3, \ldots, L_9, L_{10}$. Such human body position dates $L_1, L_2, L_3, \ldots, L_9, L_{10}$ correspond to the length of the leg (inside leg) and the length of the foot excluding the toe of the human body and such human body circumference dates $m_1, m_2, m_3, \ldots m_9, m_{10}$ are the circumference of the section being perpendicular with respect to the human body position dates $L_1, L_2, L_3, \ldots, L_9, L_{10}$. These dates shown in TABLE 1 are the measured values of the circumference of the section of the human body. These dates have directly no relationship to elasticity.

TABLE 1

| | human body position dates | | | | | | | | | |
|---|---|---|---|---|---|---|---|---|---|---|
| | $L_1$ | $L_2$ | $L_3$ | $L_4$ | $L_5$ | $L_6$ | $L_7$ | $L_8$ | $L_9$ | $L_{10}$ |
| human body circumference dates | $m_1$ 52 | $m_2$ 47 | $m_3$ 36 | $m_4$ 34 | $m_5$ 35 | $m_6$ 28 | $m_7$ 22 | $m_8$ 30 | $m_9$ 22 | $m_{10}$ 22 |

As shown in FIG. 1, the numerical value of the embodiment in TABLE 1 shows that the human body circumference date $m_1$ is 52 cm. This human body circumference date $m_1$ is the circumference of the section at the position $L_1$ that is under 5 cm from the point a, which is the end position of the bulge in the hip of the human body, that is, the circumference of the section being perpendicular with respect to the human body position date $L_1$.

The numerical value of the embodiment in TABLE 1 shows that the human body circumference date $m_2$ is 47 cm. This human body circumference date $m_2$ is the circumference of the section at the position $L_2$ that is the middle position located between the point a and position $L_3$, which is the bending part of the knee, that is, the circumference of the section being perpendicular with respect to the human body position date $L_2$.

The numerical value of the embodiment in TABLE 1 shows that human body circumference date $m_3$ is 36 cm. This human body circumference date $m_3$ is the circumference of the section at the position $L_3$ that is the bending part of the knee, that is, the circumference of the section being perpendicular with respect to the human body position date $L_3$.

The numerical value of the embodiment in TABLE 1 shows that human body circumference date $m_4$ is 34 cm. This human body circumference date $m_3$ is the circumference of the section at the position $L_4$ that is the position of the fibular head, that is, the circumference of the section being perpendicular with respect to the human body position date $L_4$.

The numerical value of the embodiment in TABLE 1 shows that human body circumference date $m_5$ is 35 cm. This human body circumference date $m_5$ is the circumference of the section at the position $L_5$ that is thickest point in the carf, that is, the circumference of the section being perpendicular with respect to the human body position date $L_5$.

The numerical value of the embodiment in TABLE 1 shows that human body circumference date $m_6$ is 28 cm. This human body circumference date $m_5$ is the circumference of the section at the position $L_6$ that is starting point of the carf, that is, the circumference of the section being perpendicular with respect to the human body position date LG.

The numerical value of the embodiment in TABLE 1 shows that human body circumference date $m_7$ is 22 cm. This human body circumference date $m_5$ is the circumference of the section at the position $L_7$ that is thinnest point in the ankle, that is, the circumference of the section being perpendicular with respect to the human body position date $L_7$.

The numerical value of the embodiment in TABLE 1 shows that human body circumference date $m_8$ is 30 cm. This human body circumference date $m_5$ is the circumference of the section at the position $L_8$ that is the position over a range of the instep to the heel, that is, the circumference of the section being perpendicular with respect to the human body position date $L_8$.

The numerical value of the embodiment in TABLE 1 shows that human body circumference date $m_9$ is 22 cm. This human body circumference date $m_5$ is the circumference of the section at the position $L_9$ that is the position of the arch of the foot, that is, the circumference of the section being perpendicular with respect to the human body position date $L_9$.

The numerical value of the embodiment in TABLE 1 shows that human body circumference date $m_{10}$ is 22 cm. This human body circumference date $m_5$ is the circumference of the section at the position $L_{10}$ that is the base of the little toe, that is, the circumference of the section being perpendicular with respect to the human body position date $L_{10}$.

These numerical values of the embodiment shown in TABLE 1 are measurement dates of patients with lymphedema in the lower extremity. In some embodiments, the dates may be measured by millimeter.

Thus, the embodiment obtains the relationship between the human body position dates $L_1, L_2, L_3, \ldots$, and the human body circumference dates $m_1, m_2, m_3, \ldots$, which determine one-unit-length of a stitch row on one circle where a yarn continues in the widthwise direction. This stitch row on one circle where a yarn continues in the widthwise direction may be called "wale side" below. The loop-column lined up in the lengthwise direction of the knit is called the course side. The loop-row placed in the row in the widthwise direction of the knit is called the wale side. The course side shows the number of stitches counted in the lengthwise direction (Y axial direction in the X-Y axis). The wale side shows the number of stitches, or, needles and gauges, in the widthwise direction (X axial direction in the X-Y axis), which is perpendicular direction to the course direction. The loop-column lined up in the lengthwise direction (y direction) of the knit, or the stitches of the lengthwise direction where the yarn is interknitted into loop shapes (annual shapes), is the course. The loop-row placed in the row in the widthwise direction (x direction) of the knit, or the stitches where the yarn continues in the widthwise direction, is the wale. Thus, the course and the wale are distinguished.

In both the first tubular knit 10 and the second tubular knit 20 in accordance with the cylindrical bandage 1 of the embodiment, the stitch row on the wale side is set to the number of the stitches (the number of the loops, the number of the needles) that approximates calculated the number of the stitches derived by using the human body circumference dates $m_1, m_2, m_3, \ldots$, which is in the section being perpendicular to the human body position dates $L_1, L_2, L_3, \ldots$, and the predetermined young's modulus, in which positions or parts in the human body such as the body position dates $L_1, L_2, L_3, \ldots$, is reflected.

In other words, variation in circumference, or difference in circumference, between human body circumference dates in the human body circumference dates $m_1, m_2, m_3, \ldots$, which are the circumference of the section being perpendicular with respect to the human body position dates $L_1, L_2, L_3, \ldots$, are expressed as difference in the number of the stitches of the row on the wale side.

In detail, the human body position dates $L_1, L_2, L_3, \ldots$ are determined by reflecting the wear part, use, or the like. Thus, the human body circumference dates $m_1, m_2, m_3, \ldots$ are measured at such human body position dates $L_1, L_2, L_3, \ldots$ as dates to determine the length of the stitch row on the one circle of the wale side in the first tubular knit 10 and the second tubular knit 20.

The human body position dates $L_1, L_2, L_3, \ldots$ and the human body circumference dates $m_1, m_2, m_3, \ldots$ are often provided by medical institutions, or the like. At first, such human body circumference dates $m_1, m_2, m_3, \ldots$ are dates of dimensions (cm, mm) of each part of the human body. Use of the human body position dates $L_1, L_2, L_3, \ldots$, which are in the length direction of a part of the human body, the object of the wear, and use of the human body circumference dates $m_1, m_2, m_3, \ldots$, which are the circumference of the section being perpendicular with respect to the human body position date $L_1, L_2, L_3, \ldots$, determine the measurement of the cylindrical bandage 1.

Although the human body circumference dates $m_1$, $m_2$, $m_3$, ..., which are on the section being perpendicular with respect to the human body position dates $L_1$, $L_2$, $L_3$, ..., are measured as original dimensions of the human body, this indicates the circumference of the section being perpendicular with respect to the human body position dates $L_1$, $L_2$, $L_3$, ....

The human body position dates $L_1$, $L_2$, $L_3$, ... are standards for the position of the cylindrical bandage 1 and the human body circumference dates $m_1$, $m_2$, $m_3$, ... are circumference dates that are standard to calculate and determine the number of the stitches of the stitch row on the wale side. These are original dates, no edited dates.

After obtaining the human body circumference dates $m_1$, $m_2$, $m_3$, ..., these dates are used to calculate and determine the number of the stitches that is derived from the calculation in a way that the predetermined young's modulus corresponding to the positions of the human body position dates $L_1$, $L_2$, $L_3$, ... is achieved. Although this calculation determines the number of the stitches, the unit after the decimal points in the number of the stitches may be rounded off, rounded down, or rounded up. Physical properties of the yarn, purpose of the cylindrical bandage 1, or other characteristics determines the selection of rounding off, rounding down, or rounding up.

The predetermined young's modulus, which the positions as the human body position dates $L_1$, $L_2$, $L_3$, ... are reflected, is determined by reflecting, for example, physical property of the yarn for knitting, means of knitting, a loop diameter, and density.

The positions as the human body position dates $L_1$, $L_2$, $L_3$, ... are reflected to determine the young's modulus. The stitch row on the one circle of the wale side is set to the number of the stitches, or needles, that approximates calculated the number of the stitches that is calculation based on the young's modulus and the human body circumference dates $m_1$, $m_2$, $m_3$, ....

Under conditions where, for example, a cross-section area formed of the stitches on the wale side (in the context of the physical properties of the yarn) is set to S, a force that is applied to such cross-section area formed of the stitches on the one circle is set to F, and an extension from original length P is set to $\Delta P$, the young's modulus (E) is shown in the following equation, $$E=(F/S)/(\Delta P/P)$$

The physical properties of the yarn, methods of the knit, or the like determines the cross-section area S formed of the stitches on the wale side. The force F applied to the cross-section area S formed of the stitches on the wale side (in the context of physical properties of spun yarn) is determined by reflecting the positions as the human body position dates $L_1$, $L_2$, $L_3$, .... When the force F applied to the cross-section area S formed of the stitches on the wale side (in the context of physical properties of spun yarn) is set to a uniform value in anywhere, F/S is the fixed value and the parameter. In this case, the young's modulus is set to fixed value between units in the human body position dates $L_1$, $L_2$, $L_3$, .... Thus, the external force fails to apply only a partial part in the length direction of the human body. The wearer is under uniform pressure and feels no strange. Conversely, the force F applied to the cross-section area S formed of the stitches on the wale side (in the context of physical properties of spun yarn) may vary to reflect the positions as the human body position dates $L_1$, $L_2$, $L_3$, .... Variation in the level of the external force to correspond to the part enables improvement of return-promoting-effect. For example, designing the cylindrical bandage 1 with gradually increase in compression from the ankle side to the thigh side allows improvement of return-promoting-effect while the cylindrical bandage 1 is worn.

Thus, the young's modulus is set to predetermined value corresponding to the positions of the human body position dates $L_1$, $L_2$, $L_3$, ..., calculating the number of the stitches on the wale side in accordance with variation in the cross-section or the circumference of the human body circumference dates $m_1$, $m_2$, $m_3$, .... The calculation using the human body circumference dates $m_1$, $m_2$, $m_3$, ..., which are on the section being perpendicular with respect to the human body position dates $L_1$, $L_2$, $L_3$, ... along the length direction of the part of the human body, shows the number of the stitches on the wale side. The number of the stitches of the stitch row on the wale side is calculated in a way that the predetermined young's modulus corresponding to the position of the human body position dates $L_1$, $L_2$, $L_3$, ... is achieved. At this point, the human body circumference dates $m_1$, $m_2$, $m_3$, ... are replaced with the number of the stitches on the wale side.

Thus, the first tubular knit 10 and the second tubular knit 20 in accordance with the cylindrical bandage 1 of the embodiment are knitted by using the human body position dates $L_1$, $L_2$, $L_3$, ..., which equalize with lengthwise direction of a part of the human body being the object of the wear, and the human body circumference dates $m_1$, $m_2$, $m_3$, ..., which are circumference of the section being perpendicular to the human body position dates $L_1$, $L_2$, $L_3$, .... The stitch row on the circle of the wale side in the first tubular knit 10 and the second tubular knit 20 is set to the number of the stitches that approximates the calculation based on the human body circumference dates $m_1$, $m_2$, $m_3$, ... and the predetermined young's modulus in which the positions as the human body position dates $L_1$, $L_2$, $L_3$, ... are reflected. In this way, the first tubular knit 10 and the second tubular knit 20 is knitted. Thus, variation in the human body circumference dates $m_1$, $m_2$, $m_3$, ... are expressed as difference in the number of the stitches.

In the embodiment, the human body circumference dates $m_1$, $m_2$, $m_3$, ... vary to adapt to the variation in the positions of the human body position dates $L_1$, $L_2$, $L_3$, ..., which correspond to the length of the leg and the length of the foot. In the first tubular knit 10 and the second tubular knit 20, the number of the stitches varies to adapt to the variation in the section of the wear part of the human body. Thus, the circumference on the wale side varies depending on the variation in the number of the stitches along the direction corresponding to the lengthwise direction of the human body.

The number of the stitches on the circle of the wale side in the first tubular knit 10 and the second tubular knit 20 in accordance with the cylindrical bandage 1 of the embodiment is set to approximation of the calculation based on the human body circumference dates $m_1$, $m_2$, $m_3$, ... corresponding to the human body position dates $L_1$, $L_2$, $L_3$, ... and the predetermined young's modulus in which the positions of the human body position dates $L_1$, $L_2$, $L_3$, ... are reflected. Variation in the number of the stitches and the knitting-width determine a shape of the total length.

In the cylindrical bandage 1 of the embodiment, the variation in the circumference with the variation in the number of the stitches allows adjustment of the compression. The cylindrical bandage 1 of the embodiment can provide predetermined compression corresponding to the variation in the section of the wear part. Such section varies along the lengthwise direction of the human body. Thus, it is easy to adjust desired compression corresponding to the positions of the human body position dates $L_1, L_2, L_3, \ldots$ and the variation in the section of the human body.

In addition to the variation in the number of the stitches, variation in loop diameter, density, means of knitting, or physical property of the yarn; young's modulus enables the variation in the compression. Such compression may be fixed or varied in the lengthwise direction.

The number of the stitches on the course side where the yarn is loop-interknitted is set on the basis of the distance between the human body position dates $L_1, L_2, L_3, \ldots$ by reflecting physical property of the yarn, means of knitting, or density.

As shown in the human body circumference date $m_8$, the region of the ankle, which is the border between the leg and the foot of the body, includes a lot of variation in the circumference of the cross-section with the heel and the malleolus. In particular, the patients with venous return failure, lymphedema, or other diseases have locally large circumference and a lot of variation in the circumference of the cross-section in the region of the ankle. That is, a range from the human body circumference date $m_7$, which corresponds to the human body position date $L_7$ that is the part of the ankle of the leg, to the human body circumference date $m_9$, which corresponds to the human body position date $L_9$ that is the part of the arch of the foot, has a lot of variation in the circumference of the cross-section.

Thus, the first tubular knit 10 and the second tubular knit 20 in the cylindrical bandage 1 of the embodiment have the variation in the circumference on the wale side with the variation in the number of the stitches. This first tubular knit 10 includes the number of the stitches that approximates the calculation based on the human body circumference dates $m_1, m_2, m_3, \ldots m_6, m_7$, which are the circumference in the section being perpendicular to the human body position dates $L_1, L_2, L_3, \ldots L_6, L_7$, and the predetermined young's modulus, in which the positions of the human body position dates $L_1, L_2, L_3, \ldots L_6, L_7$ are reflected. This number of the stitches is set as the stitch row on the one circle in the wale side. The second tubular knit 20 includes the number of the stitches that approximates the calculation based on the human body circumference dates $m_9, m_{10}$, which are the circumference in the section being perpendicular to the human body position dates $L_9, L_{10}$, and the predetermined young's modulus, in which the positions of the human body position dates $L_1, L_2, L_3, \ldots$ are reflected. This number of the stitches is also set as the stitch row on the one circle in the wale side.

Between the end part of the first tubular knit 10 and the end part of the second tubular knit 20, where the first tubular knit 10 and the second tubular knit 20 are connected, the stitch forming the stitch row on the one circle of the end part (top end part) of the second tubular knit 20 outnumbers the stitch of the endmost part (bottom end part) forming the stitch row on the one circle of the first tubular knit 10. Thus, a knitting-width $I_2$ of topmost of the second tubular knit 20, which follows the bottom of the first tubular knit 10, is wider than a knitting-width $I_1$ of bottommost of the first tubular knit 10 (referring to FIG. 12).

Figure 12:
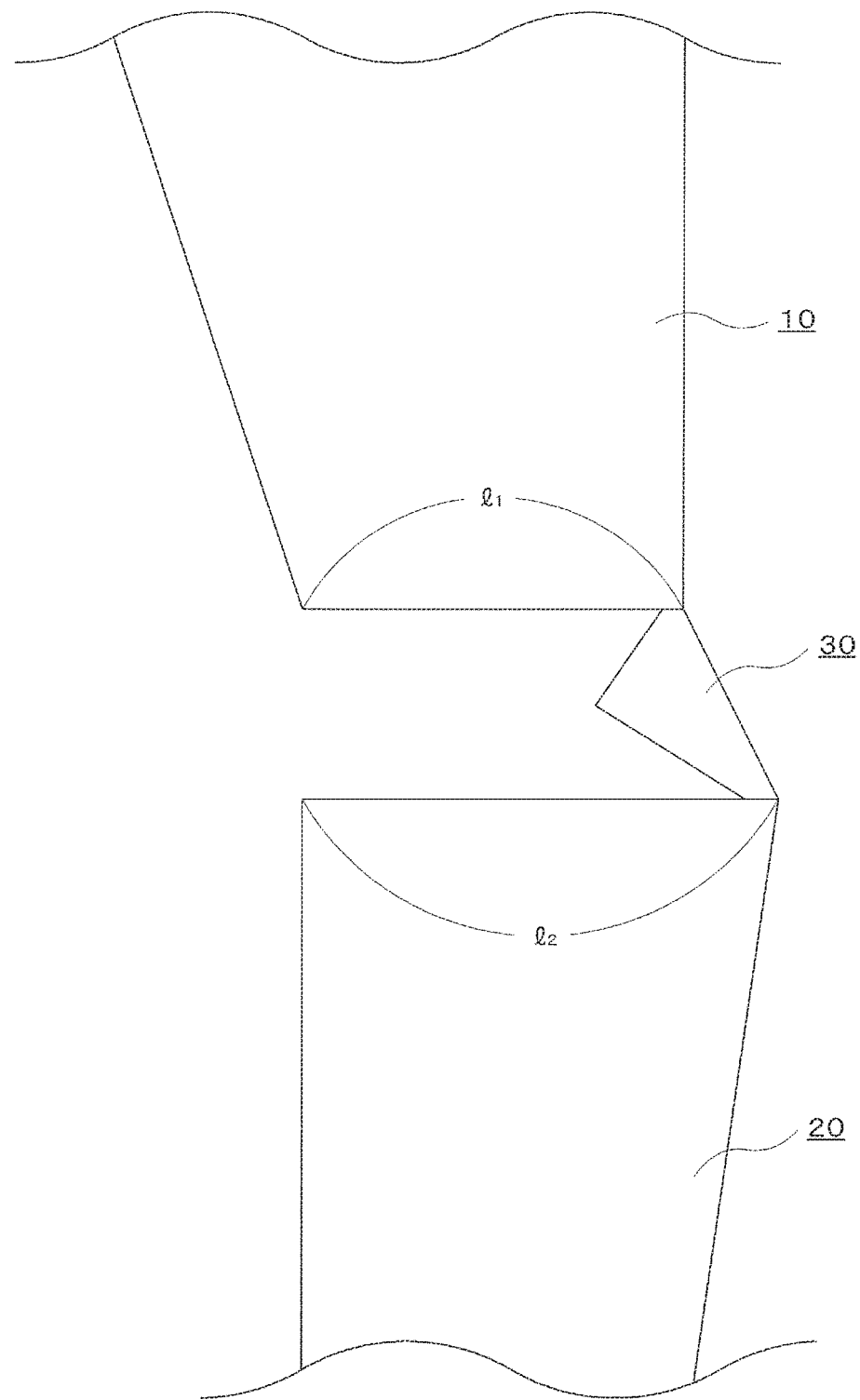
FIG. 12 is knitting course diagram illustrating a basic action of the knitting of a connecting knit of the cylindrical bandage in accordance with the embodiment of the present invention.

This variation in the number of the stitches allows the diameter and circumference of the circle, which is formed of the stitch row on the one circle of the wale side, of the top end of the second tubular knit 20 following the bottom end of the first tubular knit 10 to be wider or lager than the diameter and circumference, which is formed of the stitch row on the one circle of the wale side, of the bottom end of the first tubular knit 10 (referring to FIG. 12).

A connecting knit 30 is formed by increasing the number of the stitches of the course side, where the yarn is loop-interknitted, between the part of the stitch row on the one circle of the wale side of the endmost part (bottom end part) of the first tubular knit 10 and the part of the stitch row on the one circle of the wale side of the endmost part (top end part) of the second tubular knit 20, this endmost part (top end part) of the second tubular knit 20 has larger diameter than the endmost part (bottom end part) of the first tubular knit 10 one. Thus, the connecting knit 30 connects the part of the circle on the wale side of the endmost part (bottom end part) of the first tubular knit 10 and the part of the circle on the wale side of the endmost part (top end part) of the second tubular knit 20, this endmost part (top end part) of the second tubular knit 20 has larger diameter than the endmost part (bottom end part) of the first tubular knit 10 one.

In the connection of the course side at the ankle region, which is the border between the leg part and the foot part, if the first tubular knit 10 and the second tubular knit 20 are connected sharply by increasing the number of the stitches of the stitch row of the one circle on the wale side dramatically, which causes the course to have a short length, the first tubular knit 10 and the second tubular knit 20 rise to the surface with ruggedness at the rear side of the ankle and have excessive tension at a corner part or bent part of the heel while the cylindrical bandage 1 is worn on the leg of the foot of the human body, which is the object of the wear. Thus, it is difficult for the knit to be prevented from rising to the surface and to be close contact with and put pressure on the depression part of unevenness in the malleolus of the foot of the human body. Conversely, if the first tubular knit 10 and the second tubular knit 20 are connected gently by increasing the number of the stitches of stitch row of the one circle on the wale side gradually, a length of course is long between the first tubular knit 10 and the second tubular knit 20 and this causes the knit to have unfit diameter of the tube at the circumference of the ankle joint with wearing. Consequently, the knit has some slack and wrinkles and concentration of the compression with the wrinkles cutting into the skin.

In the cylindrical bandage 1 of the embodiment, a part of the second tubular knit 20 directly follows a part of the first tubular knit 10. A part of the stitch row on the one circle of the wale side of the endmost part (top end part) of the second tubular knit 20 follows a part of the stitch row on the one circle of the wale side of the endmost part (bottom end part) of the first tubular knit 10. The connecting knit 30 connects the rest of the stitch row on the one circle of the wale side of the endmost part (bottom end part) of the first tubular knit 10 and the rest of the stitch row on the one circle of the wale side of the endmost part (top end part) of the second tubular knit 20. The connecting knit 30 absorbs the difference of the diameter of the circle or circumference on the wale side between the bottom part of the first tubular knit 10 and top part of the second tubular knit 20.

This structure allows the knit to be prevented from rising to the surface at the rear side of the ankle, be prevented from having tightness at the corner part or bending part of the heel, and prevented from having wrinkles and slack, thus enabling the knit to fit the circumference of the ankle joint further.

In some embodiments, the second tubular knit 20 can be knitted by using the human body circumference date $m_8$, which are the circumference including the instep and the heel. Thus, the stitch row on the one circle of the wale side in the second tubular knit 20 can be set to the number of the stitches that approximates the calculation derived by using the human body circumference dates $m_8$, $m_9$, $m_{10}$, which are the circumference of the section being perpendicular to the human body position dates $L_8$, $L_9$, $L_{10}$, and using the predetermined young's modulus in which the positions as the human body position dates $L_8$, $L_9$, $L_{10}$ are reflected. In this case, the connecting knit 30 connects a part of the stitch row on the one circle of the wale side of the unit that corresponds to the human body circumference date $m_7$ of the second tubular knit 20 and a part of the stitch row on the one circle of the wale side of the unit that corresponds to the human body circumference date $m_8$ of the second tubular knit 20. Thus, the stitch row on the one circle of the wale side are set to the number of the stitches that approximates the calculation based on the human body circumference dates $m_8$, $m_9$, $m_{10}$, and the predetermined young's modulus in which the human body position dates $L_8$, $L_9$, $L_{10}$ are reflected. This yields the difference in the number of the stitches between the stitch row on the one circle of the wale side of the end of the unit that corresponds to the human body circumference date $m_7$ of the first tubular knit 10 and the stitch row on the one circle of the wale side of the end of the unit that corresponds to the human body circumference date $m_8$ of the second tubular knit 20. The number of the stitches increases in a range from the human body circumference date $m_7$, which corresponds to the human body position date $L_7$ of the ankle region being the border between the leg part and the foot part, to the human body circumference date $m_8$, which corresponds to the human body position date $L_8$. Thus, the knitting-width 12 of topmost of the second tubular knit 20, which follows the bottom of the first tubular knit 10, is wider than the knitting-width $l_1$ of bottommost of the first tubular knit 10. The diameter of the circle and the circumference of the wale side of the top end of the second tubular knit 20, which follows the bottom end of the first tubular knit 10, is wider or larger than the diameter of the circle and the circumference of the wale side of the bottom end of the first tubular knit 10.

Thus, in the first tubular knit 10 and the second tubular knit 20 of the embodiment, the variation in the number of the stitches reflects the variation in the human body circumference date $m_1$, $m_2$, $m_3$, ... $m_9$, $m_{10}$, which correspond to the human body position dates $L_1$, $L_2$, $L_3$, ..., $L_9$, $L_{10}$.

The first tubular knit 10 that is knitted by using the human body position dates $L_1$, $L_2$, $L_3$, ... $L_6$, $L_7$ and the human body circumference dates $m_1$, $m_2$, $m_3$, ... $m_6$, $m_7$, which correspond to the human body position dates $L_1$, $L_2$, $L_3$, ..., $L_9$, $L_{10}$, is mainly worn on the leg side. When the numerical value of the human body circumference dates $m_1$, $m_2$, $m_3$, ... $m_6$, $m_7$, decreases in order from the thigh side to the ankle side in the lengthwise direction of the leg of the human body, the number of the stitches decreases in accordance with the decrease of the numerical value in the human body circumference dates $m_1$, $m_2$, $m_3$, ... $m_6$, $m_7$. In this case, the difference in the number of the stitches with the difference in the human body position dates $L_1$, $L_2$, $L_3$, ... $L_6$, $L_7$ is set so as to gradually decrease between the human body position dates $L_1$, $L_2$, $L_3$, ... $L_6$, $L_7$ by knitting. This allows the cylindrical bandage 1 to provide steady compression and good wear feeling.

At the same time, the second tubular knit 20 that is knitted by using the human body position dates $L_8$, $L_9$, $L_{10}$ or $L_9$, $L_{10}$ and the human body circumference dates $m_8$, $m_9$, $m_{10}$ or $m_9$, $m_{10}$, which correspond one-to-one to the human body position dates $L_8$, $L_9$, $L_{10}$ or $L_9$, $L_{10}$ is mainly worn on the foot side. When the numerical value of the human body circumference dates $m_8$, $m_9$, $m_{10}$, or $m_9$, $m_{10}$ decreases in order from the ankle to the toes side in the lengthwise direction of the foot of the human body, the number of the stitches decreases in accordance with the decrease of the numerical value in the human body circumference dates $m_8$, $m_9$, $m_{10}$, or $m_9$, $m_{10}$. In this case, the difference in the number of the stitches with the difference between human body position dates $L_8$, $L_9$, $L_{10}$ or $L_9$, $L_{10}$ is set so as to gradually decrease between the human body position dates $L_8$, $L_9$, $L_{10}$ or $L_9$, $L_{10}$ by knitting. This allows the cylindrical bandage 1 to provide steady compression and good wear feeling.

An open side of the end part of the longitudinal direction of the cylindrical bandage 1 has less effect of its adjacent unit and is subject to resistance when the cylindrical bandage 1 is put on and taken off. In some cases, the number of the stitches is determined by reflecting decline in elasticity including fatigue by use.

In the cylindrical bandage 1 of the embodiment, the connecting knit 30 is knitted by increasing the number of stitches on the course side, where the yarn is looped-interknitted, between the first tubular knit 10 and the second tubular knit 20. The connecting knit 30 follows 40% or less of the circumference of the stitch row on the one circle of the wale side of the endmost part (bottom end part) of the first tubular knit 10 and 40% or less of the circumference of the stitch row on the one circle of the wale side of the endmost part (top end part) of the second tubular knit 20. At the same time, the following length in which the connecting knit 30 follows the stitch row on the one circle of the wale side of the endmost part (top end part) of the second tubular knit 20 is longer than the following length in which the connecting knit 30 follows the stitch row on the one circle of the wale side of the endmost part (bottom end part) of the first tubular knit 10.

It is preferable for the connecting knit 30 to follow 10% or more and 40% or less, more preferably, 20% or more and 40% or less of the knitting-width of the stitch row on the one circle of the wale side of the endmost part (bottom end part) in the first tubular knit 10. That is, this connecting knit 30 follows a part of the knitting-width of the endmost part (bottom end part) in the first tubular knit 10. At the same time, it is preferable for the connecting knit 30 to follow 10% or more and 40% or less, more preferably, 20% or more and 40% or less of the knitting-width of the stitch row on the one circle of the wale side of the endmost part (top end part) in the second tubular knit 20. That is, this connecting knit 30 follows a part of the knitting-width at the endmost part (top end part) in the second tubular knit 20. Thus, the connecting knit 30 interposes between the first tubular knit 10 and second tubular knit 20 and provides the predetermined angle between the first tubular knit 10 and the second.

Figure 2:
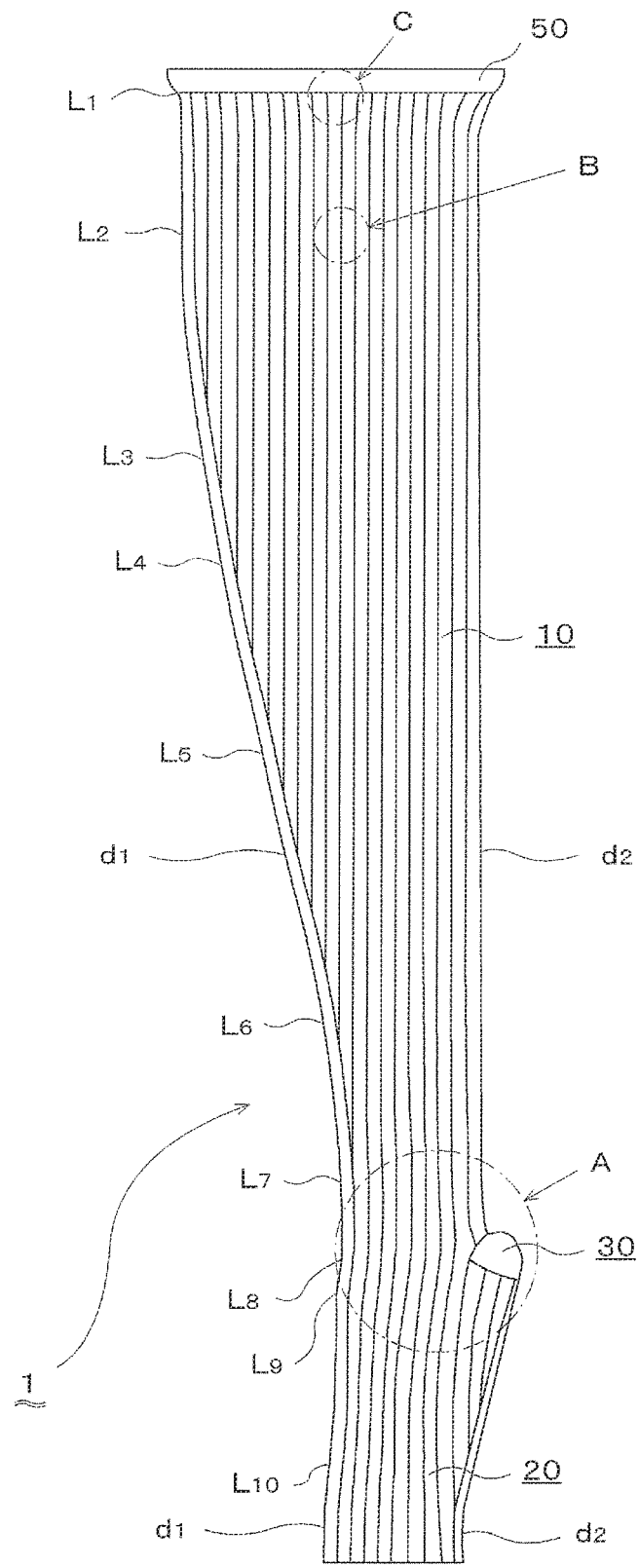
FIG. 2 is a plain view (side view) of the cylindrical bandage in accordance with the embodiment of the present invention when viewed from side in a state in which the cylindrical bandage is fold so that its left and right face each other. Such left and right is the side of the front and the rear, when a knee side of a leg and an instep side of a foot are defined as the front, and a calf side of the leg and a heel of the foot is defined as the rear while the cylindrical bandage is worn.
Figure 3A:
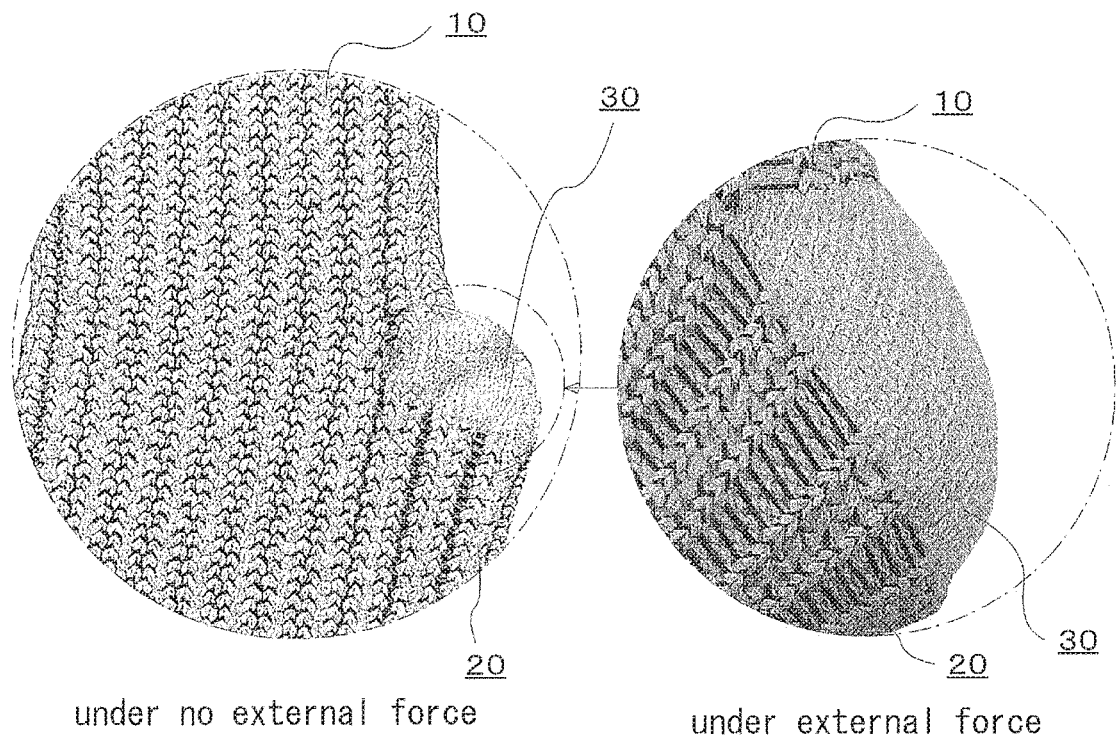
FIG. 3A is an enlarged view of a main part A shown in FIG. 2 and a photo of the cylindrical bandage of the embodiment.
Figure 3B:
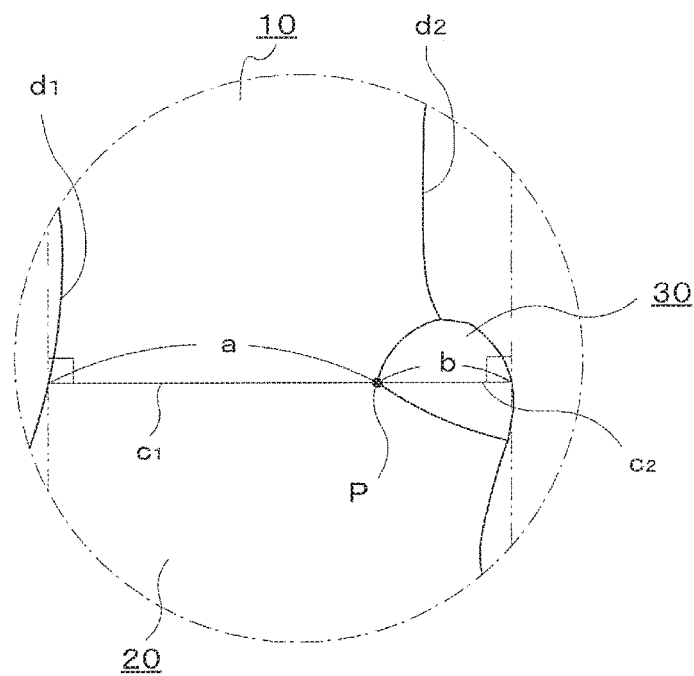
FIG. 3B is a schematic diagram illustrating the main part A shown in FIG. 2.

When an abdomen side of the human body is defined as the front, a back side of the human body is defined as the rear, and side view of the human body relative to this front and this rear is defined as the side while the cylindrical bandage 1 is worn, the cylindrical bandage 1 of the embodiment includes the right knit and the left knit that are symmetry as shown in a front view, FIG. 6 and a rear view, FIG. 7. When the cylindrical bandage 1 of the embodiment is folded such that its circumference of the stitch row on the one circle of the wale side is divided into half at a symmetrical line $d_1$ in a front side (the symmetrical line $d_1$ is shown as a centerline $d_1$ in the front view, FIG. 6) and a symmetrical line $d_2$ in the rear side (the symmetrical line $d_2$ is shown as a centerline $d_2$ in the rear view, FIG. 7) as shown in FIG. 2 and FIG. 3 and thus one of the insides of the tube touches the other opposite inside, the length a of the virtual perpendicular line $c_1$ (which is a perpendicular line $c_1$ that runs from a border P to an outline of the first tubular knit 10 and the second tubular knit 20 in FIG. 3) that runs from the border P between the first tubular knit 10, the second tubular knit 20, and the connecting knit 30 to the symmetrical line $d_1$ in the front side and the length b of the virtual perpendicular line $c_2$ (which is a perpendicular line $c_2$ that runs from the border P to the outline of the connecting knit 30 in FIG. 3) that runs from the border P to the symmetrical line $d_2$ in the rear side are in the ratio 6:4≤a:b≤9:1. These length a and the length b are measured under conditions where no external force is applied. When the lengthwise direction of the cylindrical bandage 1 is defined as vertical direction, the virtual perpendicular line $c_1$ and the virtual perpendicular line $c_2$ are perpendicular with respect to this vertical direction.

Figure 8A:
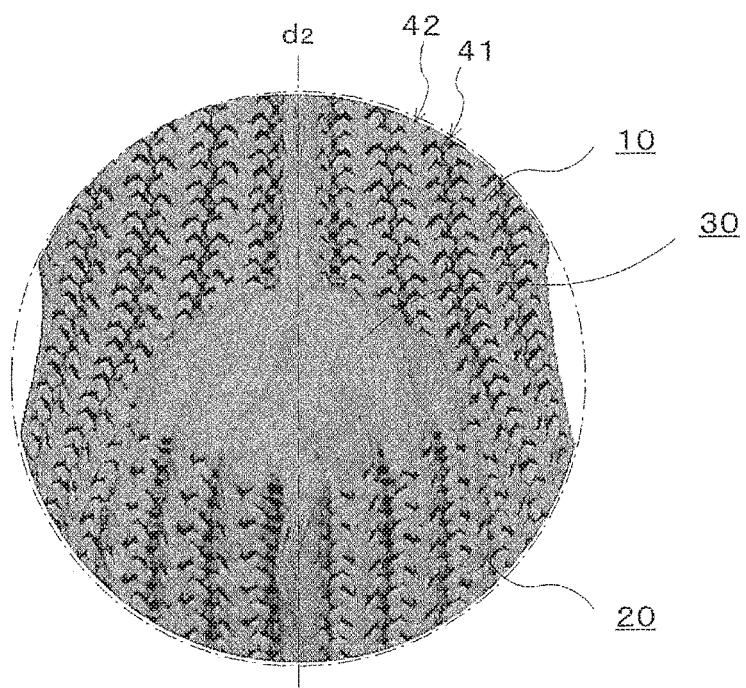
FIG. 8A is an enlarged view of a main part D shown in FIG. 7 and a photo of the cylindrical bandage of the embodiment.
Figure 8B:
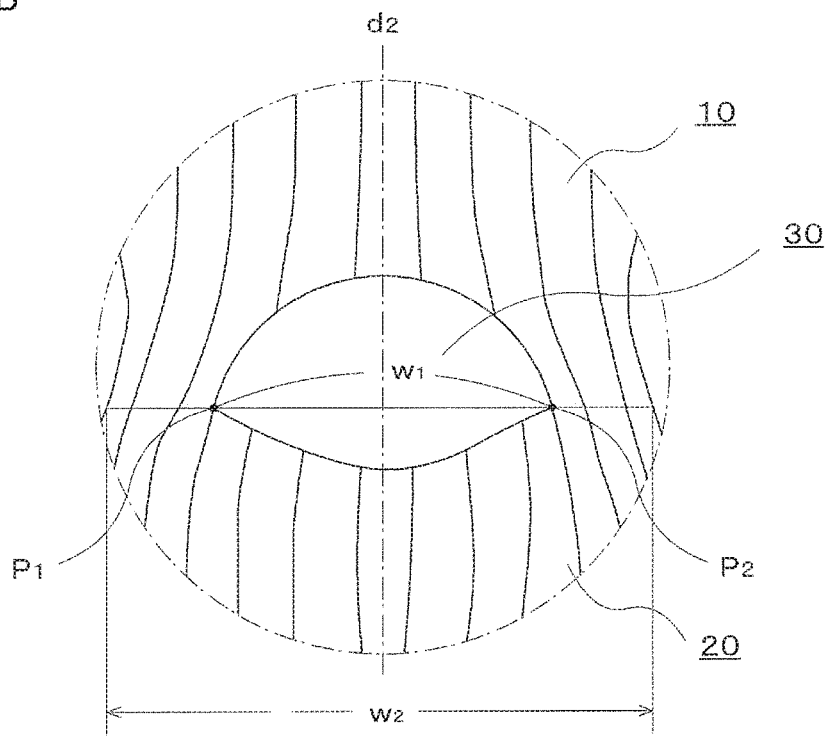
FIG. 8B is a schematic view illustrating the main part C shown in FIG. 7.

For the cylindrical bandage 1 is viewed from other angle as shown in the rear view FIG. 7 and FIG. 8, the length $w_1$ is within a range of 10 to 90%, preferably, 20 to 80%, more preferably, 30 to 70% relative to the length $w_2$ when the length $w_2$ is defined as 100%. This occurs when the cylindrical bandage 1 of the embodiment is folded such that its circumference of the stitch row on the one circle of the wale side is divided into half in a way that above-mentioned symmetrical line $d_2$ is as the center line and thus one of the insides of the tube touches the other opposite inside.

The length $w_1$ is defined as a length of a virtual perpendicular line that connects the border $P_1$ and the border $P_2$, which are the border between the first tubular knit 10, the second tubular knit 20, and the connecting knit 30 and are the both side. The length $w_2$ is defined as the length of a virtual perpendicular line that extends straightly from above-mentioned virtual perpendicular line to the outline of the first tubular knit 10 and the second tubular knit 20. These length $w_1$ and the length $w_2$ are also measured under conditions where no external force is applied.

The length $w_1$ between the border $P_1$ and the border $P_2$, which are the border between the first tubular knit 10, the second tubular knit 20, and the connecting knit 30, is within a range of 10 to 90%, preferably, 20 to 80%, more preferably, 30 to 70% relative to the length $w_2$, when the length $w_2$ between the outline of the first tubular knit 10 and the outline of the second tubular knit 20 is defined as 100%. Such length $w_2$ is the length of the virtual perpendicular line that extends straightly from above-mentioned virtual perpendicular line, which connects the border $P_1$ and the border $P_2$ between the first tubular knit 10, the second tubular knit 20 and the connecting knit 30. These occurs when the cylindrical bandage 1 of the embodiment is folded such that its circumference of the circle on the wale side is divided into half in a way that the symmetrical line $d_1$, $d_2$ is as the center line and thus one of the insides of the tube touches the other opposite inside.

In the cylindrical bandage 1 of the embodiment, the connecting knit 30 follows 40% or less of the circumference on the circle of the wale side of the endmost part (bottom end part) of the first tubular knit 10 and follows 40% or less of the circumference on the circle of the wale side of the endmost part (top end part) of the second tubular knit 20 by increasing the number of the stitches on the course side, where the yarn is interknitted into loop shapes, between the first tubular knit 10 and the second tubular knit 20. Thus, the connecting knit 30 connects the first tubular knit 10 and the second tubular knit 20. The length a of the virtual perpendicular line $c_1$, which runs from the border P between the first tubular knit 10, the second tubular knit 20, and the connecting knit 30, to the symmetrical line $d_1$ in the front side, and the length b of the virtual perpendicular line $c_2$, which runs from border P to symmetrical line $d_2$ in the rear side are in the ratio 6:4≤a:b≤9:1(a/b is defined as within a range of 6/4 to 9/1) in a state where the cylindrical bandage 1 of the embodiment is folded such that its circumference on the wale side is divided into half at the symmetrical line $d_1$ in front side and at the symmetrical line $d_2$ in the rear side and thus one o inside of the tube touches the other opposite inside.

In this way, the connecting knit 30 is formed by increasing the number of the stitches on the course side between the first tubular knit 10 and the second tubular knit 20. This connecting knit 30 follows 40% and more of the circumference formed of the stitch row on the one circle of the wale side of the endmost part (bottom end part) of the first tubular knit 10 and 40% and more of the circumference formed of the stitch row on the one circle of the wale side of the endmost part (top end part) of the second tubular knit 20. This allows the connecting knit 30 to have a curvature and be formed into three-dimensional object corresponding to the heel. Thus, the connecting knit 30 has a lager curvature and rounder shape than the first tubular knit 10 and the second tubular knit 20 one. This allows the cylindrical bandage 1 to fit the shape of the heel while being worn. In addition, the cylindrical bandage 1 has an appropriate diameter of the cylinder to adapt the circumference of the ankle joint and creates no slack. Thus, the cylindrical bandage 1 is prevented from having a tightness with stretch at the heel side. This allows the knit to be prevented from rising to the surface around the malleolus, specifically, in the rear side of the malleolus, and decrease in the compression.

The diameter of the circle on the wale side of the endmost part (top end part) that follows the connecting knit 30 and the first tubular knit 10 and in the second tubular knit 20, which follows the lower side of the connecting knit 30 and covers the foot side while the cylindrical bandage 1 is worn, is larger than the diameter of the circle on the wale side of the endmost part (bottom end part) that follows the connecting knit 30 and the second tubular knit 20 and in the first tubular knit 10, which follows the upper side of the connecting knit 30 and covers the leg side while the cylindrical bandage 1 is worn, at the connecting knit 30, which corresponds to the heel shape of the human body, as the border. This allows the knit to adapt to bulge of the malleolus and to be prevented from having excessive tension at the heel side and to be in closer contact with the circumference of the malleolus.

Figure 14A:
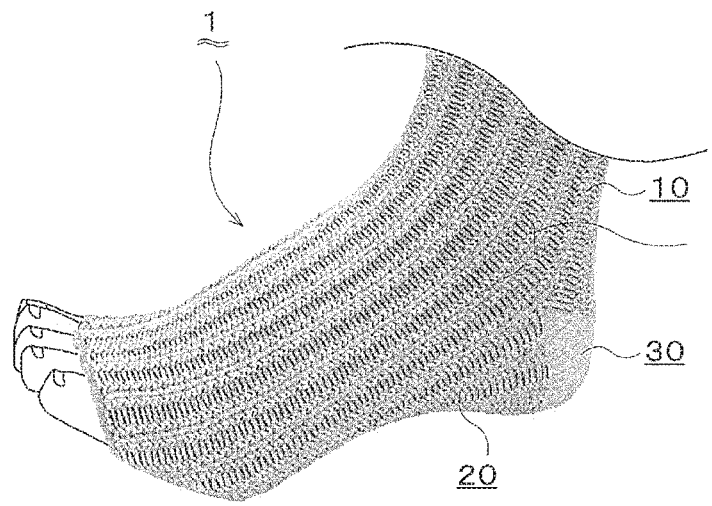
FIG. 14A is appearance view of the cylindrical bandage, which is worn on a foot-mold of the human body, in accordance with the embodiment of the present invention.
Figure 14B:
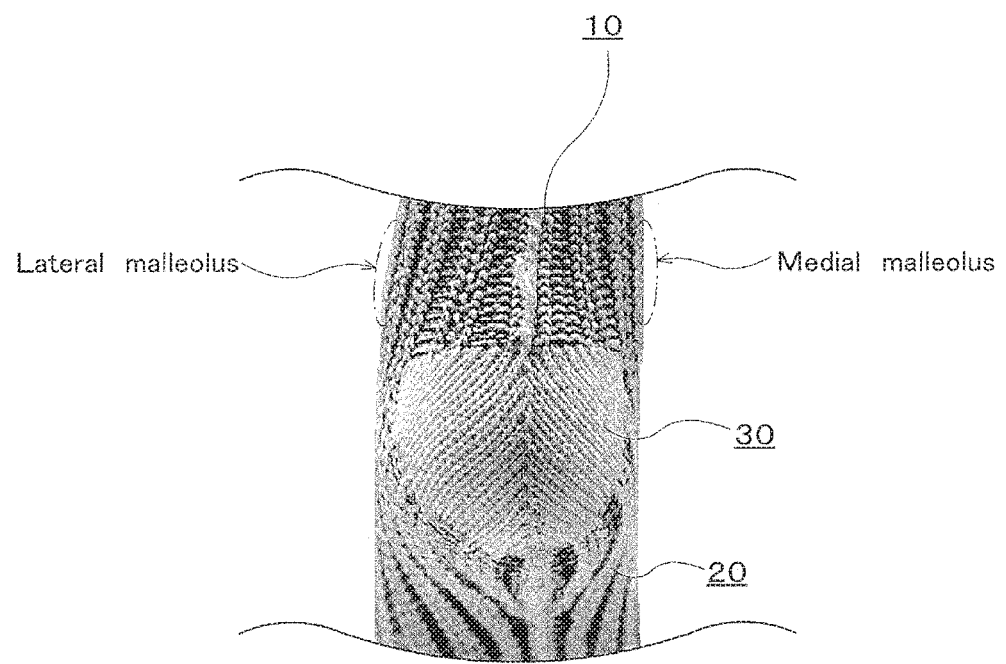
FIG. 14B is appearance view of the cylindrical bandage, which is worn on the foot-mold of the human body, in accordance with the embodiment of the present invention. Specifically, this
Figure 15:
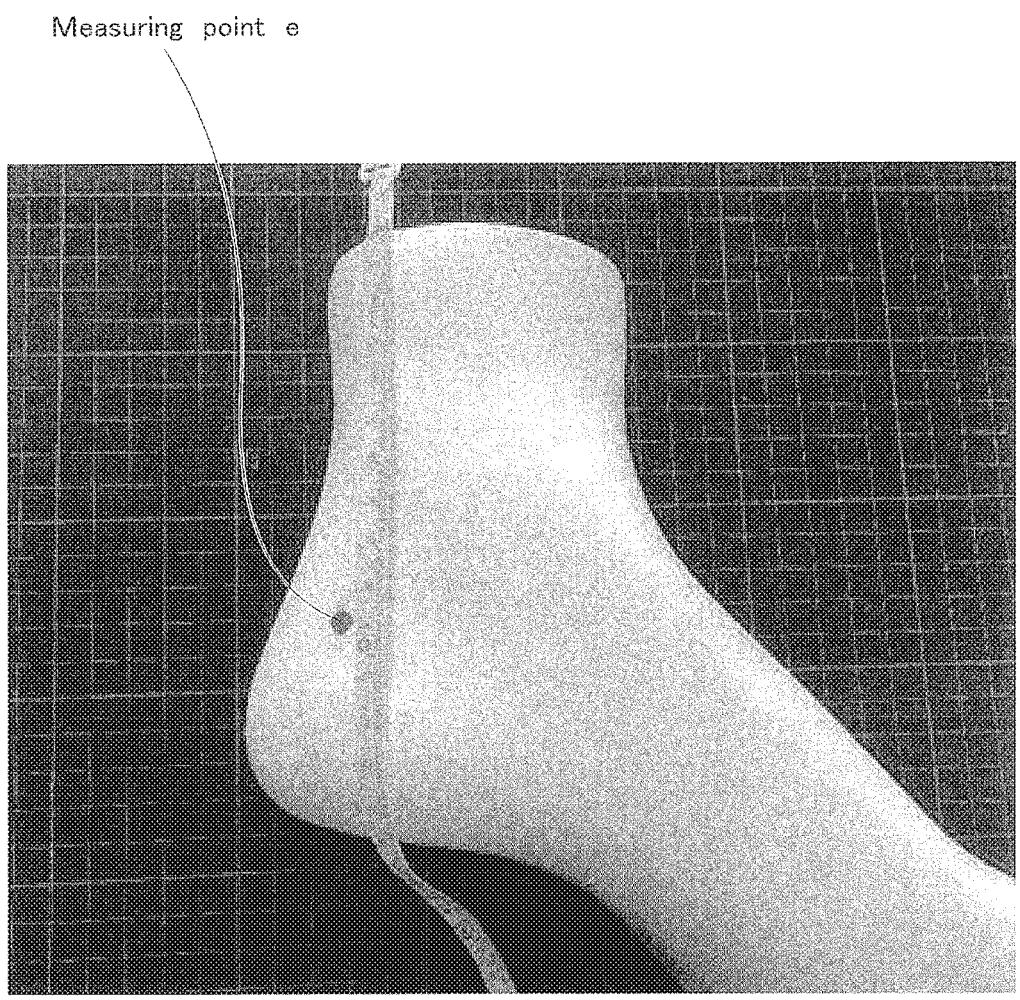
FIG. 15 is explanatory view illustrating a measuring point e (which is a base part around the medial malleolus near the heel side of the foot).
Figure 16:
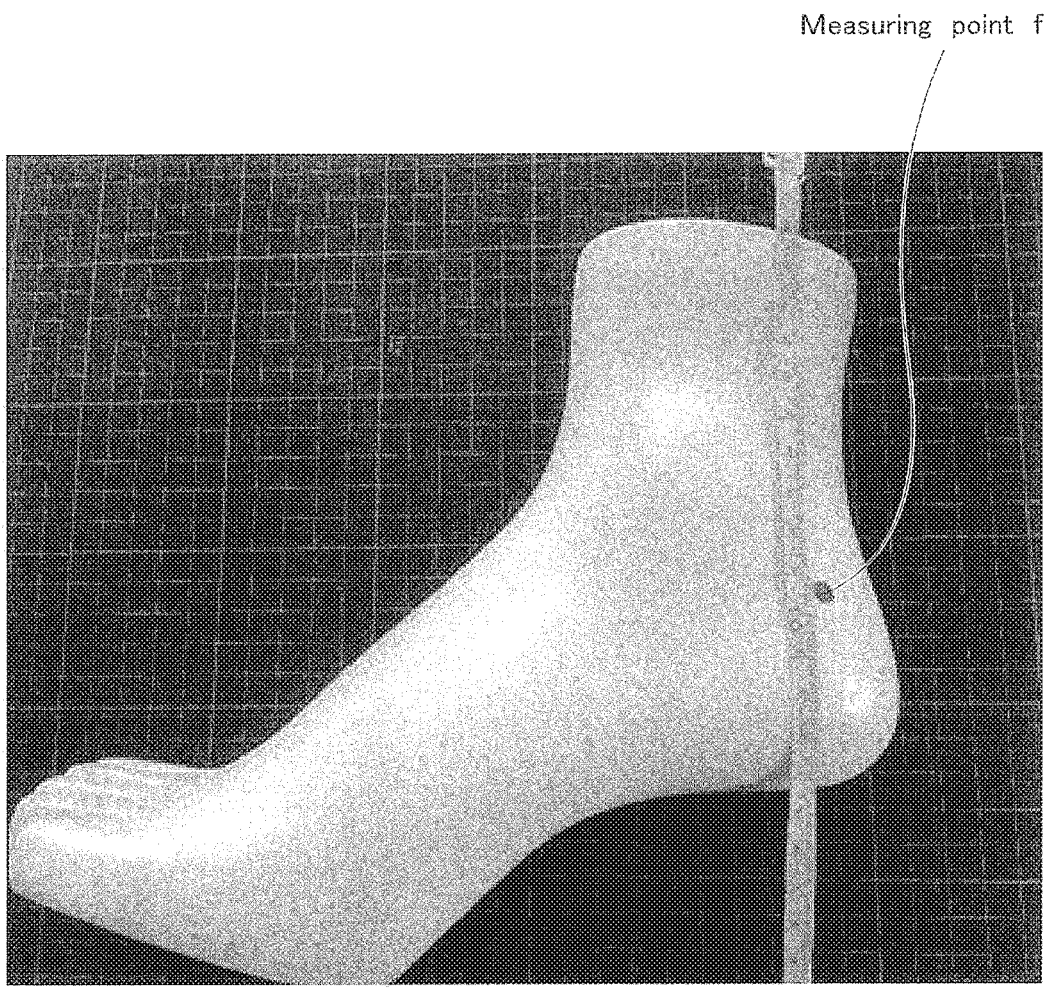
FIG. 16 is explanatory view illustrating a measuring point f (which is a base part around the lateral malleolus near the heel side of the foot).
Figure 17:
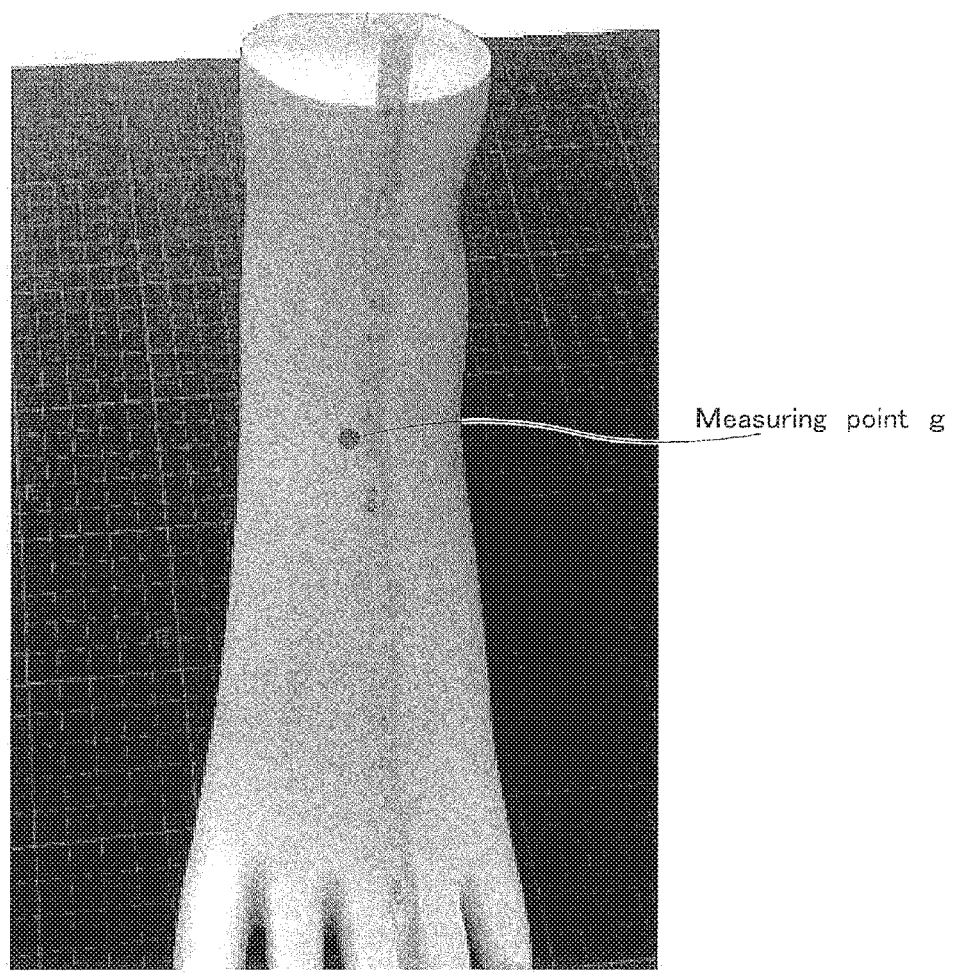
FIG. 17 is explanatory view illustrating a measuring point g (which is the instep part of the foot).
Figure 18:
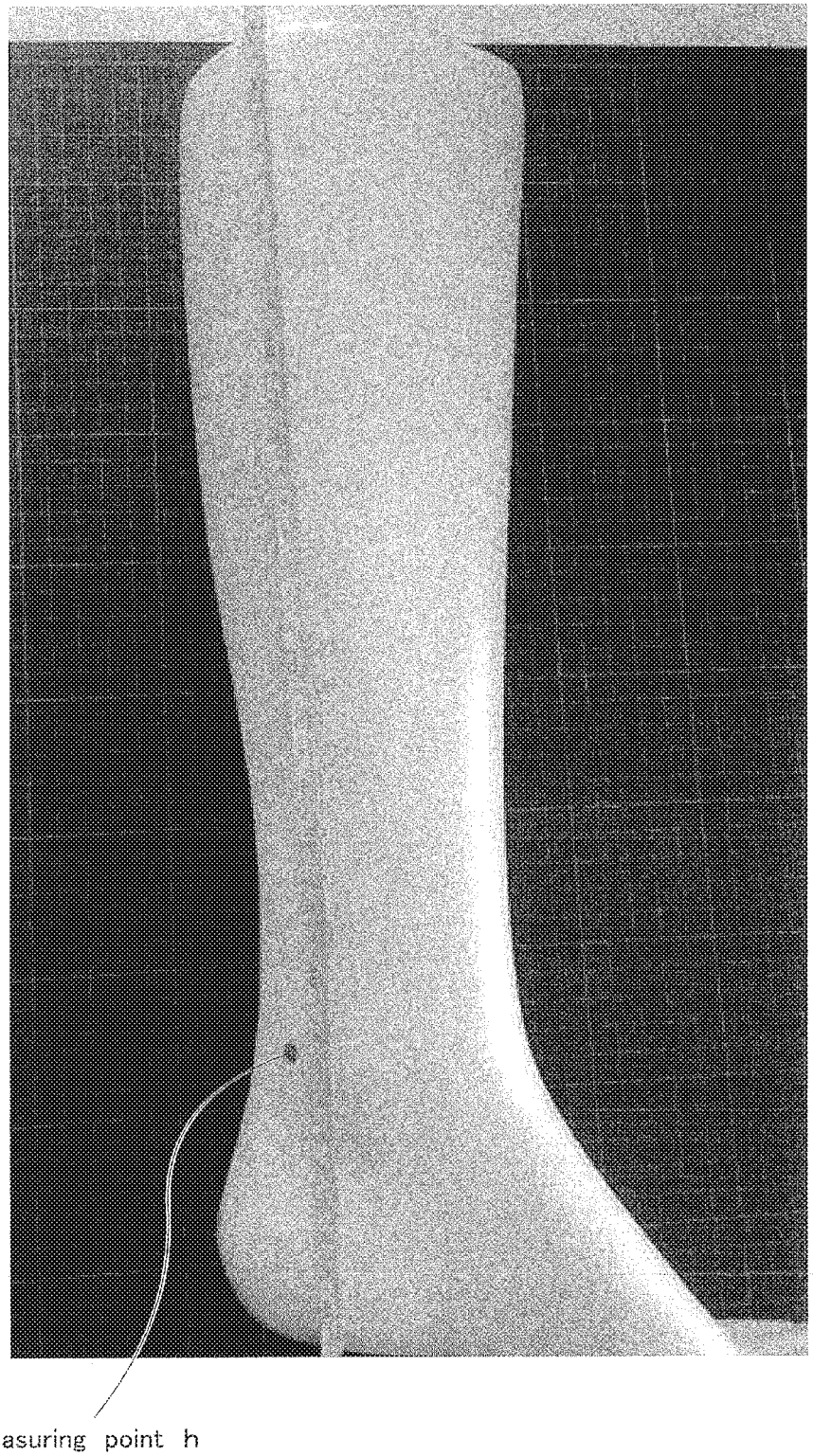
FIG. 18 is explanatory view illustrating a measuring point h (which is a bottom of an ankle of the foot in side part of the foot).
Figure 19:
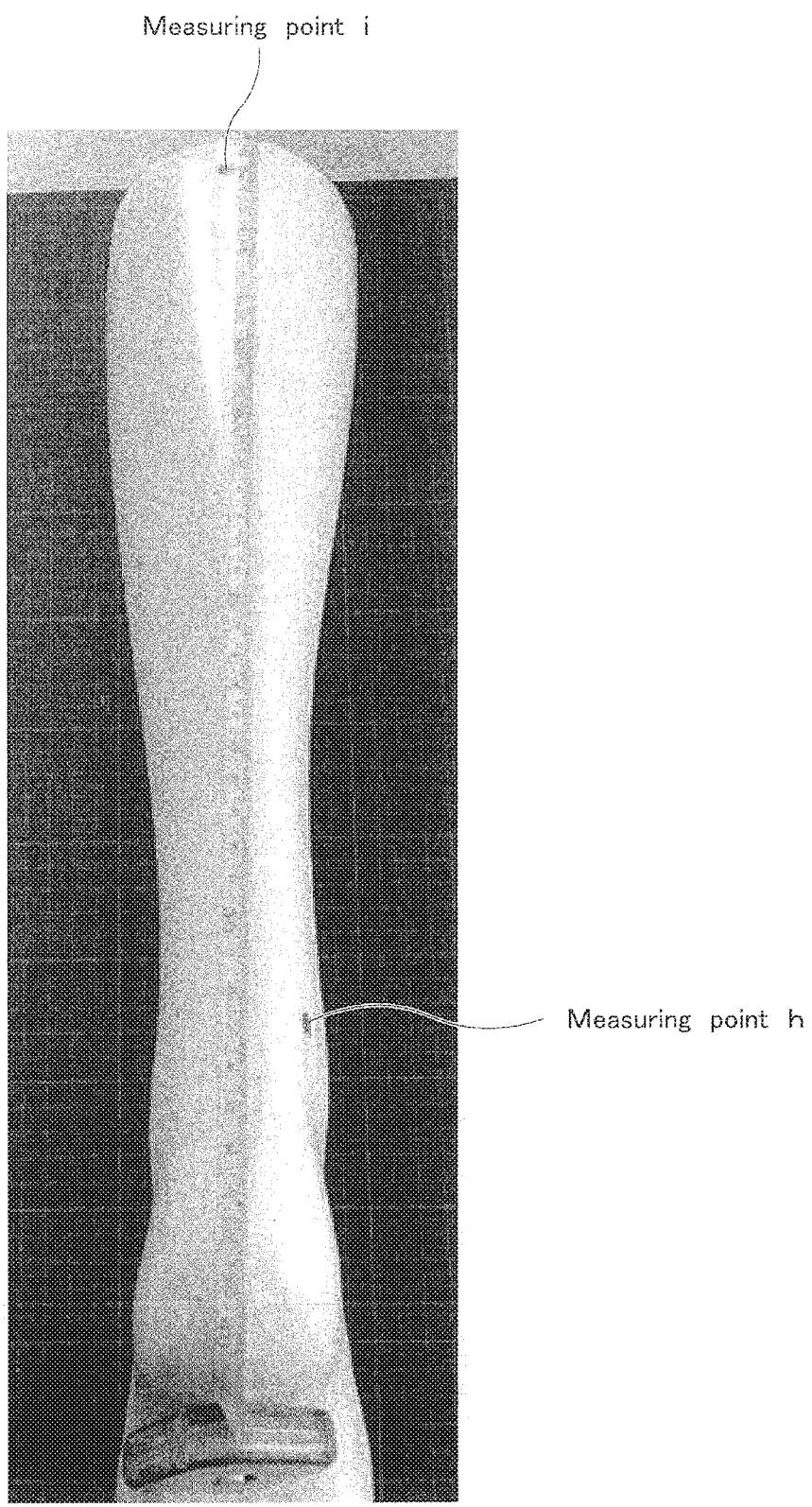
FIG. 19 is explanatory view illustrating a measuring point i (which is a calf part of the foot).

In the connecting relationship between the connecting knit 30 and the first tubular knit 10 and the second tubular knit 20, the length a of the virtual perpendicular line $c_1$, which runs from the border P between the first tubular knit 10, the second tubular knit 20, and the connecting knit 30 to the symmetrical line $d_1$ in the front side, and the length b of the virtual perpendicular line $c_2$, which runs from the border P to the symmetrical line $d_2$ in the rear side, are in the ratio 6:4≤a:b≤9:1 in a state where the cylindrical bandage of the embodiment is folded such that the circumference formed of the stitch row on the one circle of the wale side is divided into half on the symmetrical line $d_1$, $d_2$ and thus one of the insides of the tube touches the other inside. This allows the border P between the first tubular knit 10, the second tubular knit 20, and the connecting knit 30 to be located in the rear side rather than the front side. Therefore, the first tubular knit 10 and the second tubular knit 20 with the predetermined young's modulus cover the curvature part about the malleolus while the cylindrical bandage 1 is worn, as shown in FIG. 14. The connecting knit 30 with a curve fails to the curvature part about the malleolus.

The cylindrical bandage 1 of the embodiment is prevented from having tightness at the heel side, slack at the instep side, and wrinkles at the instep side. Additionally, the first tubular knit 10 and the second tubular knit 20 in this cylindrical bandage 1 cover uneven part around the malleolus while the cylindrical bandage 1 is worn. Thus, the knit is prevented from rising to the surface at the depression part around the malleolus and the knit fits and is in close contact with the curvature around the malleolus. Thus, the cylindrical bandage 1 provides uniform compression-distribution at the circumference of the ankle joint and steady compression.

In particular, the connecting knit 30 follows more than 10% and no more than 40%, more preferably, more than 20% and no more than 40%, of a part of the knitting-width $I_1$ of the endmost part (bottom end part) that is in the first tubular knit 10 and is followed by the second tubular knit 20, and more than 10% and no more than 40%, more preferably, more than 20% and no more than 40%, of a part of the knitting-width $I_2$ of the endmost part (top end part) that is in the second tubular knit 20 and follows the first tubular knit 10. This allows the first tubular knit 10 and the second tubular knit 20 to fails to provide tightness with tension at the heel side and to rise to the surface at the depression part in the irregular part around the malleolus of the foot of the human body. Thus, the first tubular knit 10 and the second tubular knit 20 fit and are in close contact with the irregular shape of the malleolus part and provide steady compression.

As shown in following-mentioned FIG. 12, the connecting knit 30 that connects the first tubular knit 10 and the second tubular knit 20 in the embodiment is knitted by increasing and decreasing the knitting-width (return-width) or varying the position of return-width, that is, varying the number of the stitches on the wale side, where the yarn is loop-interknitted, and thus the connecting knit 30 has a lot of variation in a curvature. This allows the connecting knit 30 to fit the curvature shape in the heel. The first tubular knit 10 and the second tubular knit 20 is prevented from being pulled to the heel side.

In the cylindrical bandage 1 of the embodiment, at least the base formation in the first tubular knit 10 and the second tubular knit 20 are knitted, for example, by the rib stitch, in which the plain stitch and the purl stitch are alternately knitted with the base yarn (groun yarn) A, or the tuck stitch. This yields the base formation in the first tubular knit 10 and the second tubular knit 20 including the depression and the projection that are arranged alternately and contiguously in the circumferential direction (on the wale side). Additionally, the base formation in the first tubular knit 10 and the second tubular knit 20 includes the plain stitch extending in the longitudinal direction (in the perpendicular direction and in the course side) and the purl stitch extending in the longitudinal direction (in the perpendicular direction and in the course side) with the unified knitting.

Figure 9:
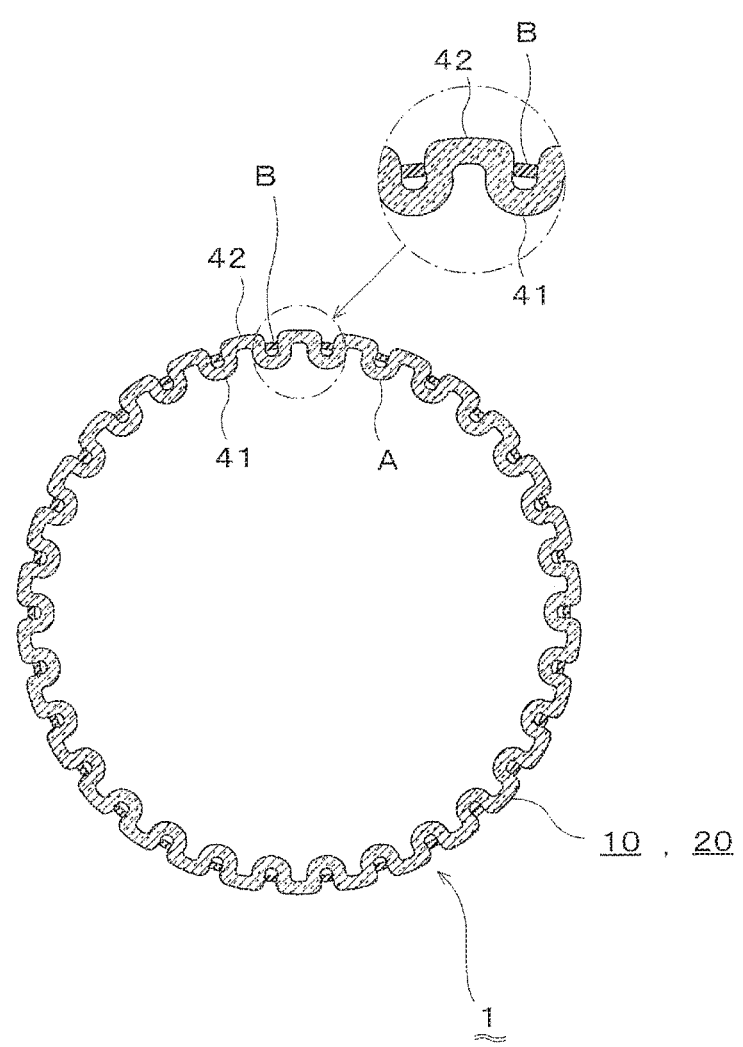
FIG. 9 is a cross-section view illustrating uneven structure of a first tubular knit and a second tubular knit of the cylindrical bandage in accordance with the embodiment of the present invention.

This allows the depression and the projection both extending in the longitudinal direction contiguously on the inside and the outside, or the front side and the rear side, of the first tubular knit 10 and the second tubular knit 20 to be alternately arranged in parallel. Thus, the first tubular knit 10 and the second tubular knit 20 are formed into a corrugation shape in the cross-section, where the depression and projection continue in the circumferential direction, as shown in FIG. 9. The stitch showing the projection on the front side shows the depression on the rear side, which is the reverse of the front side. Conversely, the stitch showing the depression on the front side shows the projection on the rear side, which is the reverse of the front side. That is, the stitch showing the convexity on the outside shows the concavity on the inside. Conversely, the stitch showing the concavity on the outside shows the convexity on the inside.

The stitch showing the convexity on the inside, which touches a wear part of a wearer, and the concavity on the outside, which is the reverse of the inside, is defined as an interior convex part 41. Additionally, the stitch showing the concavity on the inside, which touches the wear part of the wearer, and the convexity on the outside, which is the reverse of the inside, is defined as an exterior convex part 42. Such interior convex part 41 and exterior convex part 42 are alternately arranged next to each other in the circumferential direction (on the wale side). That is, interior convex part 41 is arranged in parallel in the circumferential direction (on the wale side) through the exterior convex part 42 and extends in the longitudinal direction contiguously on the inside, which touches the skin of the wearer.

Since the cylindrical bandage 1 has a plurality of convex part 41 that extend in the longitudinal direction contiguously and are arranged in parallel in the circumferential direction on the inside that touches the skin of the wearer, the cylindrical bandage 1 of the embodiment can put deeply pressure on the skin of the wearer. Additionally, such interior convex part 41 provides the variation in the compression (pressure with tightness) with circular work in the circumferential direction and a consecutive compression in the longitudinal direction. Thus, the strength the compression and the weakness compression are distributed with well-balanced in the circle and the compression continues in the longitudinal direction along the lengthwise flow of the lymph and the venous. This improves the flow of the venous and the lymph; that is, the lymph is returned to the venous effectively, and improves the return-promoting-effect. Additionally, the massage effect enables the skin of the human body to be loose and enables the hyperplasia of the tissue to be reduced and enables the muscle to be relaxed.

Since the knit including the depression and the projection on the inside has the variation in the face, the knit fit and is closely contact with the bending part that has the variation in the circumference of the section of the human body, for example, the circumference of the ankle joint near the heel.

Figure 10A:
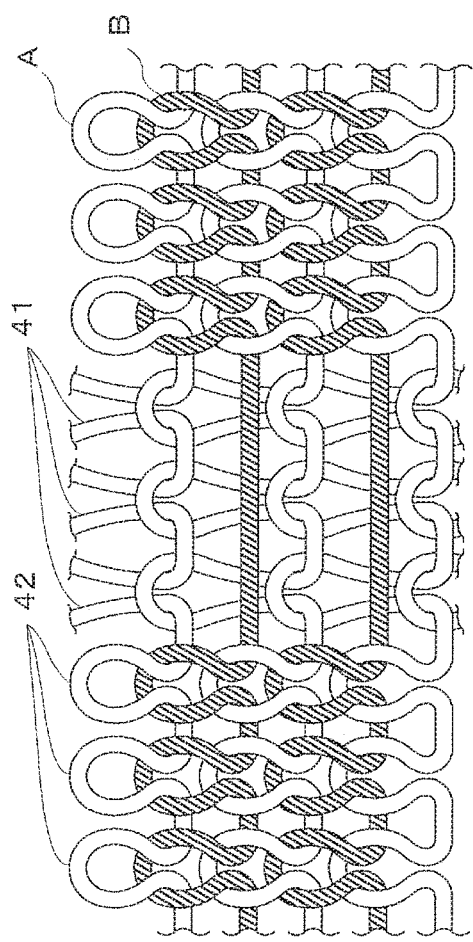
FIG. 10A is a knitting diagram illustrating knitting form of the first tubular knit and the second tubular knit of the cylindrical bandage in accordance with the embodiment of the present invention. Specifically, this
Figure 10B:
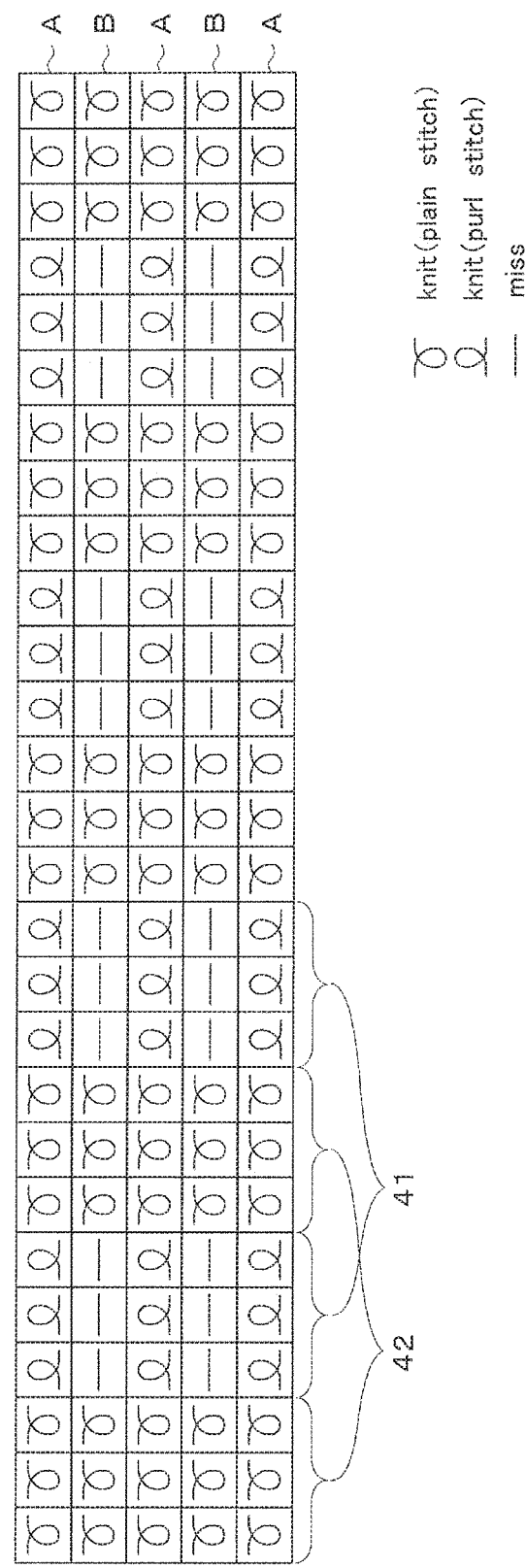
FIG. 10B is a knitting diagram illustrating the knitting form of the first tubular knit and the second tubular knit of the cylindrical bandage in accordance with the embodiment of the present invention. More specifically, this
Figure 11:
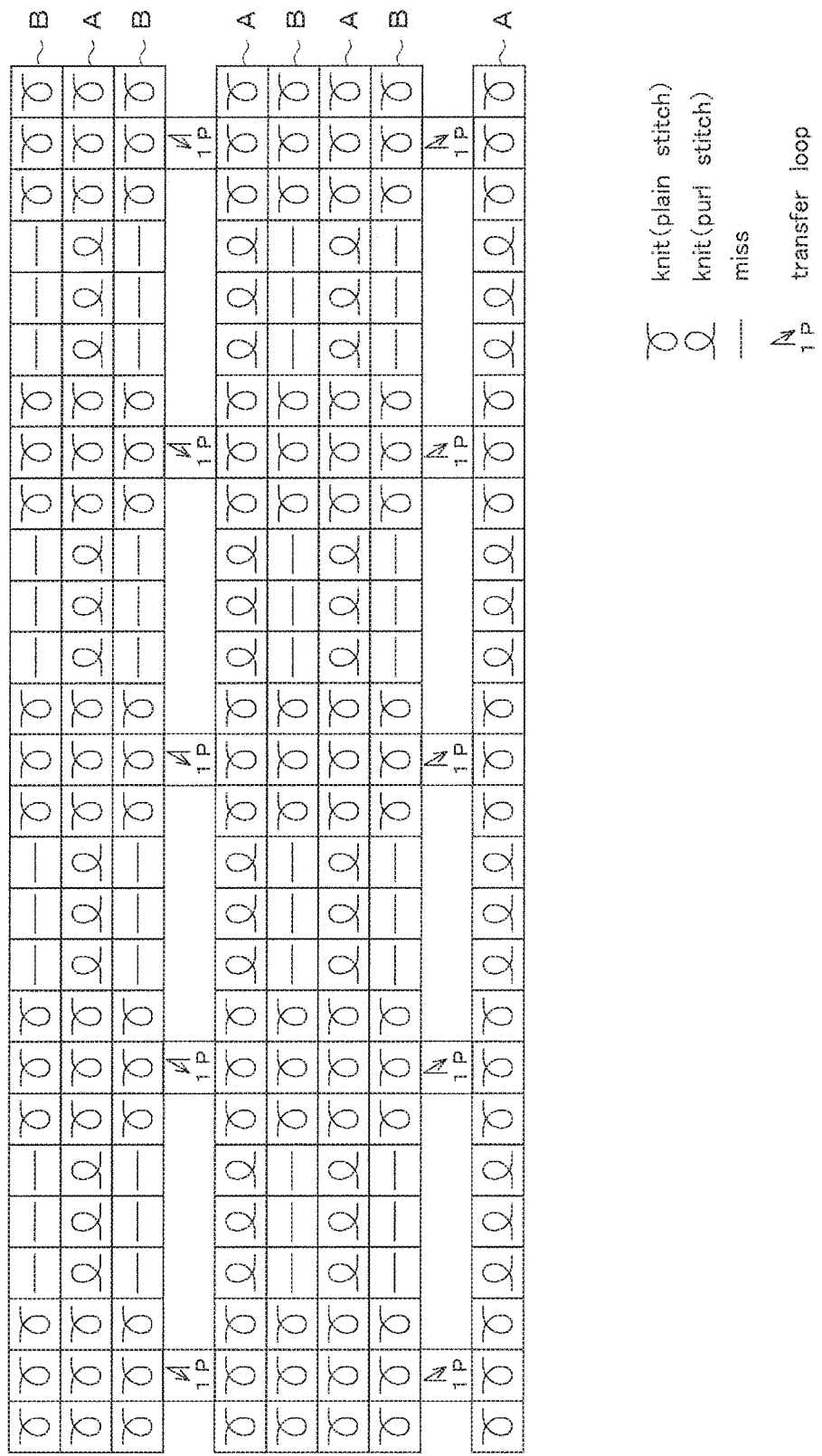
FIG. 11 is a schematic diagram illustrating knitting course to illustrate the knitting form of the first tubular knit and the second tubular knit of the cylindrical bandage in accordance with the exemplified embodiment of the present invention.

In the cylindrical bandage 1 of the embodiment, the elastic yarn B, which has higher elasticity or stretch than the base yarn A one, is cross-knitted and inserted into the base formation including the depression and projection, which are formed of the rib stitch using the base yarn A or other stitch using the base yarn A, at predetermined interval on the course (layer) as shown in FIG. 10. This elastic yarn B is interknitted to the stitch forming the exterior convex part 42 in the rib base formation formed of the rib stitch using the base yarn A. That is, this elastic yarn B is interknitted by crossing the loops. Additionally, such elastic yarn B misses knitting the stitch that forms the interior convex part 41 or the elastic yarn B is tucked into the stitch that forms the interior convex part 41. FIG. 10 and FIG. 11 show the example of the miss knitting; welt position. Thus, the knitting and the missing are alternately and repeatedly used or the knitting and the tucking are alternately and repeatedly used.

Figure 4A:
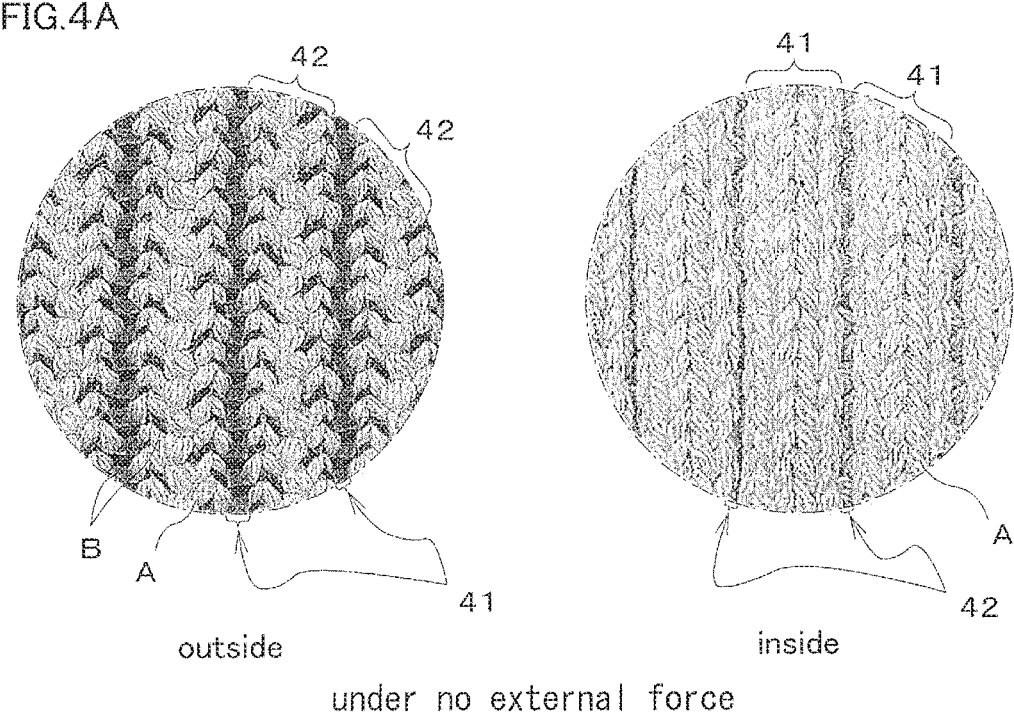
FIG. 4A is an enlarged view of a partial part B shown in FIG. 2 and a photo of the cylindrical bandage of the embodiment. This photo shows the knitting on the outside (a front side) of the cylindrical bandage and on the inside (a rear side) of the cylindrical bandage in state in which no external force is applied to the cylindrical bandage.
Figure 4B:
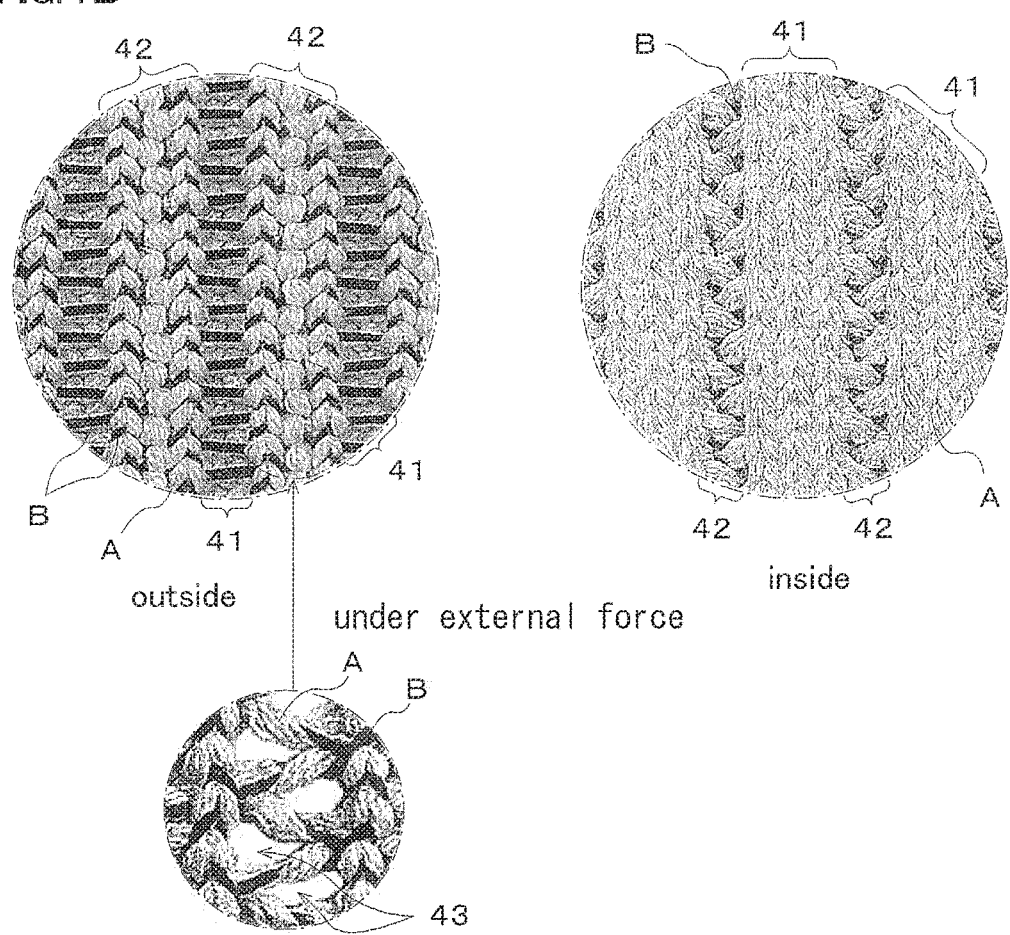
FIG. 4B is an enlarged view of a partial part B shown in FIG. 2 and a photo of the cylindrical bandage of the embodiment. This photo shows the knitting on the outside (a front side) of the cylindrical bandage and on the inside (a rear side) of the cylindrical bandage in state in which predetermined external force is applied to the cylindrical bandage and thus the cylindrical bandage stretches in a wale direction (a circumferential direction).
Figure 5A:
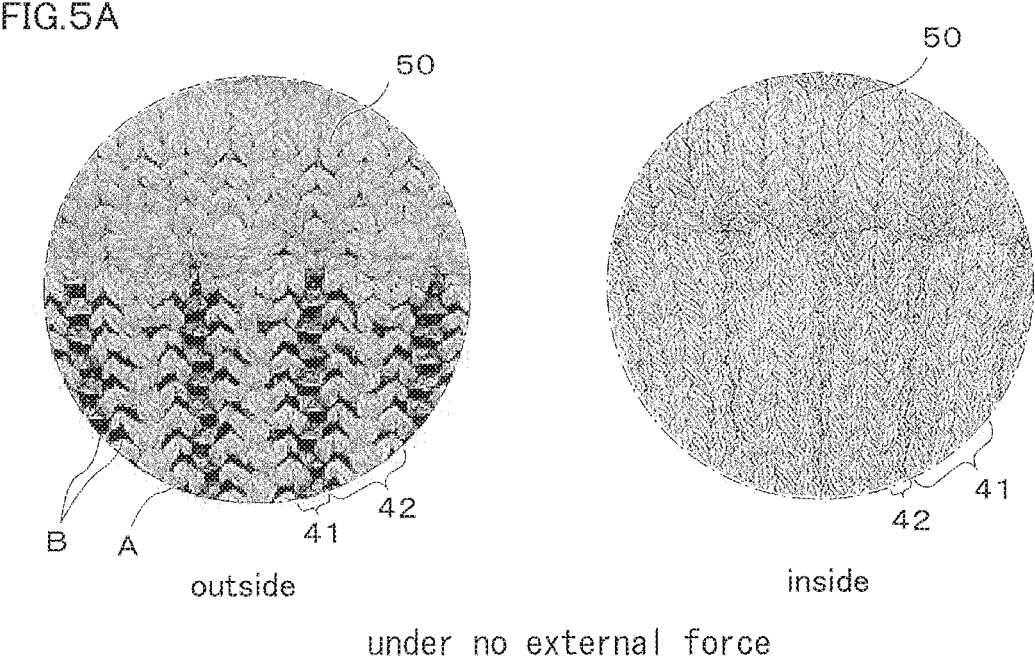
FIG. 5A is an enlarged view of a partial part C shown in FIG. 2 and a photo of the cylindrical bandage of the embodiment. This photo shows the knitting on the outside (a front side) of the cylindrical bandage and on the inside (a rear side) of the cylindrical bandage in state in which no external force is applied to the cylindrical bandage.
Figure 5B:
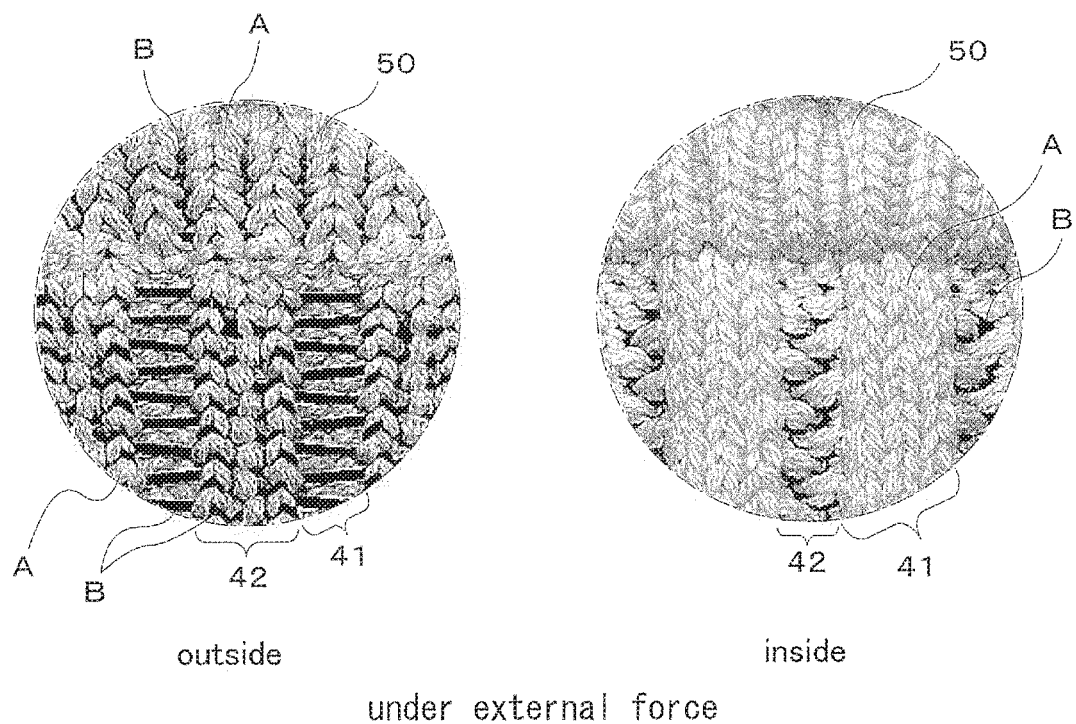
FIG. 5B is an enlarged view of a partial part C shown in FIG. 2 and a photo of the cylindrical bandage of the embodiment. This photo shows the knitting on the outside (a front side) of the cylindrical bandage and on the inside (a rear side) of the cylindrical bandage in state in which predetermined external force is applied to the cylindrical bandage and thus the cylindrical bandage stretches in a wale direction (a circumferential direction).

Thus, in the cylindrical bandage 1 of the embodiment, the elastic yarn B is cross-knitted into the stitch (the plain stitch) forming the exterior convex part 42 in the base formation including the depression and projection formed by the rib stitch or the like. That is, the elastic yarn B is interknitted by crossing the loops. At the same time, this elastic yarn B misses knitting the stitch forming the interior convex part 41 (the purl stitch) or is tucked into the stitch forming the interior convex part 41 (the purl stitch). Consequently, the cylindrical bandage 1 of the embodiment has less revealing elastic yarn B on the inside, which is brought into contact with the skin of the wearer, as shown in FIG. 4 and FIG. 5. In particular, the cylindrical bandage 1 of the embodiment has no revealing elastic yarn B in the interior convex part 41 on the inside. This allows the elastic yarn B to fail to be in contact with the skin of the wearer and allows material, elasticity, rub, or other characteristics of the elastic yarn B to fail to stimulate the skin. Thus, the cylindrical bandage 1 of the embodiment is agreeable to the touch and the texture. The elastic yarn B fails to cause the allergy and the eczema.

In the first tubular knit 10 and the second tubular knit 20, interknitting the elastic yarn B into the rib formation including the depression and projection, which each extends in the longitudinal direction (on the course side) contiguously, enhances elongation or elasticity on the wale side and the course side and enhances tension and compression (pressure with a tight fit).

In particular, the first tubular knit 10 and the second tubular knit 20 have the base formation formed of the rib stitch using the base yarn A and are formed into a cylindrical shape (with circle). Additionally, the first tubular knit 10 and the second tubular knit 20 have the elastic yarn B that is knitted to the stitch forming the exterior convex part 42 in the base formation formed of the rib stitch using the base yarn A. This elastic yarn B misses knitting the stitch forming the interior convex part 41 or is tucked into the stitch forming the interior convex part 41. Thus, the first tubular knit 10 and the second tubular knit 20 have the elastic yarn B that is inserted at the predetermined interval course. This allows the first tubular knit 10 and the second tubular knit 20 to have the tension with circular work and higher tension with the circle (in the wale side) on the outside than on the inside. Consequently, a max thickness and a volume of the interior convex part 41, which shows the projection on the inside that touches the wear part of the wearer, is larger than that of the exterior convex part 42, which shows the projection on the outside, as shown in FIG. 9. This interior convex part 41 therefore includes a curvature, the outline approximating the curve line in the section, and the cross-section approximating semicircular or roundish shape as shown in FIG. 9.

Since the elastic yarn B is inserting into the base formation formed of the rib stitch using the base yarn A by repeating knitting and missing alternately or knitting and tucking alternately, the tension varies in the circumferential direction (on the wale side). In particular, this elastic yarn B is knitted to the stitch forming the exterior convex part 42, which shows the depression on the inside in the base formation. Additionally, this elastic yarn B misses knitting the stitch forming the interior convex part 41 or is tucked into the stitches forming the interior convex part 41, which shows the projection on the inside. Consequently, the thickness and the volume and a curvature of the interior convex part 41, which shows the projection on the inside, are much larger than that of the exterior convex part 42, which shows the projection on the outside. This allows clearer distinction between the projection and the depression, which are formed of the knitting stitch showing the projection on the inside and the knitting stitch showing the depression on the inside.

In the cylindrical bandage 1 of the embodiment, the first tubular knit 10 and the second tubular knit 20 include the interior convex part 41 and the exterior convex part 42. This interior convex part 41 shows the projection on the inside being in contact with the wear part of the wearer and extends contiguously in the longitudinal direction (in the course side) on the inside. The exterior convex part 42 shows the depression on the inside and extends contiguously in the longitudinal direction (in the course side) on the inside. Additionally, the first tubular knit 10 and the second tubular knit 20 include the elastic yarn B inserted into the formation including the depression and the projection, which each extends contiguously in the longitudinal direction, and are formed into a cylindrical (circular) shape. This elastic yarn B is particularly cross-knitted into the stitch forming the exterior convex part 42 in the base formation formed of the rib stitch using the base yarn A. Additionally, this elastic yarn B is cross-knitted by miss-knitting the stitch forming the interior convex part 41 or tucking the stitch forming the interior convex part 41. Consequently, the tension (the pressure with tightness) with circle is enhanced. This tension is higher on the outside, which is a reverse of the inside, than on the inside, which is in contact with the wear part. Additionally, this tension varies in the circumferential direction (on the wale side). Consequently, the interior convex part 41, which shows the projection on the inside being in contact with the wear part, and the exterior convex part 42, which shows the depression on the inside, are different in the tension. This allows the interior convex part 41, which is on the inside being in contact with the skin of the wearer and extends contiguously in the longitudinal direction (in the course side), to have much larger max thickness and much larger volume and a curvature. Therefore, the interior convex part 41 has more cushioning or more elasticity to the thickness direction and thus is in contact with the wear part more closely or more widely. This yields high compression and pressure.

The base yarn A, which forms the base formation including the depression and the projection formed by the rib stitch or other stitch, may include, for example, cotton yarn, nylon yarn, polyester yarn, rayon yarn, silk acrylic yarn, silk yarn, hemp yarn, cotton acrylic mixed yarn, hemp acrylic mixed yarn, wool yarn, wool a mixed yarn such as wool acrylic mixed yarn absorbent yarn that has synthetic fiber block copolymerized with the hydrophilic group or a porous surface, ceramic yarn with far-infrared, or elastic yarn such as polyurethane or rubber. The type of the yarn, the number of the yarn, the count of the yarn is not limited. The base yarn A may include any type of yarn, combined or blend yarn, or bundled yarn.

The elastic yarn B has larger elasticity than the base yarn A one. The elastic yarn B may include, for example, polyurethane or rubber. The elastic yarn B may use covered yarn, which is formed of the core yarn using high elasticity yarn, such as polyurethane or span textile, and other yarn surrounding the core yarn. The elastic yarn B may include combined or blend yarn.

Although the knit has strength or elasticity by knitting, it is preferable that the yarn is hard to cut and tough and has relatively high mechanical strength including tensile strength.

With a thick yarn having, for example, a range of 500 to 2000 denier, the cylindrical bandage 1 may be hard and thick. Thus, the cylindrical bandage 1 may fail to create wrinkles and is prevented from having slack and horizontal wrinkles while being worn. This yields high return-promoting-effect.

The first tubular 10 and the second tubular knit 20 of the cylindrical bandage 1 preferably have the thickness that is within a range of 2 to 15 mm, more preferably, 5 to 15 mm in the cross-section. This allows the knit to hardly create wrinkles, to fit the wear part very well, to be prevented from having slack and creating horizontal wrinkles, and to provide high return-promoting-effect while the cylindrical bandage 1 is worn. Such cylindrical bandage 1 fails to create wrinkles even on the part having movement such as bending while being worn. For example, the part includes the instep side of the foot. Additionally, the cylindrical bandage 1 fails to provide the concentration of the compression and tourniquet action with wrinkles cutting into the skin. The range of 2 to 15 mm, more preferably, 5 to 15 mm in the thickness (in the cross-section) of the knit is measured under no external force.

The formation with the rib stitch is formed of the plain stitches (face stitches) and purl stitches (back stitches) that are arranged alternately on the wale side (the horizontal row of the loops), which continues in the yarn-feeding direction, by a predetermined cycle. Each plain stitch and each purl stitch is knitted to be continuous to the course side (the vertical row of the loops), which continues in perpendicular direction with respect to the yarn-feeding direction, in the embodiment.

In some embodiments, the connecting knit 30 may be formed of the rib stitch formation or by other knitting way that is not same as the first tubular knit 10 and the second tubular knit 20. For example, the connecting knit 30 may be formed of plain stitch such as jersey stitch, pearl stitch, or interlock stitch.

The cylindrical bandage 1 of the embodiment includes an auxiliary fixing part 50 at the end part of the first tubular knit 10. Such end part of the first tubular knit 10 is the opposite side of the connecting knit 30 and the second tubular knit 20, which follow the first tubular knit 10, and near to the heart of human body with wearing. The auxiliary fixing part 50 is formed by increasing the number of the stitches from the first tubular knit 10 to the course side.

The auxiliary fixing part 50, which is located in the topmost of the cylindrical bandage 1, is opened for insertion of a part of the human body (a foot and a leg). The auxiliary fixing part 50 requires the elasticity to prevent a movement and a slide of the cylindrical bandage 1 freely and to keep the cylindrical bandage 1 at a predetermined position. For example, the rib stitch may allow the auxiliary fixing part 50 to have such elasticity. Inserting the elastic yarn B having high elasticity such as rubber may enhance the tension as same as the first tubular knit 10 and the second tubular knit 20 one.

When the auxiliary fixing part 50 has higher young's modulus than the unit of first tubular knit 10 (top end part of first tubular knit 10) next to the auxiliary fixing part 50 has one and thus the auxiliary fixing part 50 includes the knit having low elasticity, the auxiliary fixing part 50 fails to have large elasticity at the topmost part of the first tubular knit 10, which touches the femurs, or rather, the auxiliary fixing part 50 has low elasticity at the top end part of the first tubular knit 10, which touches the femurs. This allows the auxiliary fixing part 50 to fail to cut into the part of the human body. Thus, the wearer is prevented from having redness and itch of the skin. The wearer feels comfortable.

If the first tubular knit 10 is located in the topmost of the cylindrical bandage 1, the young's modulus fails to be affected by the next unit and thus a high elasticity may be directly applied to the femurs. This may cause the wearer to have bad circulation of the blood and to have redness and itch of the skin with a tight fit at the femurs touched by the end of the first tubular knit 10. However, these troubles can be solved by forming the auxiliary fixing part 50 formed of the knit including low elasticity knit at the topmost of the first tubular knit 10. Such auxiliary fixing part 50 enables the prevention of return failure caused by concentration of the compression. In particular, variation in the young's modulus in order in auxiliary fixing part 50, which is the unit next to the end part of the first tubular knit 10, allows the circulation of the blood to fail to be worse. Keeping the elasticity while single knit is folded double also allows the circulation of the blood to fail to be worse. The auxiliary fixing part 50 having low elasticity instead of high elasticity at end part in the first tubular knit 10, which touches the femurs enables the prevention of the inflammation such as redness and itch of the skin effectively and the prevention of the concentration of the compression.

In some embodiments, the first tubular knit 10 and the second tubular knit 20 may include the auxiliary fixing part 50. All these first tubular knit 10 and second tubular knit 20 and auxiliary fixing part 50 may be knitted by using the human body position dates $L_1, L_2, L_3, \ldots$ in the lengthwise direction of a part of the human body being the object of the wear, and the human body circumference dates $m_1, m_2, m_3, \ldots$, which are the circumference in the section being perpendicular to the human body position dates $L_1, L_2, L_3, \ldots$. These first tubular knit 10 and second tubular knit 20 and auxiliary fixing part 50 may be set to the number of the stitches that approximates calculation based on the human body circumference dates $m_1, m_2, m_3, \ldots$, which are the circumference of the section being perpendicular to the human body position dates $L_1, L_2, L_3, \ldots$ in the lengthwise direction of the human body, and based on using the predetermined young's modulus in which the positions of the human body position dates $L_8, L_9, L_{10}, \ldots$ are reflected.

In some embodiments, the bottommost part side in cylindrical bandage 1, which is the opposite side of the auxiliary fixing part 50, may have some fray-stopping with circle, which can bind a free end of the yarn. These fray-stopping may be freely cut anywhere. This may allow the length of the second tubular knit 20 to be adjusted to adapt to the length of the foot of the user.

That is, the end side of the second tubular knit 20, which is the opposite side of the first tubular knit 10, includes some fray-stopping with circle. These fray-stopping may be freely cut anywhere and bind the free end of the yarn to prevent fraying.

For example, such fray-stopping is formed by injecting and coating glue formed of synthetic resin into the provided yarn and applying the glue on the yarn while the cylindrical bandage 1 is manufactured. Some fray-stopping with some circles prevent the spread of fraying if the fray-stopping may be cut at any part. Thus, such fray-stopping enables a freely cut anywhere and the adjustment of the length of the second tubular knit 20. Such fray-stopping may be single or double with predetermined width.

In particular, the fray-stopping with colored glue enables a clear distinction of the cut part. The bottommost of the second tubular knit 20, which is shown in FIG. 6, is cut at the fray-stopping with the yarn coated with colored glue.

Such fray-stopping with some circles and freely cut of them allow for the adjustment of the length depending on the body of the wearer, when the standard of the cylindrical bandage 1 is determined by referring to the compression. Thus, the user can select the cylindrical bandage 1 in accordance with the compression, which is an important factor in use. All it takes is cutting the fray-stopping to correspond to the length of the wearing part. This eliminates the need for the wearer to have particular learning. If the cylindrical bandage is partially cut, mechanical strength fails to decrease by the fray-stopping.

In some embodiments, the endmost part in cylindrical bandage 1, which is the opposite side of the auxiliary fixing part 50, may have the fray-stopping knitted by binding off.

Next, such cylindrical bandage 1 of the embodiment is described more specifically by referring to FIG. 10 to FIG. 13, which illustrates the knitting pattern.

For example, the cylindrical bandage 1 of the embodiment is formed by using a flatbed knitting machine that has at least a pair of front-and-rear needle beds facing each other. Using a wholegarment knitting machine that is a flatbed knitting machine made by Shima Seiki Mfg., Ltd. enables the cylindrical bandage 1 to be formed into a cylindrical shape without sewing by going around the yarn. The wholegarment is registered trademark of Shima Seiki Mfg., Ltd. The wholegarment knitting machine that is a flatbed knitting machine made by Shima Seiki Mfg., includes a MACH2X, a MACH2S, and SWG.

The following describes the example of the cylindrical bandage 1 formed into the cylindrical shape without sewing by using the wholegarment knitting machine that has a pair of front-and-rear needle beds facing each other.

The cylindrical bandage 1 is formed by using the flatbed knitting machine that has at least a pair of front-and-rear needle beds facing each other. The front needle bed and the rear needle bed can relatively shift. Such flatbed knitting machine has the needle beds in where two needles insert into a gage slidably. This each needle is operated so as to slide advancing and retreating by using a carriage that runs and slides on the surface of each needle bed. This front needle and the rear needle can relatively shift (racking).

Since the cylindrical bandage 1 of the embodiment is knitted by using the flatbed knitting machine that has a pair of needle beds, the front-and-rear needle beds, facing each other, the cylindrical bandage 1 uses the needles on the front-and-rear needle beds such that the knitting left knitting pattern is as same as right knitting pattern, which faces the left. Thus, the cylindrical bandage 1 includes side knits that face each other in the right and left and have same shape. Such left and right is the side of a front and a rear, when the knee side of the leg and the instep of the foot is defined as the front, and the calf side of the leg and the heel of the foot is defined as the rear while the cylindrical bandage 1 is worn on a lower extremity of the human body. The symmetrical line $d_1$, which is the edge of the front side, and the symmetrical line $d_2$, which is the edge of the rear side, in the context of FIG. 2 that is the view from side, is placed at reverse point of the yarn feeding direction. The cylindrical bandage 1 is knitted by using the needles on the needle beds and going around the yarn such that the symmetrical line $d_1$ and the symmetrical line $d_2$ are knitted by using the needles of the left and right edge included in knitting range on the front and rear needle beds. Thus, the left knit and the right knit are connected at the symmetrical line $d_1$, which is the edge of the front side, and the symmetrical line $d_2$, which is the edge of the rear side. Consequently, the cylindrical bandage 1 is knitted into a cylindrical shape.

The knitting way of the cylindrical bandage 1 of the embodiment is described in more detail with an exemplified embodiment.

The first tubular knit 10 and the second tubular knit 20 of the exemplified embodiment is knitted by cross-knitting the elastic yarn B having relatively high elasticity into the base formation formed by the rib stitch with the base yarn A having relatively low elasticity.

The knitting of the base formation with the rib stitch is described following. At first, the stitch that is shown as plain stitch on the front side (on the outside) of the knit with wearing locks the needles of the front-needle bed. The stitch that is shown as purl stitch on the front side (on the outside) of the knit sifts the rear-needle bed. Subsequently, the stitch is supplied to the needles on the front-needle bed and rear-needle bed in zigzag. This achieves the knitting of the left knit or the right knit on the course. The left or right is the side of the front and the rear. After this knitting on the course, the stitch that is shifted to the rear-needle bed to form the purl stitch is shifted to return the front-needle bed. Thus, all side knit that is the left knit or the right knit is locked (attached) to the front-needle bed. When the other side knit following the one side knit, the stitch that is shown as the plain stitch on the front side (on the outside) of the knit with wearing is left to lock the needles of the rear-needle bed and the stitch that is shown as the purl stitch on the front side (on the outside) of the knit sifts the front-needle bed facing the rear-needle bed. Subsequently, the stitch is supplied to the needles on the front-needle bed and rear-needle bed in zigzag. This achieves the knitting on the course. After this knitting on the course, the stitch that is shifted to the front-needle bed to form the purl stitch is shifted to return the rear-needle bed. Thus, all of the side knit that is the right knit or the left knit is locked (attached) to the front-needle bed. Such left knit and right knit are connected and knitted into a cylindrical shape by feeding the yarn with going around. This forms the rib-stitch formation where the plain stitch and the purl stitch are arranged alternately.

In the exemplified embodiment as shown in FIG. 10 and FIG. 11, the base formation of the first tubular knit 10 and the second tubular knit 20 includes the rib stitch in which the plain stitch and the purl stitch are 3×3 on the wale side using the base yarn A having low elasticity.

In the exemplified embodiment as shown in FIG. 10 and FIG. 11, the elastic yarn B having large elasticity is knitted into the plain stitch forming the exterior convex part 42, which shows the projection on the outside of the knit and the depression on the inside of the knit in the base formation including the 3×3 rib stitch on the wale side formed of the base yarn A having the low elasticity, at predetermined interval on the course(layer). At the same time, this elastic yarn B misses knitting the purl stitch forming the interior convex part 41, which shows the depression on the outside of the knit and the projection on the inside of the knit. This knitting and missing alternately repeated on the wale side causes the elastic yarn B to be cross-knitted into the 3×3 rib stitch formation.

In the exemplified embodiment, such elastic yarn B, which has larger elasticity than the base yarn A one, is thinner than the base yarn A one. Thus, under no external force in a normal state, the cylindrical bandage 1 has less exposure of the elastic yarn B on the inside as shown in FIG. 4(*a*) and FIG. 5(*a*). Also under external force, the cylindrical bandage 1 has less exposure of the elastic yarn B in the interior convex part 41 on the inside and has a less exposure of the elastic yarn B in even the exterior convex part 42 on the inside as shown in FIG. 4(*b*) and FIG. 5(*b*). Thus, it is difficult for the elastic yarn B to be in contact with the skin of the wearer. Seen from the external side (the front side), the base yarn A having the low elasticity and the elastic yarn B having the large elasticity overlap in the interior convex part 41 as shown in FIG. 4 and FIG. 5.

The cylindrical bandage 1 of the exemplified embodiment, is formed of a mesh-like knitting. This occurs when the middle stitch of three stitch forming the exterior convex part 42 is transferred to the next left stitch or next right stitch. More specifically, the middle stitch of three stitch forming the exterior convex part 42 is transferred to the next left stitch or next right stitch alternately for the course direction as shown in FIG. 11. This knitting forms some holes 43 as shown in FIG. 4. Consequently, the exterior convex part 42, which shows the projection on the outside of the knit and the depression on the inside of the knit in the first tubular knit 10 and the second tubular knit 20, has lower density in the knit than the interior convex part 41 one, which shows the depression on the outside of the knit and the projection on the inside of the knit in the first tubular knit 10 and the second tubular knit 20. Thus, forming some holes 43 enhances air permeability.

Using cotton yarn as the base yarn A allows the cylindrical bandage 1 to have good breathability, to be agreeable to the touch and the texture, to have high cushioning, and to have a lot of contact with the wear part.

In some embodiments, the hole 43 enhancing air permeability may be formed of a tucked position.

In the exemplified embodiment, the connecting knit 30, which connects the first tubular knit 10 and the second tubular knit 20, is formed of the plain stitch or the jersey stitch with the base yarn A.

The auxiliary fixing part 50, which is located in the topmost of the cylindrical bandage 1, is formed of braid over braid and formed by cross-knitting the elastic yarn B into the base formation with the base yarn A as same as the first tubular knit 10 and the second tubular knit 20 as shown in FIG. 5. This elastic yarn B is inserted into only the stitch of the exterior side (front side) and thus the interior side, which is in contact with the skin of the wearer, has no exposure of the elastic yarn B. Such elastic yarn B fails to be inserted into the topmost part side (the starting position of braid over braid) and thus the top side has less or no elastic deformation.

Regarding the cylindrical bandage 1 of the exemplified embodiment, an example in which the knitting is set up from the auxiliary fixing part 50, the first tubular knit 10 side is described below. To start with, the plain stitch formation with base yarn A having a low elasticity is formed of braid over braid. The elastic yarn B having a high elasticity is cross-knitted into this plain stitch formation at the predetermined course. This causes the auxiliary fixing part 50 to be knitted with the predetermined course and be formed into a cylindrical shape. Next, the knitted-loop are transferred and distributed to form 3×3 rib. This forms the first tubular knit 10.

The first tubular knit 10 of the exemplified embodiment has a fixed loop diameter with the base yarn A. In this first tubular knit 10, the stitch row on the one circle of the wale side is set to the number of the stitches that approximates calculation based on the human body circumference dates $m_1, m_2, m_3, \ldots, m_6, m_7$, which are the circumference on the section being perpendicular to the human body position dates $L_1, L_2, L_3, \ldots L_6, L_7$ shown in TABLE 1, and based on the predetermined young's modulus in which the positions of the human body position dates $L_1, L_2, L_3, \ldots L_6, L_7$ are reflected. This first tubular knit 10 is knitted in order of the human body position date $L_1$, the human body position date $L_2$, the human body position date $L_3$, ... the human body position date $L_6$, and the human body position date $L_7$.

At the same time, the knitting-width gradually narrows and the diameter of the tube gradually reduces by narrowing, which means decrease in the number of the stitches, in accordance with decrease in the circumference and diameter from the human body circumference dates $m_1$ to the human body circumference date $m_7$ in order as shown in TABLE 1.

Thus, the first tubular knit 10 of the exemplified embodiment is knitted to correspond to the human body position date $L_1$, the human body position date $L_2$, the human body position date $L_3$, ... and the human body position date $L_7$ in that order. The number of the stitches decreases, that is narrowing, to achieve a predetermined diameter of the tube that corresponds to the human body circumference date $m_7$, which is the circumference of the human body position date $L_7$, and to achieve the predetermined the number of the stitches at the bottom end of the first tubular knit 10.

In the first tubular knit 10 of the exemplified embodiment, the elastic yarn B is inserted and cross-knitted into the base formation, which includes the 3×3 rib stitch using the base yarn A, at an interval on the course, for example, as shown FIG. 11, knitting process diagram. In the exemplified embodiment, this elastic yarn B is knitted into the knit part forming the exterior convex part 42, which comprises three plain stitches on the wale side and shows the projection on the outside of the base formation with 3×3 rib stitch using the base yarn A, and misses knitting the knit-part forming the interior convex part 41, which comprises three purl stitches on the wale side and shows the depression on the inside of the knit. Such knitting and missing alternately repeated allows the elastic yarn B to be cross-knitted into the 3×3 rib stitch based of the base yarn A.

In the exemplified embodiment, the middle stitch of the three plain stitches, which form the exterior convex part 42 on the wale side and show the projection on the outside, is transferred to next left stitch or right stitch (the middle stitch is transferred to next left stitch or next right stitch alternately on the course direction).

More specific process is described with FIG. 11, a knitting-process diagram. After the rib stitch course that is 3×3 rib stitch knitted by feeding the base yarn A, the elastic yarn B replaces this base yarn A. This fed elastic yarn B is kitted into the needles that have knitted three plain stitches with rib stitches on the wale side. At the same time, such elastic yarn B misses knitting the needles that have knitted three purl stitches on the wale side. This achieves the elastic yarn stitch course. Next, the elastic yarn B is transposed for the base yarn A. This fed base yarn A is knitted into the needles that have knitted elastic yarn B in the course of the elastic yarn stitch. At the same time, such fed base yarn A is also knitted into the needles that have been missed. This achieves the 3×3 rib stitch. After this 3×3 rib stitch, the elastic yarn stitch course is performed again.

During such rib stitch course and elastic yarn stitch course repeat alternately and appropriately, the middle stitch of the three plain stitches, which form the exterior convex part 42 on the wale side and show the projection on the outside, is transferred to next left stitch or right stitch. This occurs when the rib stitch course and the elastic yarn stitch course have been alternately gone around with knitting by a predetermined number of times. When next rib stitch course and elastic yarn stitch course alternately go around with knitting by a predetermined number of times, the middle stitch of three plain stitches, which form the exterior convex part 42 on the wale side is transferred to next right stitch or next left stitch that is the other side being different from last time.

These repeats form the first tubular knit 10 of the exemplified embodiment.

While such elastic yarn B having large elasticity is cross-knitted into the rib stitch formation with the base yarn A having poor elasticity and thus continues on the course side, the number of the stitches on the wale side is gradually decreased by the narrowing to gradually decrease the diameter of the tube and to correspond to the human body circumference dates $m_1, m_2, m_3, \ldots m_6, m_7$ which is the circumference of the section being perpendicular with respect to the human body position dates $L_1, L_2, L_3, \ldots L_6, L_7$ shown in TABLE 1. This narrowing may be inside narrowing or outside narrowing. The elastic yarn B is cross-knitted to adapt for the narrowing of the rib stitch formation with the base yarn A having poor elasticity.

In the first tubular knit 10 in the cylindrical bandage 1 of the exemplified embodiment, the narrowing at the front side (the symmetrical line $d_1$ side) with the wear allows the decrease in the number of loops on the wale side of the knit, as shown in FIG. 2 and FIG. 6. This achieves decrease of the diameter of the tube to correspond to the human body circumference dates $m_1$, $m_2$, $m_3$, ... $m_6$, $m_7$ and the young's modulus. For example, transferring one stitch of the plain stitch or purl stitch in the rib of the base formation to the next plain stitch or purl stitch can achieve the narrowing. In some cases, transferring the knit or drawing up the knit may achieve the narrowing. Repeating some narrowing and decreasing the number of the stitches at predetermined positions on the course direction yields the diameter of the tube corresponding to the human body circumference dates $m_1$, $m_2$, $m_3$, ... $m_6$, $m_7$ and the young's modulus. The number of needles on the wale side gradually decreases by the one stitch unit or two stitches unit (two stitches unit to four stitches unit in view of the one circle), that is, one needle unit or two needles unit (two needles unit to four needles unit in view of the one circle), in accordance with the human body circumference dates $m_1$, $m_2$, $m_3$, ... $m_6$, $m_7$. This causes the outline to have no unevenness and a continuous straight line, causes wrinkles with unevenness to be invisible, and yields good fit and steady compression for the outline of the leg. Additionally, feeling with the wear is good. In some embodiments, the number of needles on the wale side may decrease by more stitches unit and the outline may have sharp angle.

In the exemplified embodiment, the inside narrowing or outside narrowing is in the front side with the wear, that is, in the edge part of the front side (the symmetrical line $d_1$ side), which is in the left direction in FIG. 2, the side view. Thus, the stitches forming the exterior convex part 42 and the stitches forming the interior convex part 41, which both extend in the course direction continuously, converge to the center line side (the symmetrical line $d_1$ side) in the front side as shown in FIG. 6, the front view with the wear. On the other hand, the stitches forming the exterior convex part 42 and the stitches forming the interior convex part 41 continuously extend in parallel on the course direction in the rear side as shown in FIG. 7. This yields high return-promoting-effect corresponding to a flow of lymph and venous. Straight stitches on the point where the yarn feeding direction is reversed while the knit is knitted are placed on the symmetrical line $d_1$, $d_2$ and are shown on the center line in the front side and the rear side with the wear. This yields a good appearance. Since the reverse point of the yarn feeding direction is not on the malleolus side, the first tubular knit 10 and the second tubular knit 20 can be closer contact with the circumference of the malleolus.

In some embodiments, the narrowing may be in the rear side or the middle side between the front side and the rear side. Specifically, increase and decrease in the number of the stitches; narrowing and widening, at the end part of the left or right causes the knit to have less or no twist.

Next, the yarn is provided to the needles having the knitted first tubular knit 10, which has had decrease in the number of the stitches to achieve the predetermined diameter of the tube by narrowing from the human body position date $L_1$ to the human body position date $L_2$, the human body position date $L_3$, ... , and the human body position date $L_7$ in order. This yarn is fed to the needles of a left end side or a right end side in horizontal direction (the rear side with the wear) on the predetermined front-and-rear-needle beds that have the first tubular knit 10, and such yarn reverses alternately with C shape on the front needle bed and the rear needle bed. This achieves reverse knitting and knitting course forming the connecting knit 30. Meanwhile, the needles having the rest of the first tubular knit 10 are left and keep resting. Thus, such needles fail to be used for the reverse knitting of the course. The resting needles account for 60% or more of the needles on the needle beds having (catching) the stitch row on the one circle of the wale side of the final course of the first tubular knit 10. The yarn is fed to just the needles that account for 40% or less of the needles on the needle beds having (catching) the stitch row on the one circle of the wale side of the final course of the first tubular knit 10. This achieves the reverse course knitting. In the exemplified embodiment, the connecting knit 30 is formed of the plain stitch (referring to FIG. 3 and FIG. 8).

In the cylindrical bandage 1 of the exemplified embodiment, one of the needles, the left end side or right end side in horizontal direction (the rear side with the wear), on the front-and-rear-needle beds having (catching) the stitch row on the one circle of the wale side of the final course of the first tubular knit 10, is used, for example, as shown in FIG. 12, which is the knitting course diagram that shows the knitting process conceptually. Subsequently, the needles that have no final stitch row of the first tubular knit 10 and are next to the needles of the end side are used in order. At the same time, the needles that have (catch) the final stitch row of the first tubular knit 10 and are in the inside of the needles of the end side on the front-and-rear-needle beds, are used in order. These gradually increase the return-width and the knitting-width (the number of the stitches on the wale side). At the same time, the yarn is fed and makes round trips on the needle beds, reversing with C shape on the front needle bed and the rear needle bed alternately. This achieves the return knitting. While the yarn is reversed with C shape on the front needle bed and the rear needle bed alternately and thus the course knitting is achieved, increase in the use of the needles at the both end in the wale side on each needle bed achieves the widening.

After the predetermined knitting-width is achieved, the needles used for the knitting is shifted from the inside to the outside in order on the front-and-rear-needle beds (in order from the left to the right in FIG. 12). At the same time, the needles that have no final stitch row of the first tubular knit 10 are used for knitting in order. These allow the return-width to shift to the outside (the rear side) and the knitting-width (the number of the stitches on the wale side) to gradually reduce, while the yarn alternately reverse with C shape on the front needle bed and the rear needle bed. This achieves the return course knitting. While the yarn reversing with C shape on the front needle bed and the rear needle bed alternately makes the course knitting, the return-width reduces and narrows on the wale side. The rate of decrease in narrowing of the stitch row on the wale side every course is larger than the rate of increase in widening of the stitch row on the wale side every course.

For example, ten needles have (catch) final stitch row of the first tubular knit 10 and are followed by the connecting knit 30. The number of the needles having the connecting knit 30 finally increases to twenty-five needles. For example, such knitting of the connecting knit 30 begins with using two needles that have (catch) final stitch row of the first tubular knit 10 on the one end (the rear side) in the wale side on the predetermined front-and-rear-needle beds as shown in FIG. 12. Subsequently, the widening is achieved by using the needles that have no final stitch row of the first tubular knit 10 in order and using the needles that have final stitch row of the first tubular knit 10 in order and are in the both end parts that are returning points. This causes connecting knit 30 to follow the stitch row of the final curse of the first tubular knit 10. At the same time, the needles used for the knitting on each front needle bed and rear needle bed increase to twenty-five needles by widening and return knitting with C shape. After the needles used for the knitting in the wale side on each front needle bed and rear needle bed have increased to twenty-five needles, the needles used for the knitting on the needle beds is shifted to the outside in order. At the same time, the needles that have no final stitch row of the first tubular knit 10 are used for the knitting in order. The needles used for the knitting on the front needle bed and rear needle bed decrease to two needles by narrowing and return knitting with C shape. Decrease in the unit of the stitches every course is larger than increase in the unit of the stitches every course.

It is preferable that the number of the needles gradually increase and decrease by one unit or two unit (two unit to four unit in view of the one circle); that is, one needle unit or two needles unit (two needles unit to four needles unit in view of the one circle).

In the exemplified embodiment, this causes the connecting knit 30 to have no gore lines (joint lines). In the exemplified embodiment, the number of the knitting that use the needles of the endmost part (one end part of the rear side) on the front-and-rear-needle beds having final stitches of the first tubular knit 10 increases. This causes the course side to have largest number of the stitches that follow the stitches of the endmost part (one end part of the rear side) having final row on the wale side of the first tubular knit 10. Thus, the connecting knit 30 is formed into a circular sector; a circular arch shape, whose center is border part P, as shown in FIG. 3, the side view. In the exemplified embodiment, the front needle bed and the rear needle bed use same the number of the needles for knitting. It is the same with increase and decrease in the number of the needles and shift of return-width. Thus, the left knit and the right knit are symmetrical. FIG. 12 shows only the knitting basic process (the variation in knitting-width) of the right of a front, when the knee side of the leg and the instep of the foot is defined as the front with the wear.

Compared to use of needles on one of the front bed and the rear needle beds, use of the needles on both the front bed and rear needle bed allows the connecting knit 30 to be knitted by using unlimited needles. Thus, the connecting knit 30 can be formed of sufficient the number of the loops. This enables dimensions and shapes of the connecting knit 30 to be expressed more freely and enables the area and the inside space of the connecting knit 30 to be large and adapt to tree-dimensional shape of the heel of the foot. This allows the knit to be prevented from having tightness at the heel with short knit with the wear.

The connecting knit 30 is knitted such that the number of the stitches on the course side following the stitches of the endmost part (one end part of the rear side) having final row of the first tubular knit 10 has a greatest number of the stitches by varying the position and width of the return between both end parts; that is, varying the number of the stitches on the course side in which yarn is interknitted into loop shapes. This enables the connecting knit 30 to have variation in curvature and to fit the tree-dimensional shape of the heel of the foot. The stitch row is formed by going and returning in a way that the knitting-width and the position of the return are varied. This enables the adjustment of budge and a round shape for covering the heel. The connecting knit 30 can has a large space and plenty of room corresponding to the largest budge of the heel and be prevented from having excessive tension at the heel side. The connecting knit 30 has no gore line and thus a good appearance. No gore line allows the knit to stretch and create no wrinkles. Thus, the knit has a more fit for the shape and is prevented from having a tight fit at the heel side. The first tubular knit 10 and the second tubular knit 20 are in contact with the circumference of the malleolus more closely or widely. No excessive force is applied to the knit while the knit is knitted with the flatbed knitting machine, which enables the knit to have less or no twist.

In some embodiments, the knitting-width may be fixed through knitting of the connecting knit 30 or the stitches on the wale side may increase in number.

The connecting knit 30 follows 40% or less of the circumference of the circle, which is formed of the stitch row on the one circle of the wale side, of the last course that is the knitting end of the first tubular knit 10. The This connecting knit 30 follows preferably a range of 10 to 40%, more preferably, a range of 20 to 40% of the needles on the needle bed. Such needles have the stitch row on the one circle of the wale side of the first tubular knit 10. Additionally, the connecting knit 30 follows 40% or less, preferably a range of 10 to 40%, more preferably, a range of 20 to 40% of the circumference of the circle, which is formed of the stitch row on the one circle of the wale side, of the start course that is the setting up of the second tubular knit 20. That is, the connecting knit 30 follows 40% or less, preferably a range of 10 to 40%, more preferably, a range of 20 to 40% of the needles, which is the number of the stitches on the wale side, on the needle beds. Thus, the connecting knit 30 follows 40% or less, preferably, 10% or greater and 40% or less, more preferably, 20% or greater and 40% or less of the knitting-width of the endmost part (bottom end part) that is in the first tubular knit 10 and follows the second tubular knit 20. Additionally, the connecting knit 30 follows 40% or less, preferably, 10% or greater and 40% or less, more preferably, 20% or greater and 40% or less of the knitting-width of the endmost part (top end part) that is in second tubular knit 20 and follows the first tubular knit 10. Consequently, it is difficult for the cylindrical bandage 1 to have excessive tension at the heel side while being worn. Thus, the first tubular knit 10 and the second tubular knit 20 are prevented from rising around the malleolus and are in close contact with the circumference of the malleolus more closely or widely.

In some embodiments, connecting knit 30 may be knitted by using the needles having (locking) no stitch row on the one circle of the last course of the first tubular knit 10 and then increasing the number of the stitches of the wale side gradually without using the needles having the stitch row on the one circle of the last course of the first tubular knit 10. While the connecting knit 30 is knitted, the front needle bed and the rear needle bed may be different in increase and decrease in the number of the needles and sift of the return position and thus left knit and right knit may be asymmetry.

After the connecting knit 30 is formed, the second tubular knit 20 is knitted by using the needles that have (locks) the stitches of the first tubular knit 10 on the front-and-rear needle beds and have paused during the connecting knit 30 is knitted and using the needles that have (locks) the stitches of the connecting knit 30 and feeding the yarn in a circle.

This knitting that uses the needles having (locking) the stitches of the last row of the first tubular knit 10 allows the second tubular knit 20 to follow the first tubular knit 10. At the same time, the knitting that uses the needles having (locking) the stitches of the last row of the connecting knit 30 allows the second tubular knit 20 to follow the connecting knit 30.

The number of the stitches on the one circle of the wale side of the endmost part (top end part) that is in the second tubular knit 20 and follows the connecting knit 30 and the second tubular knit 20 increases by a range of 10 to 40%, preferably, 20 to 30% with respect to the number of the stitches on the one circle of the wale side of the endmost part (bottom end part) that is the first tubular knit 10 and follows the connecting knit 30 and the second tubular knit 20. That is, the diameter of the circle, which is formed of the stitch row on the one circle, of the endmost part that is the second tubular knit 20 and follows the connecting knit 30 and the second tubular knit 20 increases by a range of 1.1 to 1.4 times, preferably, 1.2 to 1.3 times with respect to the diameter of the circle, which is formed of the stitch row on the one circle, of the endmost part that is the first tubular knit 10 and follows the second tubular knit 20 and the connecting knit 30.

The second tubular knit 20 has a fixed loop with the base yarn A in the rib stitch formation as the base formation. This second tubular knit 20 includes the stitch row having the number of the stitches that approximates calculation based on the human body circumference dates $m_8$, $m_9$, $m_{10}$ or $m_9$, $m_{10}$, which are the circumference of the section being perpendicular to the human body position dates $L_8$, $L_9$, $L_{10}$ or $L_9$, $L_{10}$, and based on the predetermined young's modulus in which the positions of the human body position dates $L_8$, $L_9$, $L_{10}$ or $L_9$, $L_{10}$ are reflected. This stitch row is on the one circle forming the circle on the wale side. Such number of the stitches is adjusted to correspond to the variation in dimensions and shapes in the section. The second tubular knit 20 is knitted in order of the human body circumference date $m_8$, the human body circumference date $m_9$, and the human body circumference date $m_{10}$, or the human body circumference date $m_9$ and the human body circumference date $m_{10}$.

In the exemplified embodiment, the knitting-width narrows and the diameter of the tube reduces by narrowing (inside narrowing or outside narrowing) and decreasing in the number of the stitches from the connecting knit 30 to the human body position date $L_9$ and the human body position date $L_{10}$.

In second tubular knit 20 is knitted as same as first tubular knit 10 by inserting and close-knitting the elastic yarn B into the 3×3 rib stitch base formation with base yarn A having small elasticity.

As shown in FIG. 2. and FIG. 7, the second tubular knit 20 of the cylindrical bandage 1 of the exemplified embodiment has the narrowing at the rear side of the foot (the symmetrical line $d_2$ side) with the wear and thus has gradually decrease in the number of the loops on the course of knit and reduce in the diameter of the tube. The narrowing is formed by, for example, placing the one of the plain stitch and purl stitch in the rib of the base formation on next plain stitch or purl stitch, in some case, transferring and drawing up the knit. Repeating the narrowing and the decreasing the number of the stitches at predetermined here and there in the course direction allows the second tubular knit 20 to have the diameter corresponding to the human body circumference dates ($m_8$), $m_9$, $m_{10}$. The number of the needle in wale side is gradually decreased at one stitch unit to two stitches unit (two to four stitches unit in view of whole cylinder), that is, one needle to two needles unit (two to four needles unit in view of whole cylinder). This causes the outline to include straight line having no bump and to have no noticeable wrinkles occurred by the bump and yields a good fit corresponding to the outline of the leg. In some embodiments, the number of the needle in the wale side may be decreased at several stitches unit and the outline may have sharp angle.

In this exemplified embodiment, the stitches are decreased (inside-decreased or outside-decreased) in the number at the rear side of the foot with the wear. That is, the stitches are decreased in the number at the edge part of the rear side, (symmetrical line $d_2$ side) with the wear, which is in right direction in FIG. 2, the side view. The stitch forming the exterior convex part 42 and the stitch forming the interior convex part 41 that are made longer in the longitudinal direction (the course direction) continuously converge for the center line (symmetrical line $d_2$ side) in the rear side of the foot with the wear in FIG. 7, the rear view. On the other hand, each exterior convex part 42 and each interior convex part 41 is made longer in parallel in the longitudinal direction (the course direction) continuously in the instep side of the foot in the front side with the wear as shown in FIG. 6. This yields high return-promoting-effect of lymph and venous from tiptoe of the foot.

In some embodiments, the stitches may be decreased in the number at the back side or middle side between the front side and the back side. The knit formed by decreasing and increasing the number of the stitches at the left end side or the right end side on the needle beds includes less or no twist.

In the knitting of above-mentioned exemplified embodiment, the yarn feeding position shifts at the end of the knitting of the first tubular knit 10 followed by the connecting knit 30 and the beginning of the knitting of the second tubular knit 20 following the knitted connecting knit 30. Thus, the yarn is cut at the both ends of the connecting knit 30. Although cutting yarn has decrease in the mechanical strength, a predetermined durability is kept by measures that prevent the cutting yarn from fraying, such as, tying the yarn or sticking the yarn with synthetic resin glue.

The inventors put this knitted cylindrical bandage 1 of above-mentioned exemplified embodiment on the foot-mold of the human body and measured the compression at the circumference of the ankle joint.

This cylindrical bandage 1 is formed of five cotton yarns 20/2 as the base yarn A forming the first tubular knit 10 and the second tubular knit 20, two double-covered yarns, which includes a polyurethane core yarn (a 260-denier-yarn) and polyester yarn bound around the polyurethane core yarn (a 75-denier-yarn), as the elastic yarn B forming the first tubular knit 10 and the second tubular knit 20, and two cotton yarns 20/2 as the base yarn A forming the connecting knit 30.

The inventors used air-pack type close contact surface pressure measuring system (made by AMI TECHNO, Inc. AMI3037-SB-SET) as a compression measure system. More specifically, the inventors stuck φ=20 mm air-pack of the compression measure system on each measuring part (as shown in FIG. 15 to FIG. 19) on the foot-mold and put the cylindrical bandage 1 on the air-pack. The inventors measured the compression in a state where the foot-mold with the cylindrical bandage 1 was grounded (standing; the heel was not grounded and only sole of tiptoe was grounded). The inventors measured pressure with the close contact surface pressure measuring system in a state where the air-pack was pressed. The inventors recorded measuring dates one minutes after beginning the measurement. The inventors put the cylindrical bandage 1 on the foot-mold five times and measured the compression five times. The inventors calculated average of five measured dates. The result is shown in TABLE 2.

The inventors measured compression at five points as shown in FIG. 15 to FIG. 19. The inventors measured the compression at each measurement point; the base part (a flat part) around the medial malleolus on the heel side of the foot as the measuring point e (where the center of the air-pack is placed), specifically, this base part is 9.8 cm distant from the end part of the ankle of the foot-mold. The base par around the lateral malleolus on the heel side of the foot as the measuring point f, specifically, this base part is 9.5 cm distant from the end part of the ankle of the foot-mold. The top part on the instep of the foot (the front and middle) as the measuring point g, specifically, this top part is 8.5 cm distant from the end part of the ankle of the foot-mold. The inside part on the ankle as the measuring point h, specifically, this inside part is 32.5 cm distant from end part of the calf of the foot-mold. The calf part on the crus as the measuring point i, specifically, this calf part is 1.5 cm distant from the end part of the calf of the foot-mold.

The Compression of the base part (the measuring point f) around the lateral malleolus on the heel side of the foot is measured on the flat part that corresponds to the bottom of the lateral malleolus with protuberance and in the rear side of the lateral malleolus near the heel side.

The compression of the instep part of the foot (the measuring point g) is measured on the front and middle part in the ankle side and on the part just above the top of the plantar arch.

To measure the measuring point e, measuring point f, and measuring point g, the inventors used the foot-mold (left leg) that is used for a display for men's five-toed socks (TENKENSOUI, Co., Ltd. 51-196-10-2). This foot-mold has 24 cm in the circumference of the ankle corresponding to the human body position date $L_7$ shown in FIG. 1, 22 cm in the circumference of the instep and the ankle corresponding to the human body position date $L_8$ shown in FIG. 1, 24.5 cm in the circumference of the arch part of the foot corresponding to the human body position date $L_9$ shown in FIG. 1, and 30.5 cm in the circumference of the base of the little toe corresponding to the human body position date $L_{10}$ shown in FIG. 1.

To measure measuring point h and measuring point i, the inventors used the foot-mold (left leg) that is used for a display for women's five-toed knee socks (TENKENSOUI, Co., Ltd. 51-196-10-2). This foot-mold has 22.5 cm in the circumference of the ankle corresponding to the human body position date $L_7$ shown in FIG. 1 and 34 cm in the circumference of the thickest part of the calf corresponding to the human body position dates $L_5$ shown in FIG. 1.

Similarly, the inventors measured the compression of a elastic stocking for lymphedema on the market (conventional product) for comparison and compared the elastic stocking with the cylindrical bandage 1.

These measurements are shown in TABLE 2.

TABLE 2

<example>

| | measurement parts | | | | |
|---|---|---|---|---|---|
| | e<br>base end part<br>around medial<br>malleolus<br>near heel side | f<br>base end part<br>around lateral<br>malleouls<br>near heel side | g<br>in-<br>step | h<br>an-<br>kle | i<br>calf<br>(crus) |
| first time | 27 | 24 | 25 | 22 | 21 |
| second time | 25 | 25 | 26 | 23 | 20 |
| third time | 26 | 26 | 23 | 24 | 21 |
| fourth time | 25 | 24 | 25 | 23 | 19 |
| fifth time | 26 | 24 | 25 | 24 | 18 |
| the mean value | 25.8 | 24.6 | 24.8 | 23.2 | 19.8 |

<comparative example>

| | measurement parts | | | | |
|---|---|---|---|---|---|
| | e<br>base end part<br>around medial<br>malleolus<br>near heel side | f<br>base end part<br>around lateral<br>malleouls<br>near heel side | g<br>in-<br>step | h<br>an-<br>kle | i<br>calf<br>(crus) |
| first time | 10 | 9 | 22 | 30 | 29 |
| second time | 14 | 11 | 23 | 31 | 28 |
| third time | 17 | 15 | 22 | 30 | 26 |
| fourth time | 15 | 10 | 22 | 28 | 27 |
| fifth time | 16 | 13 | 23 | 28 | 26 |
| the mean value | 14.4 | 11.6 | 22.4 | 29.4 | 27.2 | compression factor: mmHg

As shown in TABLE 2, the cylindrical bandage 1 provides the compression (about 10 to 46 mmHg) intended for medical care of lymphedema (return-promoting-effect) in the lower extremity at each measuring point.

In the comparative example that is conventional product, the compression of the circumference of the malleolus near the heel side (the measuring point e, the measuring point f) is half of the compression of instep of the foot (the measuring point g). The difference in the compression between the base part of the malleolus near the heel side (the measuring point e, the measuring point f) and the instep part of the foot (the measuring point g) is about 50%(8 to 11 mmHg). The compression of the instep part of the foot (the measuring point g) is about 75% relative to the compression of the ankle part (the measuring point h). The compression of the base part of the malleolus near the heel side (the measuring point e, the measuring point f) is only about 45 to 50% relative to the compression of the ankle part (the measuring point h).

By contrast, the cylindrical bandage 1 of the exemplified embodiment provides equal in the compression between the base part of the malleolus near the heel side (the measuring point e, the measuring point f) and the instep of the foot (the measuring point g). The difference in the compression between the base part of the malleolus near the heel side (the measuring point e, the measuring point f) and the instep of the foot (the measuring point g) is only 5%(1 mmHg). The compression of the base part of the malleolus near the heel side (the measuring point e, the measuring point f) and the compression of the instep of the foot (the measuring point g) are equivalent to or greater than compression of the ankle part (the measuring point h).

The cylindrical bandage 1 of above-mentioned exemplified embodiment is prevented from having the wrinkles at the instep of the foot and thus fails to provide the concentration of the compression at the instep of the foot. Additionally, the cylindrical bandage 1 of above-mentioned exemplified embodiment is prevented from having tightness at the heel side. Consequently, the knit can be in close contact with even the circumference of the malleolus and fit the circumference of the ankle joint. This allows the cylindrical bandage 1 to provide higher compression around the malleolus and to provide little difference in the compression between the instep of the foot and the circumference of the malleolus (the base part of the malleolus near the heel side) and to provide steady and uniform compression-distribution. Additionally, the cylindrical bandage 1 provides little difference in the compression between the compression of a range from the instep to the circumference of the malleolus in the foot and the compression of the ankle side. Such compression of a range from the instep to the circumference of the malleolus in the foot is high and equivalent to or greater than compression of the ankle part. Thus, the cylindrical bandage 1 provides strong return circulation effect in the lower extremity and high mitigation effect for edemas and hypertrophy at the malleolus part and the rear side of the ankle. The cylindrical bandage 1 also provides high compression at the circumference of the malleolus near the heel part (the base part of the malleolus near the heel side) and the rear side of the ankle, where the lymph is collected. This enhances return-promoting-effect at the circumference of the ankle joint. Such return-promoting-effect is brought by strength and weakness of the compression derived from the depression and projection (the exterior convex part 42 and the interior convex part 41), which extend in the longitudinal direction contiguously on the inside of the cylindrical bandage 1 and runs along the lymph.)

Next, the inventors evaluate connection between the compression of the cylindrical bandage 1 and improvement effect including return promotion and sense of wearing.

The inventors arranged several types of the cylindrical bandage 1 that are different in the circumference. These cylindrical bandage 1 are formed of five cotton yarns 20/2 as the base yarn A forming the first tubular knit 10 and the second tubular knit 20, two double-covered yarns, which includes a polyurethane core yarn (260-denier-yarn), and polyester yarn, a 75-denier-yarn, bound around the polyurethane core yarn as the elastic yarn B forming the first tubular knit 10 and the second tubular knit 20, and two cotton yarns 20/2 as the base yarn A forming the connecting knit 30.

The inventors put this cylindrical bandage 1 on the circumference of the ankle joint on the foot-mold and measured the compression thereafter. Additionally, the inventors took a questionnaire for testers (thirty people) who are patients with lymphedema and wear the cylindrical bandage 1. The inventors evaluate the result with connecting compression.

Such compression was measured when the cylindrical bandage 1 of the exemplified embodiment was worn on the foot-mold of the human body; above-mentioned foot-mold (left leg) that is used for the display for men's five-toed socks (TENKENSOUI, Co., Ltd. 51-196-10-2). The compression is open to effect of unevenness and elasticity and other characteristics of the wear part of the human body. Thus, the inventors evaluate compression by using the foot-mold model.

The basis of the compression is the compression of the base part of the lateral malleolus near the heel side (the measuring point f) in the evaluation. The compression measure system and the way of measurement is as same above-mentioned.

The patients (thirty people) with lymphedema in the lower extremity really wore the cylindrical bandage 1 of the exemplified embodiment. More specifically, any testers who were patients with lymphedema and a range of middle to severe in disease, wore the cylindrical bandage 1 on their crus about 3 hours to 12 hours a day during about one week to two weeks. Thereafter, the patients answered a questionnaire that is improvement (mitigation) effect of the edema and tightness or constriction with the wear and connected evaluation of them with the compression. With regards to the improvement (mitigation) effect of the edema, when the improvement (mitigation) effect of the edema is higher than before wear, the evaluation is ◎. When the improvement (mitigation) effect of the edema is obtained effectively, the evaluation is ○. When a little improvement (mitigation) effect of the edema is obtained, the evaluation is △. With regards to the tightness or constriction, when the testers feel no or little tight and pressure, the evaluation is ◎. When the testers feel a little tight and pressure and feel no strange in their daily life, the evaluation is ○. When the testers feel strongly tight and pressure and feel strange in their daily life and have skin-trouble (sweaty), the evaluation is △

The result of the evaluation is shown in TABLE 3

TABLE 3

| | compression at measuring point f (mmHg) | | | | | | | | | |
|---|---|---|---|---|---|---|---|---|---|---|
| | 10 | 15 | 20 | 25 | 30 | 35 | 40 | 45 | 50 | 55 |
| improvement of the edema | △ | ○ | ◎ | ◎ | ◎ | ◎ | ◎ | ◎ | ◎ | ○ |
| tightness, constriction | ◎ | ◎ | ◎ | ◎ | ◎ | ◎ | ◎ | ◎ | ○ | △ |

As shown in TABLE 3, the date has demonstrated that 15 mmHg or greater in the compression on the base part of the lateral malleolus near the heel side (the measuring point f) with the cylindrical bandage 1 worn on the circumference of the ankle joint mitigates edemas effectively. The date has demonstrated that, more preferably, 20 mmHg or greater in the compression on the base part of the lateral malleolus near the heel side (the measuring point f) yields higher improvement effect of the edemas. Conversely, 55 mmHg or greater in the compression has sometimes had a less effect for some patients.

Such date has also demonstrated that 50 mmHg or less in the compression on the base part of the lateral malleolus near the heel side (the measuring point f) with the cylindrical bandage 1 worn on the circumference of the ankle joint hardly provides a tight fit and pressure and a strange feeling with wearing. The date has demonstrated that, more preferably, 45 mmHg or less in the compression on the base part of the lateral malleolus near the heel side (the measuring point f) scarcely provides a tight fit and pressure, and provides a good feeling.

Within a range of 10 to 50 mmHg in the compression on the base part of the lateral malleolus near the heel side (the measuring point f) with the cylindrical bandage 1 worn on the circumference of the ankle joint allows the edemas to be mitigated effectively and hardly provides a tight fit and pressure and a strange feeling with wearing. More preferably, within a range of 20 to 45 mmHg in the compression on the base part of the lateral malleolus near the heel side (the measuring point f) yields higher improvement effect of the edemas and scarcely provides a tight fit and pressure, and provides a good feeling.

All several types of the cylindrical bandage 1 that are different in the circumference and used for evaluation, have 20% or less (5 mmHg or less) of difference in the compression between the instep of the foot and the base part around the lateral malleolus near the heel side.

The cylindrical bandage 1 of above-mentioned exemplified embodiment has a fixed loop diameter (length of the stitch) formed of the base yarn A and a fixed loop diameter formed of the elastic yarn B in between the human body position dates $L_1$, $L_2$, $L_3$, . . . . That is, the loop diameter formed of a unitary yarn: the base yarn A or the elastic yarn B, is fixed and the same. This fixed loop diameter formed of the unitary yarn means that all loop diameter is the same when a yarn forming the loop is same. The knit may be formed of one yarn or several types of the yarn. Type of the yarn or thickness of the yarn has effect on the loop diameter. When a yarn is the same, the loop diameter formed of this yarn is the same. The unitary yarn is not limited to one type of the yarn, alternatively, the unitary yarn may be several types of the yarn.

In the cylindrical bandage 1 of above-mentioned exemplified embodiment, the elastic yarn B is knitted into the stitch forming the exterior convex part 42, which is formed of the plain stitch in the 3×3 (purl stitch×purl stitch) rib base formation using the base yarn A, at the one interval course. At the same time, this elastic yarn B misses knitting the stitch forming the interior convex part 41, which is formed of the purl stitch in the rib base formation, or this elastic yarn B is tucked into the stitch forming the interior convex part 41, which is formed of the purl stitch in the rib base formation.

Additionally, the cylindrical bandage 1 of above-mentioned exemplified embodiment has fixed young's modulus and density, which is determined by the number of using needles on the course side and the wale side between the human body position dates $L_1$, $L_2$, $L_3$, . . . .

This enables the wearer to be always under uniform pressure throughout the first tubular knit 10 and the second tubular knit 20. Thus, the external force fails to apply to only particular part in the lengthwise direction of the human body. The wearer feels no strange. The cylindrical bandage 1 of the embodiment can correspond to the variation in the section of the wear part along the lengthwise direction of the human body and provide uniform compression and uniform compression-distribution.

However, in some embodiments, the young's modulus and the density may vary in accordance with the positions in the human body position dates $L_1$, $L_2$, $L_3$, . . . , for example, by varying the number of the stitches and loop diameter, varying the knitting way of the base yarn A, varying position in which the elastic yarn B inserts, or varying the knitting way of the elastic yarn B. This may enable variation in the pressure in the longitudinal direction. Thus, the compression and the compression-distribution may vary in the longitudinal direction. When the cylindrical bandage 1 is worn on, for example, the lower extremity, the cylindrical bandage 1 may be designed so as to have gradually decrease in the compression to near heart of the human body. This enhances the return-promoting-effect.

Figures 13A, 13B:
FIG. 13A is a schematic diagram illustrating another example of the knitting course that shows the knitting form of the first tubular knit and the second tubular knit of the cylindrical bandage in accordance with an embodiment of the present invention.
FIG. 13B is a schematic diagram illustrating still another example of the knitting course that shows the knitting form of the first tubular knit and the second tubular knit of the cylindrical bandage in accordance with an embodiment of the present invention.
Figure 13C:
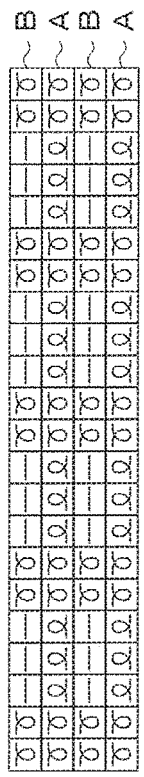
FIG. 13C is a schematic diagram illustrating still another example of the knitting course that shows the knitting form of the first tubular knit and the second tubular knit of the cylindrical bandage in accordance with an embodiment of the present invention.
Figure 13D:
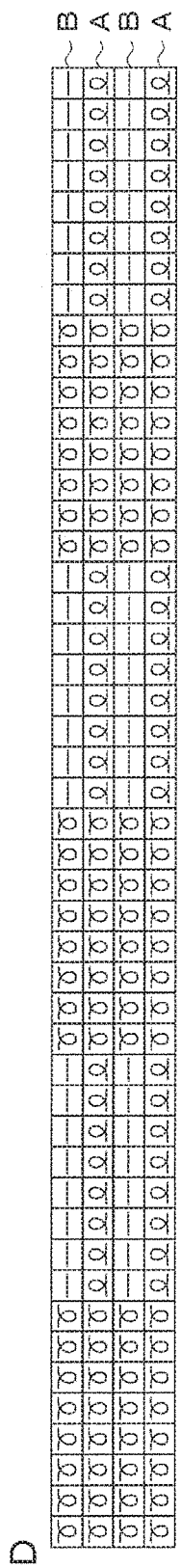
FIG. 13D is a schematic diagram illustrating still another example of the knitting course that shows the knitting form of the first tubular knit and the second tubular knit of the cylindrical bandage in accordance with an embodiment of the present invention.
Figure 13E:
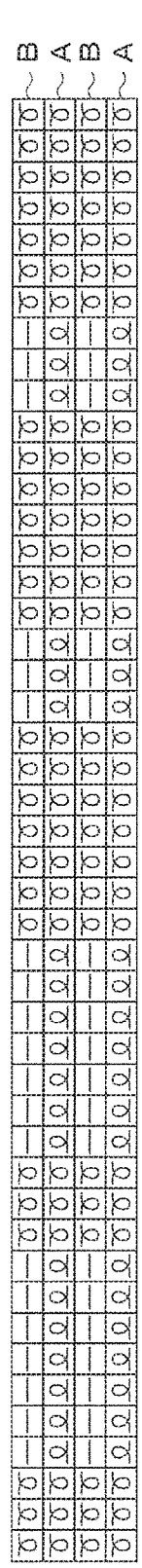
FIG. 13E is a schematic diagram illustrating still another example of the knitting course that shows the knitting form of the first tubular knit and the second tubular knit of the cylindrical bandage in accordance with an embodiment of the present invention.
Figure 13F:
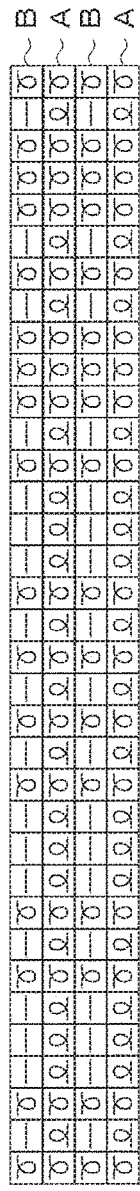
FIG. 13F is a schematic diagram illustrating still another example of the knitting course that shows the knitting form of the first tubular knit and the second tubular knit of the cylindrical bandage in accordance with an embodiment of the present invention.

According to the above-mentioned embodiment, the rib formation in the first tubular knit 10 and the second tubular knit 20 is formed of the 3×3, in which the plain stitch includes the three stitches on the wale side, the purl stitch includes the three stitches on the wale side, and such plain stitch and purl stitch are alternately repeated. However, in some embodiment, the repeated knitting cycle of the plain stitch and the purl stitch is not limited it. For example, the rib stitch formation may be formed of the 1×1(the plain stitch×the purl stitch). as shown in FIG. 13(a). The elastic yarn B may be knitted into this plain stitch forming the exterior convex part 42. At the same time, this elastic yarn B misses knitting the purl stitch forming the interior convex part 41 or is tucked to the purl stitch forming the interior convex part 41 as shown in FIG. 13(a). Alternatively, the rib stitch formation may be formed of the 2×2 (the plain stitch×the purl stitch), as shown in FIG. 13(b) or the rib stitch formation may be formed of the 8×8 (the plain stitch×the purl stitch) as shown in FIG. 13(d). In a same way, the elastic yarn B may be knitted into the plain stitch forming the exterior convex part 42 and missing knitting or is tucked to the purl stitch forming the interior convex part 41.

Additionally, the plain stitch and the purl stitch, or the stitch forming the exterior convex part 42 and the stitch forming the interior convex part 41, may be different in number as shown in FIG. 3 (c), which shows the rib formation formed of the 2×3 (the plain stitch×the purl stitch). As shown in FIG. 3(e) and FIG. 3(f), the number of the plain stitch and the number of purl stitch may vary regularly or irregularly. In this case, elastic yarn B may also be knitted into the plain stitch forming the exterior convex part 42 and elastic yarn B may also miss or is tucked to the purl stitch forming the interior convex part 41.

In some embodiments, the circle of the wale side may have different in the number of stitches forming the exterior convex part 42, which shows the concavity on the exterior and the convexity on the interior and contiguously extends in the longitudinal direction (in the course direction). Also, the circle of the wale side may have different in the number of stitches forming the interior convex part 41, which shows the concavity on the exterior and the convexity on the interior and contiguously extends in longitudinal direction (in the course direction). Thus, the exterior convex part 42 may have variation in the number of the stiches on the circle of the wale side and the interior convex part 41 on the circle of the wale side may have variation in the number of the stiches.

According to the above-mentioned exemplified embodiment, the elastic yarn B is inserted (cross-knitted) into the base formation, such as the base formation formed of the rib stitch using the base yarn A, at one course intervals. However, insertion of the elastic yarn B is not limited to one course intervals. In some embodiments, the elastic yarn B may be inserted into the base formation, for example, at two course intervals or tree course intervals. Alternatively, the elastic yarn B may be irregularly inserted into the base formation in the course direction. To avoid contact with the skin of the wearer, the elastic yarn B is knitted into the plain stitch that forms the exterior convex part 42 in the base formation, such as the base formation formed of the rib stitch using the base yarn A, and misses knitting the purl stitch that forms the interior convex part 41 in the base formation, such as the base formation formed of the rib stitch using the base yarn A in the above-mentioned exemplified embodiment. However, insertion of the elastic yarn B is not limited to that one. In some embodiments, the tucking may be used in place of the missing. Both the missing and tucking may be used. Alternative way of the knitting and missing or alternative way of the knitting and tucking may be used.

According to the above-mentioned exemplified embodiment, both the exterior convex part 42 and the interior convex part 41 extend contiguously in the longitudinal direction (in the course direction). In some embodiments, the exterior convex part 42 and the interior convex part 41 may be arranged and formed into square-block or checked shape and be arrayed dis contiguously in the longitudinal direction (in the course direction). This arrangement provides the depression part (the exterior convex part 42) and the projection part (the interior convex part 41) that are alternatively arranged in parallel on the inside, which is in contact with the wear part, enabling the cylindrical bandage 1 to include the uneven shape (waveform shape) in the section, which has continuous unevenness in the circumference of the circle (on the wale side). This yields strength and weakness of the compression in the circumferential direction, which is perpendicular to the lengthwise direction of the wearer. Consequently, the flow of the lymph and the venous improve and strong return-promoting-effect is obtained. Means of the knitting is not limited to the rib stitch. For example, means of the knitting may be seed stitch, namely, moss stitch, or thermal stitch, namely, waffle stitch. This forms the depression and projection.

According to the above-mentioned exemplified embodiment, the elastic yarn B is inserted into the rib stitch base formation formed of the base yarn A. This insertion of the elastic yarn B and elastic deformation with rib stitch knitting enhance the tension and yield high compression and elasticity. In some embodiments, cross-knitting of the elastic yarn B may be omitted. Alternately, the base yarn A forming the rib stitch base formation may be formed of the elastic yarn having high elasticity. This also yields high compression and elasticity.

According to the above-mentioned exemplified embodiment, setup of the knitting starts from the first tubular knit 10 side. However, setup of the knitting is not limited to it. In some embodiments, setup of the knitting may start from the second tubular knit 20 side and in order of the second tubular knit 20, the connecting knit 30, the first tubular knit 10, and the auxiliary fixing part 50 may be knitted. In this case, the number of the stitches on the wale side is increased by widening toward the connecting knit 30 side to knit the second tubular knit 20. Subsequently, the return-width is varied and the widening and narrowing are conducted to knit the connecting knit 30 following the second tubular knit 20. The number of the stitches on the wale side is increased by widening from the position of human body position dates $L_7$ side toward the position of human body position dates $L_1$ side to knit the first tubular knit 10 following the connecting knit 30.

In the cylindrical bandage 1 of the embodiment, the first tubular knit 10 and the second tubular knit 20 following it have the stitch row on the one circle of the wale side where the number of the stitches are derived from the calculation based on the human body circumference dates $m_1$, $m_2$, $m_3$, . . . in a way which has the predetermined young's modulus in which the positions of the human body position dates $L_1$, $L_2$, $L_3$, . . . are reflected. Thus, increase and decrease in the number of the stitches corresponds to the variation in the dimensions and shapes in the section of the human body, such as the lower extremity.

That is, the cylindrical bandage 1 of the embodiment is knitted by the plain knitting using such as the flatbed knitting machine. This the plain knitting allows the cylindrical bandage 1 to have the variation in the number of the stitches forming the stitch row on the one circle of the wale side in accordance with the circumference of the section of the human body, such as the lower extremity and thus corresponds to the variation in the section of the human body.

The cylindrical bandage 1 has the variation in the knitting-width and the diameter of the circle with the variation in the number of loops (stitches). This causes the cylindrical bandage to have the variation in the section shaped in conformance with the outline the human body such as the lower extremity and to have direction. In this cylindrical bandage 1, increase and decrease in the number of the stitches corresponds to the difference in the dimensions and shapes in the section along the lengthwise of the human body, thus enables the cylindrical bandage 1 to provide predetermined compression. This allows a lot of expression in the dimensions and shapes and a freely-selected circumference. Thus, it is easy to determine the best diameter and the compression that correspond to the dimensions and shapes of the section of the human body. In particular, it is easy to determine the diameter of the tube corresponding to the dimensions and shapes of the circumference of the ankle joint, which conventional elastic stockings knitted by the circular knitting machine fail to put pressure on.

Thus, the cylindrical bandage 1 is prevented from having slack and wrinkles with excessive knit at the instep side of the foot, and providing concentration of the compression with horizontal wrinkles while being worn on, for example, the circumference of the ankle joint. The wearer feels no strange which is caused by the slack and wrinkles with excessive knit at the instep side of the foot while the cylindrical bandage 1 is worn. This cylindrical bandage 1 is prevented from being displaced that is caused by the slack and wrinkles at the instep side of the foot while being worn. Additionally, the cylindrical bandage 1 is prevented from having tightness with short knit at the heel side and having the slack and wrinkles with excessive knit at the instep side of the foot. Since the cylindrical bandage 1 is prevented from having the slack and wrinkles in the circumference of the ankle joint, the knit is prevented from rising at range of the malleolus to the rear side of the heel in the state where the cylindrical bandage 1 is worn with stretch in the longitudinal direction to eliminate the slack and wrinkles. This enables the knit to be in close contact with and put pressure on even the range of the malleolus to the rear side of the heel. Additionally, high compression at the circumference of the malleolus allows reduction of the tissue hypertrophy at the rear side in the malleolus.

In the cylindrical bandage 1 of the embodiment, the number of the stitches and the knitting-width 12 of the stitch row on the one circle of the endmost part (top end part) of the second tubular knit 20 is larger than the number of the stitches and the knitting-width $I_1$ of the stitch row on the one circle of the endmost part (bottom end part) of the first tubular knit 10. That is, the diameter of the circle and the circumference of the stitch row (the last row), which is followed by the first tubular knit 10, on the one circle of the wale side of the second tubular knit 20 is larger than the diameter of the circle and the circumference of the stitch row (the first row), which follows the second tubular knit 20, on one circle of the wale side of the first tubular knit 10. The connecting knit 30 is formed by increasing the number of the stitches on the course side, in which the yarn is interknitted and formed into loop shape, between the first tubular knit 10 and the second tubular knit 20. Additionally, this connecting knit 30 has variation in the number of the stitches on the course side with variation in the knitting-width and variation in return position of the yarn feeding on the needle beds. This enables the connecting knit 30 to have expanded space in the tube for the outline of the heel, which has most expansion, of the foot. Thus, the cylindrical bandage 1 has a solid figure that approximates the outline of the heel of the foot. The cylindrical bandage 1 has no ruggedness and no wrinkles at the heel side while being worn. The cylindrical bandage 1 is prevented from having tightness with excessive force applied at the heel side. Thus, the connecting knit 30 having a curvature connects the first tubular knit 10 and the second tubular knit 20.

In connection between the connecting knit 30 and the first tubular knit 10 and the second tubular knit 20, the length a of the virtual perpendicular line $c_1$, which runs from the border P between the first tubular knit 10, the second tubular knit 20, and the connecting knit 30 to the symmetrical line $d_1$ in the front side, and the length b of the virtual perpendicular line $c_2$, which runs from the border P to the symmetrical line $d_2$ in the rear side, are in the ratio $6:4 \leq a:b \leq 9:1$ in the state where the cylindrical bandage 1 is folded at the symmetrical line $d_1$ in the front side and the symmetrical line $d_2$ in the rear side and the one of the insides of the tube is brought in contact with the other opposite inside of the tube such that the stitch row on the one circle of the wale side is divided into half. Consequently, the first tubular knit 10 and the second tubular knit 20, that have annual outline in the section and have no curvature in the longitudinal direction and thus provide uniform compression, cover the circumference over range of the instep side to the malleolus of the foot while the cylindrical bandage 1 is worn. This enables the cylindrical bandage 1 to fit curvature at the circumference of the malleolus. Additionally, form of the connecting knit 30 having curvature allows the cylindrical bandage 1 to be prevented from having tightness at the heel side while the cylindrical bandage 1 is worn. This allows the first tubular knit 10 and the second tubular knit 20, which cover the depression in the curvature in the circumference of the malleolus, to be prevented from rising. The first tubular knit 10 and the second tubular knit 20 can be close contact with the outline of the circumference of the malleolus and thus provide uniform compression (referring to FIG. 14)

It is preferable for the connecting knit 30 to follow a range of 10 to 40%, more preferably, 20 to 40% of the circumference of the circle formed of the stitch row on the circle of the wale side of the endmost part that is in the first tubular knit 10 and follows the second tubular knit 20 and the connecting knit 30. Additionally, it is preferable for the connecting knit 30 to follow a range of 10 to 40%, more preferably, 20 to 40% of the circumference of the circle formed of the stitch row on the circle of the wale side of the endmost part that is in the second tubular knit 20 and follows the first tubular knit 10 and the connecting knit 30. Consequently, the first tubular knit 10 and the second tubular knit 20 is prevented from be pulled to the heel side and thus having tightness while the cylindrical bandage 1 is worn on and cover the circumference of the ankle joint. This allow for comfortable wear and no tight fit. The first tubular knit 10 and the second tubular knit 20 that cover roughness around the malleolus are prevented from rising with tightness. Thus, the cylindrical bandage 1 is in contact with the curvature around the malleolus more closely.

The cylindrical bandage 1 of the embodiment has the first tubular knit 10 and the second tubular knit 20 that include the base formation formed of the rib stitch or the like. This causes the first tubular knit 10 and the second tubular knit 20 to include the depression part, which is the exterior convex part 42 formed of the stitch showing the concavity on the inside, and the projection part, which is the interior convex part 41 formed of the stitch showing the convexity on the inside, on the inside being in contact with the wear part in the body. Such depression part and projection part each extends in the longitudinal direction (in the course side) contiguously and are alternately arranged in parallel each other in the circumferential direction (in the wale side). Thus, the first tubular knit 10 and the second tubular knit 20 are formed into the uneven shape (the corrugation shape) in the cross-section on the inside, where the depression and projection continue in the circumferential direction on the circle. Such depression and projection yields variation in the close contact and yields strong compression and weak compression in the circumferential direction being perpendicular to the longitudinal direction of the human body while the cylindrical bandage 1 is worn. Additionally, the depression and the projection each extends in the longitudinal direction (in the course side) contiguously. This causes the strength and the weakness of the compression to run along the flow direction of the lymph. Consequently, the flow of the lymph and the return-promoting-effect improve. Additionally, the wearer is under well-balanced pressure and thus feels no strange.

Since the first tubular knit 10 and the second tubular knit 20 including the depression and the projection on the inside has the variation in the face, the knit fits and is in close contact with the shape of the bending part that has the variation in the circumference of the section of the human body.

In the embodiment, the elastic yarn B is knitted to the stitch forming the exterior convex part 42 in the base formation formed of the rib stitch using the base yarn A. At the same time, the elastic yarn B misses knitting the stitch forming the interior convex part 41 or is tucked to the stitch forming the interior convex part 41. Thus, the elastic yarn B is inserted at predetermined interval on the course. Consequently, the tension with the circle is higher on the outside, which is a reverse of the inside, than on the inside, which is in contact with the wear part. This allows the cylindrical bandage 1 to have clearer distinction between the projection part (which is the interior convex part 41 formed of the stitch showing the convexity on the inside) and the depression part (which is the exterior convex part 42 formed of the stitch showing the concavity on the inside) on the inside. Additionally, the interior convex part 41 extending in the longitudinal direction (on the course side) contiguously on the inside, which is brought into close contact with the wear part, has the curvature and has extension of the volume to the thickness direction in the cylindrical bandage 1. This enhances cushioning and elasticity in the interior convex part 41 and thus enables the knit to be in closer contact with the wear part.

Since the elastic yarn B is cross-knitted to the rib stitch formation using the base yarn A by knitting and missing, knitting and tucking, or both, the cylindrical bandage 1 has difference in the tension between the projection part (which is the interior convex part 41 formed of the stitch showing the convexity on the inside) and the depression part (which is the exterior convex part 42 formed of the stitch showing the concavity on the inside) on the inside, which is in contact with the wear part. In particular, the elastic yarn B is knitted to the stitch forming the exterior convex part 42 in the base formation formed of the rib stitch using the base yarn A. At the same time, the elastic yarn B misses knitting the stitch forming the interior convex part 41 or is tucked to the stitch forming the interior convex part 41. This also allows the cylindrical bandage 1 to have clearer distinction between the projection part (which is the interior convex part 41 formed of the stitch showing the convexity on the inside) and the depression part (which is the exterior convex part 42 formed of the stitch showing the concavity on the inside) on the inside. Additionally, the interior convex part 41 extending in the longitudinal direction (on the course side) contiguously on the inside, which is brought into contact with the wear part, has the curvature and has extension of the volume to the thickness direction in the cylindrical bandage 1. This enhances cushioning and elasticity in the interior convex part 41 and thus enables the knit to be in closer contact with the wear part.

Consequently, the cylindrical bandage 1 of the embodiment allows the interior convex part 41 to provide closer contact, increase in the compression and pressure, and high return-promoting-effect.

Thus, the cylindrical bandage 1 is prevented from having slack and providing the concentration of the compression with horizontal wrinkles and having tightness at the heel side while being worn on, for example, the circumference of the ankle joint. Additionally, the knit can be contact with the circumference of the malleolus more closely and fit the circumference of the ankle joint. Consequently, this cylindrical bandage 1 provides no or little difference in the compression between the top side of the instep and the circumference of the malleolus in the foot and thus provides steady and uniform compression-distribution. This yields high return-promoting-effect and enhances mitigation, improvement and prevention effect of the edemas such as the lymphedema. Additionally, this cylindrical bandage 1 is effective for mitigation and improvement of tiredness and swelling. The variation in the number of the stitches easily enables determination of the diameter of the tube and compression corresponding to the wear part of the human body, thus enabling the knit to fit the wear part. Consequently, this cylindrical bandage 1 is prevented from providing pain, skin damage, skin laceration and skin tear that are caused by friction derived from excessive knit or short knit. Additionally, this cylindrical bandage 1 is prevented from providing tourniquet caused by the compression-concentration.

In the cylindrical bandage 1 of the embodiment, the elastic yarn B is knitted to the stitch forming the exterior convex part 42 in the base formation formed of the rib stitch using the base yarn A. At the same time, the elastic yarn B misses knitting the stitch forming the interior convex part 41 or is tucked to the stitch forming the interior convex part 41. Thus, the elastic yarn B is inserted into the base formation. Consequently, the cylindrical bandage 1 has no or less exposure of the elastic yarn B on the inside and thus it is difficult for the elastic yarn B to be in contact with the skin of the wearer. This allows good comfort with wear. Additionally, the characteristics of the yarn including a cotton yarn used for the base yarn A that formed the base formation allows good suction, good comfort for the skin, and good touch on the skin and allows improvement of comfort with wear and prevention of sweaty. The number of stitches or the like can also determine loop diameter, stitch density and other characteristics freely. Thus, the cylindrical bandage 1 permits sufficient breathability.

In the cylindrical bandage 1 of the above-mentioned exemplified embodiment, a predetermined loop transfers (overlaps) to next needle in the exterior convex part 42. This forms several holes 43 as mesh in the cylindrical bandage 1. Thus, this cylindrical bandage 1 permits high breathability (referring to FIG. 4)

The number of the stitches can determine the compression freely. Additionally, other characteristics including elasticity of the base yarn A and the elastic yarn B, means of inserting with the elastic yarn B, and a loop diameter (a diameter of the stitch) can determine the compression freely.

The depression part (which is the exterior convex part 42 formed of the stitch showing the concavity on the inside) and the projection part (which is the interior convex part 41 formed of the stitch showing the convexity on the inside) that each extends contiguously in the longitudinal direction (in the course side) and that are alternately arranged in parallel in the circumference (in the wale side) of the circle and are formed of the rib stitch or the like. According to the above-mentioned exemplified embodiment, the plain stitch and the purl stitch are alternately arranged on the wale side and thus the knit has the variation in the stitch on the wale side in the front and rear. This enables the knit to have no ore less wrinkles and to be contact with the wear part more closely and to provide steady compression.

Since the knit can be very close contact with the circumference of the malleolus (the medial malleolus and the lateral malleolus), in which the lymph is easily collected, the flow of lymph around the malleolus is promoted and the edemas around the malleolus improves effectively. The first tubular knit 10 and the second tubular knit 20 include depression and projection that continue in the circumferential direction of the circle (on the wale side) on the inside. This yields the strong compression and weak compression. This strength and weakness in the compression enhances promotion of the flow of lymph and yields high return-promoting-effect. Since the depression and projection that extend continually in the longitudinal direction (in the course side), the depression and projection run along the flow of the lymph and the venous. This allows improvement of the flow of the lymph and the venous more effectively. When the cylindrical bandage 1 is long in length and covers to the base of the toe as above-mentioned exemplified embodiment, the cylindrical bandage 1 can promote the flow of the lymph from the base of the toe toward the heart direction and provide high return-promoting-effect and high improvement of the edemas near the base of the toe. When the cylindrical bandage 1 is set to provide gradually decrease in the compression from the ankle side to the femurs side, for example, the compression that is within a range of 10 to 70 mmH at the ankle, the compression that is within a range of 5 to 35 mmHg at the crus part, and the compression that is within a range of 3 to 20 mmHg at the femurs, the return-promoting-effect increases effectively.

The first tubular knit 10 and the second tubular knit 20 in the cylindrical bandage 1 of the embodiment have the variation in the number of the stitches to correspond to the variation in the section of the human body. That is, these first tubular knit 10 and second tubular knit 20 have the number of stitches that approximates calculation based on the human body circumference dates $m_1, m_2, m_3, \ldots$, which are the circumference of the human body position dates $L_1, L_2, L_3, \ldots$, and based on the predetermined young's modulus in which the positions as the human body position dates $L_1, L_2, L_3, \ldots$ are reflected. Thus, the number of the stitches and the young's modulus determine the stitch row on the wale side to correspond to the circumference of the human body. This enables provision of predetermined pressure in accordance with positions in the human body and high return-promoting-effect. That is, such determining the number of the stitches and young's modulus enables pressure to correspond to the human body position dates $L_1, L_2, L_3, \ldots$.

In the cylindrical bandage 1 of the embodiment, the first tubular knit 10 and the second tubular knit 20 following it have the variation in the number of the stitches on the circle to correspond to the variation in the section of the human body. This allows the cylindrical bandage 1 to provide custom-made compression in accordance with individual cases. It is also easy to form standard products by calculation based on user date and average figure of the nation. In particular, the variation in the circumference with the variation in the number of the stitches enables the variation in the compression corresponding to parts. Thus, the cylindrical bandage 1 can put desired pressure on partial parts and provides high return-promoting-effect.

The variation in the number of the stitches can correspond to severe deformation with the lymphedema and the varicose vein, enabling the knit to fit and put pressure on the severe deformation. This cylindrical bandage 1 is prevented from providing pain, skin damage, skin laceration and skin tear that are caused by friction derived from excessive knit, short knit or rising knit. Over-the-counter products, such as conventional elastic stockings used for the treatment of the lymphedema varicose vein are designed so as to match for non-Japanese people. Such over-the-counter products fail to match Japanese figure. However, the cylindrical bandage 1 can be formed on the basis of Japanese standard date, which enables the cylindrical bandage 1 to match Japanese size. The cylindrical bandage 1 can be formed as original products to match individual figure.

The cylindrical bandage 1 provides desired and steady compression-distribution for wearer who is under pressure, provided that measurement of physical property of the knit, loop diameter, or the like determines the young's modulus.

This cylindrical bandage 1 is worn over range of the foot side excepting the toe to the ankle, under part at the calf, upper part in the calf, shin, under part in the knee and upper part in the knee as the lower extremity supporter. This cylindrical bandage 1 has the base formation that is formed of the base yarn A and, for example, knitted by the rib stitch that forms the depression and projection formed by knitting the plain stitch and the purl stitch alternately. Thus, this cylindrical bandage 1 has high elastic deformation in such base formation. Additionally, the elastic yarn B is knitted into this base formation, enabling increase in the compression. Consequently, the cylindrical bandage 1 can provide 3 to 70 mmHg in the compression, in which the number of the stitches is reflected.

The wearer may only put on the cylindrical bandage 1 against elasticity of the lengthwise direction of a part of the human body and diameter direction being perpendicular to such lengthwise direction. Thus, no expert can easily and freely put on and taken off the cylindrical bandage 1 with putting any pressure for the lengthwise direction of a part of the human body and, as needed, for diameter direction being perpendicular to such lengthwise direction. This cylindrical bandage 1 permits good convenience such as handling and carrying.

According to the first tubular knit 10 and the second tubular knit 20 of above-mentioned embodiment, the relation between the young's modulus (E) of the stitch row on the circle of the wale side and the young's modulus ($E_0$) of the stitch row of the course side, where the yarn is looped-interknitted, is set to $E \leq E_0$. When the young's modulus (E) of the stitch row on the circle of the wale side is equal to the young's modulus ($E_0$) of the course side, both the wale side and the course side are equal in stretch. When the relation between the young's modulus (E) and the young's modulus ($E_0$) is $E > E_0$, the wearer easily pulls the cylindrical bandage 1 in lengthwise direction of the human body, where the cylindrical bandage 1 is inserted, and it is hard to pull the cylindrical bandage 1 in the extending direction of the diameter of the tube, in which, for example, the leg of the human body is inserted. Conversely, when the relation between the young's modulus (E) and the young's modulus ($E_0$) is $E < E_0$, the wearer easily pulls the cylindrical bandage 1 in the extending direction of the diameter of the tube, in which, for example, the leg of the human body is inserted, and then such pull allows the knit to be stretched. In this case, the wearer puts on the cylindrical bandage 1 with less resistance and handles the cylindrical bandage 1 easily. Thus, it is preferable that the young's modulus ($E_0$) on the course side is larger than the young's modulus (E) of the stitch row on the circle of the wale side. This allows the cylindrical bandage 1 to have less elastic deformation in lengthwise direction of the human body, where the cylindrical bandage 1 is inserted, when the cylindrical bandage 1 is put on and taken off with external force. Consequently, the wearer easily pulls the cylindrical bandage 1 in such lengthwise direction in which the cylindrical bandage 1 is inserted and shifted, and the wearer sifts the cylindrical bandage 1 easily and freely with pressure for such lengthwise direction of the human body. The cylindrical bandage 1 has low elastic deformation in lengthwise direction of the human body in which the cylindrical bandage 1 is inserted, when the cylindrical bandage 1 is put on and taken off with external force. Although the cylindrical bandage 1 has low stretch in such lengthwise direction in which the cylindrical bandage 1 is shifted, the wearer sifts the cylindrical bandage 1 easily and freely with pressure for such lengthwise direction of the human body. The young's modulus(E) of the wale side based on the human body circumference dates $m_1$, $m_2$, $m_3$, . . . , which is in the section being perpendicular to the lengthwise direction of the human body, the human body position dates $L_1$, $L_2$, $L_3$, . . . , determines the resistance that occurs when the human body is inserted into the cylindrical bandage 1. Thus, even the inexperienced wearer puts on the cylindrical bandage 1 easily. In some embodiments, the relation between the young's modulus (E) on the wale side and the young's modulus ($E_0$) on the course side may be set to $E > E_0$.

The cylindrical bandage 1 of the embodiment is formed into the cylindrical shape. The base formation in the first tubular knit 10 and the second tubular knit 20 is formed of the rib stitch or the like. The elastic yarn B is inserted into such base formation. Thus, the cylindrical bandage 1 has large elastic deformation. The cylindrical bandage 1 is difficult to slip off and sift even when the wearer takes exercise.

When the cylindrical bandage 1 is formed into the cylindrical shape by using the no sewing flatbed knitting machine, the cylindrical bandage 1 has no sewing. This yields decrease in stress to the skin. The cylindrical bandage 1 is difficult to lose shape with wash. Such seamless cylindrical bandage 1 has distributed tension and has uniform elasticity in the wale side and provides uniform compression in the wale side. The seamless allows easy deal of all edge of the yarn.

Conventional elastic stockings, which is kitted by the circular knitting machine, have small diameter and high stitch density and high tension of an elastic yarn at the ankle side. Such conventional elastic stockings provide higher compression at the ankle side than at other part. Thus, such conventional elastic stockings need strong force when the conventional elastic stockings are worn, specifically, when the foot part that has the larger circumference of the heel than that of the ankle inserts into the ankle side of the conventional elastic stockings. It is difficult for old people and women with weak force in their fingers to put on such conventional elastic stockings. Additionally, such conventional elastic stockings are easy to create wrinkles at the instep of the foot. Thus, such conventional elastic stockings have bad air permeability at dense stitches. Such elastic stockings have also the problem that nylon knit causes an allergic reaction to the skin.

By contrast, the first tubular knit 10 and the second tubular knit 20 forming the cylindrical bandage 1 correspond to the variation in the section of the human body. Such first tubular knit 10 and second tubular knit 20 have the number of the stitches that approximates the calculation based on the predetermined young's modulus in which the positions as the human body position dates $L_1$, $L_2$, $L_3$, . . . are reflected on the wale side. In the first tubular knit 10 and the second tubular knit 20, the variation in the circumference with the variation in the number of the stitches on the wale side determines any loop diameter. This allows the first tubular knit 10 and the second tubular knit 20 to put predetermined pressure on the user. Additionally, the old people and women with weak force in finger can easily put on and taken off the cylindrical bandage 1 with no excessive force but week force when they apply predetermined force to the cylindrical bandage 1 for the lengthwise direction of a part of the human body and for the perpendicular direction relative to the lengthwise direction as needed. Since no excessive pressure is applied to the cylindrical bandage 1 when the cylindrical bandage 1 is put on and taken off, the cylindrical bandage 1 lasts longer.

In the above-mentioned exemplified embodiment, the knitting-width direction of the stitches equals with the diameter direction of the tube. Inserting elastic yarn B into the rib base formation formed of the base yarn A causes high stretch in the lengthwise direction of the human body and for its perpendicular direction. In the above-mentioned exemplified embodiment, missing the knitting of the elastic yarn B to a part of the rib base formation yields high stretch in the perpendicular direction relative to the lengthwise direction of the human body and allows the knit to have high potential for stretch and the cylindrical bandage 1 to be easily put on and taken off. The knit having week tension has well-hold, provides good feeling with the wear and has high elasticity. Knitting the elastic yarn B into the exterior convex part 42 allows for high elasticity on the wale side. If the elastic yarn B is cut unexpectedly, the effect of the reduction of the tension is small. Alternatively, tucking the elastic yarn A yields high elasticity.

In the cylindrical bandage 1, the variation in the number of the stitches corresponds to the variation in the section along lengthwise direction of the human body. This cylindrical bandage 1 is prevented from having wrinkles at the instep of the foot and providing the concentration of the compression while being worn. This cylindrical bandage 1 can be formed of cotton. Consequently, this cylindrical bandage 1 has good air permeability and is prevented from getting sweaty. This yields good ventilation and less humidity. Such good ventilation allows heat of vaporization with sweat and this yields return-promoting-effect. Use of thick cotton which creates few or no wrinkle yields a range of 3 to 70 mmhg and more in the compression, enabling to cylindrical bandage 1 is easily put on and taken off. The cylindrical bandage 1 fails to lose shape when being repeatedly washed.

Thus, the cylindrical bandage 1 balances the return-promoting-effect and the ventilation.

In this cylindrical bandage 1, the variation in the number of stitches determines the variation in the diameter of the tube. This allows less or no effect on design that is formed by the knitting.

The cylindrical bandage 1 has the first tubular knit 10 and the second tubular knit 20 that have the depression (the exterior convex part 42) and the projection (the interior convex part 41), which each extends in the longitudinal direction (in the course side) contiguously and are alternately arranged in parallel, on the inside being in contact with the wear part. Thus, such first tubular knit 10 and the second tubular knit 20 includes the uneven shape (waveform) in the cross-section, in which the depression and the projection continue in the circumferential direction (in the wale side) on the circle. Such first tubular knit 10 and second tubular knit 20 cover the circumference including the instep side and the malleolus. This enables the first tubular knit 10 and the second tubular knit 20, which include the interior convex part 41 on the inside, to be close contact with even the circumference of the malleolus, where the lymph is easily collected, and to provide extremely high return-promoting-effect.

The cylindrical bandage 1 can provide 15 mmHg and more in the compression at the base part around the malleolus near the heel side of the foot, which it is difficult for conventional elastic stockings to put pressure on, while being worn on the circumference of the ankle joint. This compression is measured under above-mentioned measurement conditions. In the cylindrical bandage 1, the difference in the compression between the instep of the foot and the base part around malleolus near the heel side of the foot is 5 mmHg or less, preferably, 3 mmHg or less, more preferably, 1 mmHg or less. The difference in the compression-distribution between the instep of the foot and the base part around malleolus near the heel side of the foot is 40% or less, preferably, 30% or less, more preferably, 10% or less. Consequently, the knit can fit and be in close contact with even the circumference of the ankle joint, which have a lot of variation in the section, and can provide uniform compression and high return-promoting-effect.

Although high compression provides high return-promoting-effect, high compression may cause, for example, skin damage, skin laceration, or skin tear depending the conditions of the wear part (diseased part) of the wearer. The inventors have verified that less than 3 mmHg in the compression allows no return-promoting-effect and greater than 70 mmHg in the compression may allows prevention of the return promotion.

Thus, a range from 3 to 70 mmHg, preferably, 5 to 60 mmHg in the compression being at the base part around malleolus near the heel side of the foot allows less or no skin damage, skin laceration, and skin tear and yields the return-promoting-effect. More preferably, a range from 15 to 50 mmHg, most preferably, 20 to 45 mmHg in the compression yields high return-promoting-effect and good comfort.

Additionally, even low compression allows high return-promoting-effect because the cylindrical bandage 1 provides the return-promoting-effect that is brought by strength and weakness of the compression derived from the depression and projection (the exterior convex part 42 and the interior convex part 41), which each extends in the longitudinal direction contiguously on the inside of the cylindrical bandage 1 and that matches the flow of lymph.

Thus, the cylindrical bandage 1 has effect on treatment and prevention of localized edemas of disease that has wide range, such as venous (for example, varicose vein, deep vein thrombosis, venous thrombosis after-affect, pulmonary embolism), lymph (for example, incomplete development, lymph node dissection, lymphangitis), any inflammatory, allergy (which is derived from, for example, drugs, plants, bug bites), vascular nerve (for example, Quincke's edema), disused (for example, bedridden state for a long period, paralysis), and aftereffect of trauma or general surgery. This cylindrical bandage 1 can be used as an elastic wear that is general term such as an elastic stocking, an elastic sleeve, or an elastic bandage. In voluntary standard of the industry in Japan, the wear providing 30 mmHg in the compression is treated as the elastic wear.

An elastic cloth, such as an elastic stocking, an elastic sleeve, or an elastic bandage, that works well for treatment and preventing of varicose vein, deep vein thrombosis, pulmonary embolism, and lymphedema has application to medical expenses in accordance with doctor's wearing instructions. However, in some embodiments, the cylindrical bandage 1 may be also used as wearing orthosis for compression used for compression methods that put pressure on the part of the human body, such as a bandage, a supporter, a sleeve, a stocking, or an undershirt, which is formed by fabric clothes having elasticity throughout, or used as a seamless bandage. For example, the cylindrical bandage 1 may be treated as a medical orthosis such as a supporter for the lymphedema or a lower extremity for the varicose vein, or may be used for a cylindrical bandage that puts external pressure on an arm, a leg, a head part, a foot part, a wrist part, or a hand part. The cylindrical bandage 1 is also used for improving and preventing edemas and varicose vein by putting pressure on a necessary part of limb and trunk of the body. In some cases, some kinds of the cylindrical bandage are need for edemas parts of the patient.

The cylindrical bandage 1 is not limited to use as medical orthosis such as supporter for lymphedema and varicose vein. This cylindrical bandage 1 can be used as orthosis for compression such as a bandage, a supporter, a sleeve, a stocking, an undershirt, a sock, and a glove. Such cylindrical bandage 1 provides high effective for prevention and mitigation of tiredness and swelling in daily life and exercise. Additionally, the cylindrical bandage 1 has the depression and projection on the inside. Such depression and projection yields strength and weakness in the compression. This improves blood-circulation-promotion-effect and enhances the effective for prevention and mitigation of tiredness and swelling.

The cylindrical bandage 1 is not only used as compress. For example, the cylindrical bandage 1 can be used as wear for daily life such as a bandage, a supporter, a sleeve, a stocking, an undershirt, a sock, and a glove.

The cylindrical bandage 1 achieves high close contact and the cylindrical bandage 1 has good breathability, good texture and touch for skin, and good cushion with cotton yarn. Thus, such cylindrical bandage 1 is good for a cushioning that is worn under and inside (near skin) of a compress such as a common elastic stocking. When the cylindrical bandage 1 is worn on the part of the human body along the lengthwise direction of the human body and the compress such as the common elastic stocking is worn on this cylindrical bandage 1, return-promoting-effect by the compress such as the common elastic stocking increases. The cylindrical bandage 1 formed of a cotton yarn has high prevention and protection for pain, skin damage, skin laceration and skin tear.

The cylindrical bandage 1 of the above-mentioned embodiment covers over from a foot side excluding toes to a thigh part as the supporter for lower extremity. In some embodiments, the cylindrical bandage 1 may cover over from the instep part or the sole part to the ankle in the foot, from the instep part or the sole part to the below of the knee in the foot, or from the instep part or the sole part to the waist part in the foot. Alternatively, the cylindrical bandage 1 may cover toes of the foot. For example, bottom end part of the second tubular knit 20 is formed into an arch shape like as the socks or has five toes like as the five toes socks by narrowing and widening and then closing edge with casting off. This forms the cylindrical bandage 1 that covers the toes of the foot. The cylindrical bandage 1 is not limited to use for covering the lower extremity. For example, the cylindrical bandage 1 may cover an arm, a hand, or a wrist. The cylindrical bandage 1 covering arm can fit bending part of the olecranon and be close contact with elbow joint. This yields strong circulation inducement effect.

The cylindrical bandage 1 of the above-mentioned embodiment is worn on the leg part and the foot part as the object of the wear. In this cylindrical bandage 1, the first tubular knit 10 is knitted on the basis of the human body position dates $L_1, L_2, L_3, \ldots L_6, L_7$, which are as the length of the leg, and the human body circumference dates $m_1, m_2, m_3, \ldots m_6, m_7$, which are the circumference of the section being perpendicular to the human body position dates $L_1, L_2, L_3, \ldots L_6, L_7$. The second tubular knit 20 is knitted on the basis of the human body position dates $(L_8), L_9, L_{10}$, which are as length of the foot, and the human body circumference dates $(m_8), m_9, m_{10}$, which are the circumference of the section being perpendicular to the human body position dates $(L_8), L_9, L_{10}$. Additionally, the connecting knit 30 connects these first tubular knit 10 and second tubular knit 20 by increasing the number of the course, where the yarn is interknitted into the loops, between the human body position date $L_7$ and the human body position date $L_9$ to correspond to the shape of the heel. This allows the connecting knit 30 to include a curvature corresponding to the bulge of the heel.

However, in some embodiments, the cylindrical bandage 1 may have no distinction between the first tubular knit 10 and the second tubular knit 20 and have no connecting knit 30 having curve depending on purpose or wear part (for example, the arm, the leg, the head, the foot, or the hand). That is, the cylindrical bandage 1 may be knitted by continuing around knitting in the longitudinal direction without above-mentioned going around and return of knitting repeatedly. All the cylindrical bandage 1 putting desired pressure is set to the number of the stitches that approximates the calculation based on the human body circumference dates $m_1, m_2, m_3, \ldots$, which is the circumference in the section being perpendicular to the human body position dates $L_1, L_2, L_3, \ldots$, and based on the predetermined young's modulus in which the positions of the human body position dates $L_1, L_2, L_3, \ldots$ are reflected. This number of the stitches forms the stitch row on the circle of the wale side in the cylindrical bandage 1. Thus, the cylindrical bandage 1 may be formed into a straight line in the longitudinal direction throughout.

As mentioned above, the first tubular knit 10 and the second tubular knit 20 following it in the cylindrical bandage 1 of above-mentioned embodiment are knitted by using the human body position dates $L_1, L_2, L_3, \ldots$, which are determined as the lengthwise direction of a part of the human body being the object of the wear, and the human body circumference dates $m_1, m_2, m_3, \ldots$, which is the circumference in the section being perpendicular to the human body position dates $L_1, L_2, L_3, \ldots$. Such human body circumference dates $m_1, m_2, m_3, \ldots$, which is the circumference in the section being perpendicular to the human body position dates $L_1, L_2, L_3, \ldots$ along the lengthwise direction of the human body, are used for knitting the base formation as the number of the stitches of the stitch row on the wale side. In particular, such number of the stitches is set to the number of the stitches that approximates the calculation based on the human body circumference dates $m_1, m_2, m_3, \ldots$ with the predetermined young's modulus in which the positions of the human body position dates $L_1, L_2, L_3, \ldots$ are reflected. Such first tubular knit 10 and second tubular knit 20 are knitted by weft knitting.

This cylindrical bandage 1 of above-mentioned embodiment is worn on a part of the human body along the lengthwise of the part of the human body. This cylindrical bandage 1 of above-mentioned embodiment has the first tubular knit 10 and the second tubular knit 20 following it, which both are knitted by using the human body position dates $L_1, L_2, L_3, \ldots$, which are determined as the lengthwise direction of a part of the human body being the object of the wear, and using the human body circumference dates $m_1$, $m_2, m_3, \ldots$, which are the circumference of the section being perpendicular to the human body position dates $L_1, L_2, L_3, \ldots$. These first tubular knit 10 and the second tubular knit 20 have the number of the stitches that approximates the calculation based on the predetermined young's modulus in which the human body circumference dates $m_1, m_2, m_3, \ldots$ are reflected. Such number of the stitches on the one circle forms the stitch row on the one circle of the wale side in the first tubular knit 10 and the second tubular knit 20. Thus, this cylindrical bandage 1 is designed so as to be correspond to the human body circumference dates $m_1, m_2, m_3, \ldots$ including the variation in the circumference of the section of the human body by increasing and decreasing the number of the stitches of the stitch row on the one circle of the wale side. This cylindrical bandage 1 includes the depression part (which is the exterior convex part 42 formed of the stitch showing the convexity on the outside and the concavity on the inside) and the projection parts (which is the interior convex part 41 formed of the stitch showing the concavity on the outside and the convexity on the inside) on the inside, which is brought into contact with the wear part, by knitting. Such depression part and projection part each extends contiguously in the longitudinal direction (the course direction) and are alternatively arranged in parallel. Thus, the first tubular knit 10 and the second tubular knit 20 are formed into the uneven shape in the cross-section on the inside, where the depression and projection continue in the circumferential direction of the circle (on the wale side).

The cylindrical bandage 1 of above-mentioned embodiment has the variation in the number of the stitches of the stitch row on the one circle of the wale side, and the variation in the circumference accordingly to match the variation in the section of the human body in the human body circumference dates $m_1, m_2, m_3, \ldots$ that is the circumference in the section being perpendicular to the human body position dates $L_1, L_2, L_3, \ldots L_6, L_7$, which are in the lengthwise direction of a part of the human body, the object of the wear. The cylindrical bandage 1 includes the depression part and the projection part, which are alternatively arranged in parallel and are formed by knitting, on the inside. Thus, such cylindrical bandage 1 includes the uneven shape in the cross-section in which the depression and projection continue in the circumferential direction, which is perpendicular to the longitudinal direction.

Above-mentioned human body circumference dates $m_1, m_2, m_3, \ldots$ are the circumference of the section being perpendicular to the human body position dates $L_1, L_2, L_3, \ldots$. Such human body circumference dates $m_1, m_2, m_3, \ldots$ are used as the dates including the variation in the circumference of the human body and thus used for determination of the length of the stitch row on the one circle of the wale side.

The variation in the section of the human body in the human body circumference dates $m_1, m_2, m_3, \ldots$ with the variation in the number of the stitches of the stitch row on the one circle of the wale side, where the yarn forming the stitches continues, is the adjustment of the circumference with the variation in the number of the stitches of the stitch row on the one circle of the wale side to achieve the predetermined young's modulus, in which the human body circumference dates $m_1, m_2, m_3, \ldots$ are reflected, and thus correspondent to the variation in the circumference of the section of the human body. That is, variation in the number of the stitches that approximates the calculation based on the predetermined young's modulus, in which the human body position dates $L_1, L_2, L_3, \ldots$ are reflected, adjusts the circumference.

Since the stitch row on the one circle of the wale side is set to the number of the stitches that approximates the calculation using the predetermined young's modulus, in which the human body position dates $L_1, L_2, L_3, \ldots$ are reflected, the increase and decrease in the number of the stitches of the stitch row on the one circle of the wale side, where the yarn forming the stitches continues, corresponds to the variation in the circumference of the human body in the human body circumference dates $m_1, m_2, m_3, \ldots$.

That is, the number of the stitches determine the circumference to correspond to the variation in the human body circumference dates $m_1, m_2, m_3, \ldots$, which is in the section being perpendicular to the human body dates $L_1, L_2, L_3, \ldots$, and to achieve the predetermined young's modulus in which the human body circumference dates $m_1, m_2, m_3, \ldots$ are reflected.

The determination of the number of the stitches on the circle forming the stitch row on the one circle of the wale side means determining the number of the stitches that approximates the calculation calculated to achieve the predetermined young's modulus, in which the positions (parts of the human body) such as the human body position dates $L_1, L_2, L_3, \ldots$ are reflected. This calculation providing the number of the stitches may be round off to the nearest whole number, or round up, or round down. The physical property of the yarn, means of the knitting, or characteristics of the wear part in the body determines such rounding off, rounding up, or rounding down. Thus, the human body circumference dates $m_1, m_2, m_3, \ldots$ can be expressed as the number of the stitches that approximates the calculation. The approximation includes the calculation error within 1 in the number of the stitches.

Thus, the cylindrical bandage 1 of the embodiment is flatbed-knitted by using a flatbed knitting machine. The first tubular knit 10 and the second tubular knit 20 following it include the variation in the number of the stitches of the stitch row on the circle of the wale side along the longitudinal direction in accordance with the variation in the section of the human body. This allows the cylindrical bandage 1 to correspond to the difference in dimensions and shapes of the section along the lengthwise of the human body. The variation in the number of the stitches with the variation in the section of the human body enables a lot of expression in the dimensions and shapes and enables determination of a freely-selected circumference. Additionally, it is easy to determine the best diameter corresponding to the dimension sand shapes of the section of the human body. The number of the stitches allows for determination of desired compression easily.

Consequently, the cylindrical bandage 1 can fit the circumference of the ankle joint, which includes a lot of variation in dimensions and shapes of the section, very well. This cylindrical bandage 1 is prevented from having slack and wrinkles and tightness with excess or short of the knit. This cylindrical bandage 1 allows the knit to fit even the depression around the malleolus, specifically, the depression in the rear side of the malleolus near the heel side. This cylindrical bandage 1 provides uniform compression-distribution and steady compression. Additionally, this cylindrical bandage 1 can be in close contact with the ruggedness caused by localized edemas and the like. This cylindrical bandage 1 has the variation in the number of the stitches, and the circumference and can provide desired compression accordingly. This allows the cylindrical bandage 1 to have freely-selected loop, to have air permeability, and to be put on the human body easily.

The cylindrical bandage 1 is not limited to seamless cylindrical knitting that uses a wholegarment flatbed knitting machine. In some embodiments, the cylindrical bandage 1 may be formed into cylindrical shape by sewing and be formed by a computer control, manual control, machine-knitting, or hand-knitting.

The first tubular knit 10 and the second tubular knit 20 of the cylindrical bandage 1 of above-mentioned embodiment include the depression part (which is the exterior convex part 42 formed of the stitch showing the convexity on the outside and the concavity on the inside) and the projection part (which is the interior convex part 41 formed of the stitch showing the concavity on the outside and the convexity on the inside) on the inside brought into contact with the wear part. Such depression part and projection part extend in the longitudinal direction contiguously and are alternatively arranged in parallel in the circumferential direction. Thus, the first tubular knit 10 and the second tubular knit 20 include the uneven shape in the cross-section on the inside, where the depression and projection continue in the circumferential direction on the circle. These depression and projection yields strong compression and weak compression in the circumferential direction being perpendicular to the longitudinal direction of the wearer while the cylindrical bandage 1 is worn. This partial compression allows improvement of the flow of the lymph and the return-promoting-effect. Since these depression and projection extend in the longitudinal direction contiguously, the strong compression and the weak compression run along the flow direction of the lymph and the venous. This allows more improvement of the flow of the lymph and the return-promoting-effect. Thus, the wearer is under well-balanced pressure and feels no strange. Since the first tubular knit 10 and the second tubular knit 20 including the depression and the projection on the inside has the variation in the surface, the knit fits and is in close contact with the shape of the bending part or curvature part that has the variation in the circumference of the section of the human body.

Thus, the cylindrical bandage 1 provides high fitness corresponding to the variation in the dimensions and shapes in the section of the human body. Additionally, the knit that is brought into fit for the wear part includes the depression part and the projection part that each extends in the longitudinal direction contiguously and that are alternatively arranged in parallel in the circumferential direction on the circle. Thus, the knit are formed into the uneven shape, where the depression and the projection continue in the cross-section on the circle. This enhances the return-promoting-effect and yields high return-promoting-effect.

In the cylindrical bandage 1 of above-mentioned embodiment, the elastic yarn B is knitted into the stitch forming the exterior convex part 42 in the base formation formed of the rib stitch using the base yarn A. At the same time, the elastic yarn B misses knitting the stitch forming the interior convex part 41 or is tucked to the stitch forming the interior convex part 41. Thus, the elastic yarn B is inserted at predetermined interval on the course. Consequently, the tension with the circle is higher on the outside, which is a reverse of the inside, than on the inside, which is in close contact with the wear part. That is, above-mentioned includes this invention: the cylindrical bandage 1 has the tension with the circle that is higher on the outside being a reverse of the inside than on the inside brought into contact with the wear part.

This allows clearer distinction between the projection part (which is the interior convex part 41 formed of the stitch showing the convexity on the inside and the concavity on the outside) and the depression part (which is the exterior convex part 42 formed of the stitch showing the concavity on the inside and the convexity on the outside). Additionally, the interior convex part 41 on the inside, which is brought into contact with the wear part, has the curvature and increases in the volume to the thickness direction. This enables the interior convex part 41 to be contact with the wear part more closely or more widely, increasing the compression.

In the cylindrical bandage 1 of above-mentioned embodiment, the elastic yarn B is cross-knitted into the rib stitch formation using the base yarn A by knitting and missing, knitting and tucking or both. Consequently, the cylindrical bandage 1 has the variation in the tension on the circumferential direction and has the difference in the tension between the projection part (which is the interior convex part 41 formed of the stitch showing the convexity on the inside and the concavity on the outside) and the depression part (which is the exterior convex part 42 formed of the stitch showing the concavity on the inside and the convexity on the outside) on the inside, which is brought into contact with the wear part. That is, above-mentioned includes this invention: the cylindrical bandage 1 has difference in tension between the projection part and the depression part on the inside brought into contact with the wear part.

This allows clearer distinction between the projection part (which is the interior convex part 41 formed of the stitch showing the convexity on the inside and the concavity on the outside) and the depression part (which is the exterior convex part 42 formed of the stitch showing the concavity on the inside and the convexity on the outside). Additionally, the interior convex part 41 on the inside, which is brought into contact with the wear part, has the curvature and increases in the volume to the thickness direction. This enables the interior convex part 41 to be contact with the wear part more closely or widely, further increasing the compression.

The cylindrical bandage 1 of above-mentioned embodiment includes this invention: the first tubular knit 10 and the second tubular knit 20 include the base formation formed of the rib stitch. These first tubular knit 10 and second tubular knit 20 include the depression part and the projection part that are formed of the exterior convex part 42 and the interior convex part 41, which each extends contiguously in the longitudinal direction on the inside and outside of the knit and are alternately arranged in parallel. Thus, such first tubular knit 10 and second tubular knit 20 are formed into corrugated shape in outline of the cross-section, where the depression and the projection continue in circumferential direction on the circle. In these first tubular knit 10 and second tubular knit 20, the stitch showing the convexity on the inside, which is brought into contact with the wear part, shows the concavity on the outside, which is the reverse of the inside. At the same time, the stitch showing the concavity on the inside, which is brought into contact with the wear part, shows the convexity on the outside, which is the reverse of the inside. This cylindrical bandage 1 has the interior convex part 41 whose outline in the section approximates more curved line than an outline of the exterior convex part 42 one, when the stitch showing the convexity on the inside, which is brought into contact with the wear part, and the concavity on the outside, which is the reverse of the inside, is defined as the interior convex part 41 and the stitch showing the concavity on the inside, which is brought into contact with the wear part, and the convexity on the outside, which is the reverse of the inside, is defined as the exterior convex part 42.

The cylindrical bandage 1 of above-mentioned embodiment is worn on a part of the human body along the lengthwise direction of the part of the human body. In this cylindrical bandage 1, the first tubular knit 10 and the second tubular knit 20 following it are knitted by using the human body position dates $L_1, L_2, L_3, \ldots$, which are determined as the lengthwise direction of a part of the human body being the object of the wear, and using the human body circumference dates $m_1, m_2, m_3, \ldots$, which are the circumference of the section being perpendicular to the human body position dates $L_1, L_2, L_3, \ldots$. These first tubular knit 10 and second tubular knit 20 have the number of the stitches that approximates the calculation based on the predetermined young's modulus in which the human body circumference dates $m_1, m_2, m_3, \ldots$ are reflected. Such number of the stitches on the circle forms the stitch row on the one circle of the wale side in the first tubular knit 10 and the second tubular knit 20. Thus, The cylindrical bandage 1 has increase and decrease in the number of the stitches of the stitch row on the one circle of the wale side to correspond to the variation in the circumference of the human body in the human body circumference dates $m_1, m_2, m_3, \ldots$. Additionally, the first tubular knit 10 and the second tubular knit 20 include the depression and the projection that each extends contiguously in the longitudinal direction on the inside and outside of the knit and that are alternately arranged in parallel. Thus, such first tubular knit 10 and second tubular knit 20 are formed into corrugated shape in the outline of the cross-section, where the depression and the projection continue in circumferential direction on the circle. In these first tubular knit 10 and second tubular knit 20, the stitch showing the convexity on the inside, which is brought into contact with the wear part, shows the concavity on the outside, which is the reverse of the inside. At the same time, the stitch showing the concavity on the inside, which is brought into contact with the wear part, shows the convexity on the outside, which is the reverse of the inside. This cylindrical bandage 1 has the interior convex part 41 that has more curved outline in the cross-section than the exterior convex part 42 one, when the stitch showing the convexity on the inside, which is brought into contact with the wear part, and the concavity on the outside, which is the reverse of the inside, is defined as the interior convex part 41 and the stitch showing the concavity on the inside, which is brought into contact with the wear part, and the convexity on the outside, which is the reverse of the inside, is defined as the exterior convex part 42.

In the cylindrical bandage 1 of above-mentioned embodiment, the first tubular knit 10 and the second tubular knit 20 include the variation in the number of the stitches of the stitch row on the circle of the wale side along the longitudinal direction in accordance with the variation in the section of the human body. This allows the cylindrical bandage 1 to correspond to the difference in dimensions and shapes of the section along the length of the human body. The variation in the number of the stitches in accordance with the variation in the section of the human body enables a lot of expression in the dimensions and shapes and allows for determination of a freely-selected circumference. Additionally, it is easy to determine the best diameter corresponding to the dimensions and shapes of the section of the human body. The number of the stitches and young's modulus allows for determination of desired compression easily. Consequently, the cylindrical bandage 1 can fit the circumference of the ankle joint, which have a lot variation in dimensions and shapes of the section, very well, when the cylindrical bandage 1 is worn on, for example, the foot, the leg, or both. This cylindrical bandage 1 is prevented from having slack and wrinkles and tightness with excess or short of the knit. This cylindrical bandage 1 allows the knit to fit even the depression around the malleolus. This cylindrical bandage 1 also provides uniform compression-distribution and steady compression. Additionally, this cylindrical bandage 1 can be in close contact with ruggedness with localized edemas and the like. This cylindrical bandage 1 has the variation in the number of the stitches and the circumference and thus can provide desired compression. This allows the cylindrical bandage 1 to have freely-selected loop, to have air permeability and to be put on the human body easily.

Such cylindrical bandage 1 has the depression part and projection part that are formed of the exterior convex part 42 and the interior convex part 41, which extend contiguously in the longitudinal direction on the inside and outside of the knit and alternately arranged in parallel by the knitting. Thus, cylindrical bandage 1 includes corrugated shape in outline of the cross-section, where the depression and the projection continue in circumferential direction. Such depression and projection yields partial high compression (pressure) and thus strong compression and weak compression in the circumferential direction being perpendicular to the longitudinal direction of the wearer while the cylindrical bandage 1 is worn. This improves the flow of the lymph and enhances return-promoting-effect. Since the depression and projection each extends in the longitudinal direction contiguously, the strength compression and the weakness compression match the flow direction of the lymph and the venous. This improves the flow of the lymph and the return-promoting-effect further. Additionally, the wearer is under well-balanced pressure and feels no strange.

In the cylindrical bandage 1, the elastic yarn B is knitted to the stitches forming the exterior convex part 42 in the base formation formed of the rib stitch using the base yarn A. At the same time, the elastic yarn B misses knitting the stitch forming the interior convex part 41 or is tucked to the stitch forming the interior convex part 41. Thus, the elastic yarn B is inserted at the predetermined interval on the course. Consequently, the interior convex part 41 includes larger curve than exterior convex part 42 one and thus formed into an arch shape or nearly arch shape. This enables the interior convex part 41 to have high cushioning and elasticity and to be in contact with the wear part more closely or widely and to provide higher compression. Since the knit including the depression and the projection on the inside has the variation in the surface, the knit very fits and is in closer contact with the shape of the bending part that has the variation in the circumference of the section of the human body.

Thus, the cylindrical bandage 1 achieves high fitness corresponding to the variation in the dimensions and shapes of the section of the human body. Additionally, the knit that is brought into fit for the wear part includes the depression part and the projection part that each extends in the longitudinal direction and that are alternately arranged in parallel. Thus, the knit is formed into the uneven shape in the cross-section, where the depression and the projection continue in the circumferential direction. This enhances the return-promoting-effect and yields high return-promoting-effect.

The cylindrical bandage 1 of above-mentioned embodiment has the first tubular knit 10, the second tubular knit 20 following the first tubular knit 10, and the connecting knit 30 that is formed by increasing the number of the stitches on the course side, where the yarn is loop-interknitted, between the first tubular knit 10 and the second tubular knit 20 and thus connects the first tubular knit 10 and the second tubular knit 20. The diameter of the circle of the endmost part of the second tubular knit 20, where the endmost part follows the first tubular knit 10 and the connecting knit 30, is larger than the diameter of the circle of the endmost part of the first tubular knit 10, where the endmost part is followed by the second tubular knit 20 and the connecting knit 30. In the connection between the connecting knit 30, the first tubular knit 10, and the second tubular knit 20, the length a of the virtual perpendicular line $c_1$, which runs from the border P between the first tubular knit 10, the second tubular knit 20, and the connecting knit 30 to the symmetrical line $d_1$ where the first tubular knit 10 is followed by the second tubular knit 20 in the front side, and the length b of the virtual perpendicular line $c_2$, which runs from the border P to the symmetrical line $d_2$ in the rear side, are in the ratio 6:4 a:b 9:1. This occurs when the cylindrical bandage 1 is folded to bring the inside of the tube into the contact with the other opposite inside of the tube such that the stitch row on the one circle of the wale side is divided into half at symmetrical line $d_1$ in the front side and the symmetrical line $d_2$ in the rear side.

In the cylindrical bandage 1 of above-mentioned embodiment, the diameter of the one circle and the circumference on the wale side of the endmost part (top end part) that is in the second tubular knit 20 and follows the first tubular knit 10 is larger than the diameter of the one circle and the circumference on the wale side of the endmost part (bottom end part) that is in the first tubular knit 10 and follows the second tubular knit 20. That is, the endmost part (top end part) of the second tubular knit 20 has larger diameter than the endmost part (bottom end part) of the first tubular knit 10 one.

In the cylindrical bandage 1, the first tubular knit 10 and the second tubular knit 20 have the variation in the circumference with the variation in the number of the stitches. This variation in the number of the stitches allows the diameter that follows the first tubular knit 10 and the connecting knit 30 in the second tubular knit 20 to be larger than the diameter that follows the second tubular knit 20 and the connecting knit 30 in the first tubular knit 10. In some embodiments, for example, loop-diameter, means of knitting, or tension may also adjust such diameter.

In connection between these first tubular knit 10 and second tubular knit 20 in the cylindrical bandage 1 of above-mentioned embodiment, the course, where the yarn is loop-interknitted, has increase in number between the first tubular knit 10 and the second tubular knit 20, where the diameter (the circumference) widens from the first tubular knit 10 toward the tubular knit 20. This forms the connecting knit 30 and this connecting knit 30 connects the first tubular knit 10 and the second tubular knit 20.

This connecting knit 30 follows the first tubular knit 10 and the second tubular knit 20, particularly, so that the length a of the virtual perpendicular line $c_1$, which runs from the border P between the first tubular knit 10, the second tubular knit 20, and the connecting knit 30 to the symmetrical line $d_1$ where the first tubular knit 10 is followed by the second tubular knit 20 in the front side, and the length b of the virtual perpendicular line $c_2$, which runs from the border P to the symmetrical line $d_2$ in the rear side and the connecting knit 30 side, are in the ratio 6:4≤a:b≤9:1. This occurs when the cylindrical bandage 1 is folded at the symmetrical line $d_1$ in the front side and the symmetrical line $d_2$ in the rear side such that its circumference on the wale side is divided into half and thus one of the insides of the tube touches the other opposite inside.

Thus, in the cylindrical bandage 1 of above-mentioned embodiment, the diameter of the one circle and the circumference on the wale side at the endmost part (top end part) that is in the second tubular knit 20 and follows the first tubular knit 10 is larger than the diameter of the one circle and the circumference on the wale side at the endmost part (bottom end part) that is in the first tubular knit 10 and follows the second tubular knit 20. Additionally, the connecting knit 30 connects the first tubular knit 10 and the second tubular knit 20 by increasing the number of the course between the first tubular knit 10 and the second tubular knit 20. Thus, the connecting knit 30 includes the curvature. Consequently, the cylindrical bandage 1 is prevented from having wrinkles at the rear side of the ankle and tightness at the heel side and fits the outline of the heel while the cylindrical bandage 1 is worn and covers the circumference of the ankle joint. In the connection part between the first tubular knit 10 and the second tubular knit 20, the second tubular knit 20 has larger diameter than the first tubular knit 10 one and thus the cylindrical bandage 1 has the variation in the diameter between the first tubular knit 10 and the second tubular knit 20. This allows the connecting knit 30 connecting the first tubular knit 10 and the second tubular knit 20 to have enough big curvature corresponding to the bulge of the heel, enabling the knit to have little or no tight fit with the wear. Since the second tubular knit 20 has larger diameter than the first tubular knit 10 one in the connection between the first tubular knit 10 and the second tubular knit 20, the diameter is freely-selected. This enables design and select of the best diameter in accordance with the dimensions and shapes of the circumference of the ankle joint. Thus, the cylindrical bandage 1 is prevented from having slack and wrinkles with excessive knit at the instep side of the foot, and thus prevented from stopping the return with horizontal wrinkles cutting into the skin. Additionally, the cylindrical bandage 1 is prevented from having tightness with short knit at the heel side.

The length a of the virtual perpendicular line $c_1$, which runs from the border P between the first tubular knit 10, the second tubular knit 20, and the connecting knit 30 to the symmetrical line $d_1$ where the first tubular knit 10 is followed by the second tubular knit 20 in the front side, and the length b of the virtual perpendicular line $c_2$, which runs from the border P to the symmetrical line $d_2$ in the rear side and the connecting knit 30 side, are in the ratio 6:4≤a:b≤9:1 in a state where the cylindrical bandage 1 is folded such that its circumference on the wale side is divided into half at the symmetrical line $d_1$ in the front side and the symmetrical line $d_2$ in the rear side and thus one of the insides of the tube touches the other opposite inside. Consequently, not the connecting knit 30, which is formed by increasing the number of the course where the yarn is loop-knitted between the first tubular knit 10 and the second tubular knit 20 and thus includes curvature, but the first tubular knit 10 and the second tubular knit 20, which have the predetermined young's modulus and provides uniform compression, cover the circumference of the malleolus (the medial malleolus and the lateral malleolus).

Thus, the cylindrical bandage 1 is prevented from having slack and wrinkles at the instep of the foot and tightness at the heel side while being worn. In this cylindrical bandage 1, the first tubular knit 10 and the second tubular knit 20 with no curve and bulge cover the ruggedness in the circumference of the malleolus part. Consequently, the cylindrical bandage 1 is prevented from having the rising knit at the depression in the circumference of the malleolus part and thus fits and be in close contact with the curvature part in the circumference of the malleolus part. In particular, this cylindrical bandage 1 is in close contact with even the depression in the rear side of the malleolus and provides steady compression. Additionally, this cylindrical bandage 1 is in close contact with the ruggedness with localized edemas and the like.

The cylindrical bandage 1, therefore, can provide high fitness, uniform compression-distribution, and steady compression at even the circumference of the ankle joint, which has curvature or bent part, such as, the heel part, the malleolus part, and border part between the bottom end of the ankle and the instep part and has a lot of variation in dimensions and shapes in the section.

In the connection between the connecting knit 30 and the first tubular knit 10 and the second tubular knit 20, the connecting knit 30 follows 20 to 40% of the circumference on the wale side at the endmost part, which follows the second tubular knit 20 and the connecting knit 30, of the first tubular knit 10. Additionally, the connecting knit 30 follows 20 to 40% of the circumference on the wale side at the endmost part, which follows the first tubular knit 10 and the connecting knit 30, of the second tubular knit 20. This allows the first tubular knit 10 and the second tubular knit 20 to be prevented from being pulled and stretching at the heel side and thus to be prevented from having tightness with excessive tension and to have no slack, thus enabling closer touch to the ruggedness in the circumference of the malleolus part while the cylindrical bandage 1 is worn and covers the circumference of the ankle joint.

Additionally, the cylindrical bandage 1 of above-mentioned embodiment 1 includes the depression part (which is the exterior convex part 42 formed of the stitch showing the convexity on the outside and the concavity on the inside) and the projection part (which is the interior convex part 41 formed of the stitch showing the concavity on the outside and the convexity on the inside) on the inside that is brought into contact with the wear part while the cylindrical bandage 1 is worn on, for example, the circumference of the ankle joint. These depression part and projection part extend contiguously in the longitudinal direction, where the yarn is loop-interknitted, and are alternatively arranged in parallel. Thus, the first tubular knit 10 and the second tubular knit 20 are formed into the uneven shape in the cross-section on the inside, where the depression and projection continue in the circumference of the circle. Such first tubular knit 10 and second tubular knit 20 can cover over from the instep to the malleolus in the foot and be in close contact with the curvature near the malleolus, particularly, even the curvature in the rear side of the malleolus. This yields high return-promoting-effect. That is, the first tubular knit 10 and the second tubular knit 20 can be brought into close contact with the curvature near the malleolus, and provide high compression and high return-promoting-effect accordingly, while the cylindrical bandage 1 is worn. These first tubular knit 10 and second tubular knit 20, which are brought into close contact with the curvature near the malleolus, include the depression part (which is the exterior convex part 42 formed of the stitch showing the convexity on the outside and the concavity on the inside) and the projection part (which is the interior convex part 41 formed of the stitch showing the concavity on the outside and the convexity on the inside) that extend contiguously in the longitudinal direction on the inside. Such depression part and projection part are alternately arranged in parallel. Therefore, the circulation of the lymph at the circumference of the malleolus, where the lymph is easily collected, improves and the circulation inducement effect increases further.

Although above-mentioned embodiment exemplifies that the cylindrical bandage 1 is worn on the lower extremity of the human body as a supporter for the lower extremity, the cylindrical bandage 1 is not limited to be worn on the foot part and the leg part. In some embodiments, the cylindrical bandage 1 may be used as a bandage, a supporter, a sleeve (an elastic sleeve), or a glove (an elastic glove) that is worn on limb and trunk of the body, for example, an arm, a wrist, or a hand, or is worn on a head. For example, the cylindrical bandage 1 may have a hole, which is formed by cutting and tearing the knit, in the connecting part having the difference in the diameter of the circle between the first tubular knit 10 and the second tubular knit 20. This allows use for the wear of a wrist or a hand part. Such cylindrical bandage 1 that includes the hole for a thumb and the first tubular knit 10 covering the hand side and the second tubular knit 20 covering the wrist side can correspond to the variation in the section of the hand and thus fit hand.

DESCRIPTION OF SYMBOLS

1 cylindrical bandage
10 first tubular knit
20 second tubular knit
30 connecting knit
41 interior convex part
42 exterior convex part
$L_1, L_2, L_3, \ldots$ the human body position dates
P border part between first tubular knit, second tubular knit, and connecting knit
$c_1, c_2$ virtual perpendicular line
$d_1, d_2$ symmetrical line
A base yarn
B elastic yarn

The invention claimed is:

1. A cylindrical bandage for wearing on a wear part of a human body along a longitudinal direction of the wear part of the human body, the cylindrical bandage including:
   depression parts formed by rib knitting; and
   protrusion parts formed by rib knitting,
   wherein the cylindrical bandage has a variation in a circumference corresponding to a variation in a number of stitches of a stitch row on one circle of a wale side, the variation in the circumference corresponding to a variation in a section of the wear part of the human body, the wale side having a continuous yarn forming the stitches,
   wherein the depression parts and the protrusion parts form an uneven shape in a cross-section on an inside brought into contact with the wear part of the human body,
   wherein each of the depression parts and each of the protrusion parts are arranged alternately and continuously around an entire circumference of the cylindrical bandage perpendicular to a longitudinal direction of the cylindrical bandage, and
   wherein each of the depression parts and each of the protrusion parts extend in the longitudinal direction of the cylindrical bandage.

2. A cylindrical bandage according to claim 1, wherein tension of a circle on a circumferential direction, which is perpendicular to the longitudinal direction of the cylindrical bandage, is larger on an outside being a reverse of the inside than on the inside brought into contact with the wear part of the human body.

3. A cylindrical bandage as claimed in claim 1, wherein each of the depression parts and each of the protrusion parts on the inside brought into contact with the wear part of the human body are different in tension of a circle on a circumferential direction perpendicular to the longitudinal direction of the cylindrical bandage.

4. A cylindrical bandage for wearing on a wear part of a human body along a longitudinal direction of the wear part of the human body, the cylindrical bandage including:
an exterior convex part comprising a stitch showing a concavity on an inside of a knit that is brought into contact with the wear part of the human body and a convexity on an outside being a reverse of the inside, the exterior convex part forming depression parts and protrusion parts; and
an interior convex part comprising a stitch showing a convexity on the inside brought into contact with the wear part of the human body and a concavity on the outside being the reverse of the inside, the interior convex part forming depression parts and protrusion parts, the interior convex part having an outline of a cross-section being closer curved line than an outline of the cross-section of the exterior convex part,
wherein the cylindrical bandage has a variation in a circumference corresponding to a variation in a number of stitches of a stitch row on one circle of a wale side, the variation in the circumference corresponding to a variation in a section of the wear part of the human body, the wale side having a continuous yarn forming the stitches,
wherein the exterior convex part and the interior convex part form an uneven shape in a cross-section on the outside and the inside of the cylindrical bandage, respectively, the uneven shape including the depression parts and the protrusion parts of the exterior convex part and the interior convex part, respectively, that are formed by rib knitting,
wherein each of the depression pans and each of the protrusion parts of the exterior convex part and the interior convex part, respectively, are arranged alternately and continuously around an entire circumference of the cylindrical bandage perpendicular to a longitudinal direction of the cylindrical bandage, and
wherein each of the depression parts and each of the protrusion parts of the exterior convex part and the interior convex part, respectively, extend in the longitudinal direction of the cylindrical bandage.

5. A cylindrical bandage as claimed in claim 4, wherein a thickness of the knit is within a range of 2 mm to 15 mm.

6. A cylindrical bandage as claimed in claim 1, wherein a compression at a base part around a lateral malleolus part near a heel side of a foot is within a range from 3 mmHg to 70 mmHg while the cylindrical bandage is worn on a circumference of an ankle joint of the human body.

7. A cylindrical bandage as claimed in claim 1, wherein a difference in a compression between a base part around a lateral malleolus part near a heel side of a foot and an instep part of the foot is 40% or less while the cylindrical bandage is worn on a circumference of an ankle joint of the human body.

8. A cylindrical bandage comprising:
a first tubular knit;
a second tubular knit following the first tubular knit; and
a connecting knit connecting the first tubular knit and the second tubular knit with increase in a number of stitches on a course side between the first tubular knit and the second tubular knit, the course side having a yarn loop-interknitted,
wherein a diameter of a circle of an endmost part of the second tubular knit is larger than a diameter of a circle of an endmost part of the first tubular knit, the circle of the endmost part of the second tubular knit comprising a stitch row on one circle of a wale side and following the first tubular knit and the connecting knit, the circle of the endmost part of the first tubular knit comprising a stitch row on one circle of the wale side and following the second tubular knit and the connecting knit, the wale side having a continuous yarn forming the stitches, and
a length (a) of a virtual perpendicular line and a length (b) of a virtual perpendicular line are in a ratio 6:4≤(a):(b) ≤9:1 in a state where the cylindrical bandage is folded along a symmetrical line of the first tubular knit and the second tubular knit to divide a circumference of the circle into half and thus one of insides of the circle is in contact with the other opposite inside of the circle, the length (a) of the virtual perpendicular line running from a border between the first tubular knit, the second tubular knit, and the connecting knit to the symmetrical line in a continuous side of the first tubular knit and the second tubular knit, the length (b) of the virtual perpendicular line running from the border to the symmetrical line in a side of the connecting knit.

9. A cylindrical bandage according to claim 8, wherein the connecting knit lies between the first tubular knit and the second tubular knit, and
the connecting knit follows a range of 10 to 40% of the circumference of the circle of the endmost part of the first tubular knit and a range of 10 to 40% of the circumference of the circle of the endmost part of the second tubular knit, the circle of the endmost part of the first tubular knit comprising a stitch row on one circle of the wale side and following the second tubular knit and the connecting knit, the circle of the endmost part of the second tubular knit comprising a stitch row on one circle of the wale side and following the first tubular knit and the connecting knit.

10. A cylindrical bandage according to claim 8, wherein both a thickness of the first tubular knit and a thickness of the second tubular knit are within a range of 2 mm to 15 mm.

11. A cylindrical bandage as claimed in claim 8, wherein a compression of a base part around a lateral malleolus part near a heel side of a foot is within a range from 3 mmHg 70 mmHg while the cylindrical bandage is worn on a circumference of an ankle joint of a human body.

12. A cylindrical bandage as claimed in claim 8, wherein a difference in a compression between a base part around a lateral malleolus part near a heel side of a foot and an instep part of the foot is 40% or less while the cylindrical bandage is worn on a circumference of an ankle joint of a human body.

13. A cylindrical bandage according to claim 1, wherein parts of the depression parts extending in the longitudinal direction of the cylindrical bandage and parts of the protrusion parts extending in the longitudinal direction of the cylindrical bandage have one end on a symmetrical line of the cylindrical bandage.

14. A cylindrical bandage according to claim 4, wherein parts of the depression parts extending in the longitudinal direction of the cylindrical bandage and parts of the protrusion parts extending in the longitudinal direction of the cylindrical bandage, of the exterior convex part, have one end on a symmetrical line of the cylindrical bandage.

15. A cylindrical bandage according to claim 1, further comprising:
- a first tubular knit having a first end;
- a second tubular knit following a second end of the first tubular knit that is opposite to the first end; and
- a connecting knit which connects the first tubular knit and the second tubular knit and has an increased number of stitches on a course side between the first tubular knit and the second tubular knit, the course side having a yarn loop-interknitted,
- wherein each of the depression parts and each of the protrusion parts are arranged alternately and continuously through the first tubular knit and the second tubular knit in a circumferential direction perpendicular to the longitudinal direction of the cylindrical bandage, and
- wherein the depression parts and the protrusion parts extend continuously through the second tubular knit and the first tubular knit to the first end thereof in the longitudinal direction, while avoiding the connecting knit.

16. A cylindrical bandage according to claim 4, further comprising:
- a first tubular knit having a first end;
- a second tubular knit following a second end of the first tubular knit that is opposite to the first end; and
- a connecting knit which connects the first tubular knit and the second tubular knit and has an increased number of stitches on a course side between the first tubular knit and the second tubular knit, the course side having a yarn loop-interknitted,
- wherein each of the depression parts and each of the protrusion parts are arranged alternately and continuously through the first tubular knit and the second tubular knit in a circumferential direction perpendicular to the longitudinal direction of the cylindrical bandage, and
- wherein the depression parts and the protrusion parts extend continuously through the second tubular knit and the first tubular knit to the first end thereof in the longitudinal direction, while avoiding the connecting knit.

* * * * *